(12) United States Patent
Sdelci et al.

(10) Patent No.: US 10,702,518 B2
(45) Date of Patent: Jul. 7, 2020

(54) TAF1 INHIBITORS FOR THE THERAPY OF CANCER

(71) Applicant: CeMM—Forschungszentrum für Molekulare Medizin GmbH, Vienna (AT)

(72) Inventors: Sara Sdelci, Vienna (AT); Stefan Kubicek, Vienna (AT)

(73) Assignee: CeMM—Forschungszentrum für Molekulare Medizin GmbH, Vienna (AT)

( * ) Notice: Subject to any disclaimer, the term of this patent is extended or adjusted under 35 U.S.C. 154(b) by 0 days.

(21) Appl. No.: 16/077,913

(22) PCT Filed: Feb. 15, 2017

(86) PCT No.: PCT/EP2017/053403
§ 371 (c)(1),
(2) Date: Aug. 14, 2018

(87) PCT Pub. No.: WO2017/140728
PCT Pub. Date: Aug. 24, 2017

(65) Prior Publication Data
US 2019/0117641 A1    Apr. 25, 2019

(30) Foreign Application Priority Data
Feb. 15, 2016 (EP) .................... 16155781

(51) Int. Cl.
| | | |
|---|---|---|
| A61K 31/4725 | (2006.01) | |
| A61K 31/5517 | (2006.01) | |
| A61P 35/00 | (2006.01) | |
| C07D 413/12 | (2006.01) | |
| C07D 217/26 | (2006.01) | |
| C07D 407/12 | (2006.01) | |
| C07D 401/12 | (2006.01) | |
| A61K 45/06 | (2006.01) | |
| A61K 31/44 | (2006.01) | |
| A61K 31/513 | (2006.01) | |
| G01N 33/50 | (2006.01) | |
| G01N 33/68 | (2006.01) | |
| G01N 33/574 | (2006.01) | |
| A61K 31/4433 | (2006.01) | |
| A61K 31/472 | (2006.01) | |
| A61K 31/22 | (2006.01) | |
| A61K 31/517 | (2006.01) | |

(52) U.S. Cl.
CPC .......... *A61K 31/4725* (2013.01); *A61K 31/22* (2013.01); *A61K 31/44* (2013.01); *A61K 31/4433* (2013.01); *A61K 31/472* (2013.01); *A61K 31/513* (2013.01); *A61K 31/517* (2013.01); *A61K 31/5517* (2013.01); *A61K 45/06* (2013.01); *A61P 35/00* (2018.01); *C07D 217/26* (2013.01); *C07D 401/12* (2013.01); *C07D 407/12* (2013.01); *C07D 413/12* (2013.01); *G01N 33/5011* (2013.01); *G01N 33/574* (2013.01); *G01N 33/6875* (2013.01)

(58) Field of Classification Search
None
See application file for complete search history.

(56) References Cited

U.S. PATENT DOCUMENTS 8,642,660 B2 * 2/2014 Goldfarb ............ A61K 31/122
                                                         514/641

FOREIGN PATENT DOCUMENTS

| WO | WO 2010072597 | 7/2010 |
|---|---|---|
| WO | WO 2013027168 | 2/2013 |
| WO | WO 2013068489 | 5/2013 |
| WO | WO 2014120808 | 8/2014 |
| WO | WO 2015106272 | 7/2015 |
| WO | WO 2016004417 | 1/2016 |
| WO | WO 2016016316 | 2/2016 |

OTHER PUBLICATIONS

Jayashree, B. et al. Med. Chem Res. 2010 vol. 19. pp. 193-209.*
Silva, A., Mini-Reviews in Medicinal Chemistry, 2005, vol. 5, pp. 893-014.*
Zhong, H.-J. et al, PLOS One 2014 vol. 9 p. e92905.*
European Application No. 16155781.4, European Extended Search Report and Search Opinion, pp. 1-12, dated Sep. 30, 2016.
PCT International Application No. PCT/EP2017/053403, PCT International Search Report and Written Opinion, pp. 1-19, dated Jun. 14, 2017.
PCT International Application No. PCT/EP2017/053403, PCT International Preliminary Report on Patentability, pp. 1-10, dated Aug. 30, 2018.
PubChem CID No. 4426703, Sep. 14, 2005.
PubChem CID No. 4525153, Sep. 15, 2005.

(Continued)

*Primary Examiner* — Heidi Reese
(74) *Attorney, Agent, or Firm* — Parker Highlander PLLC

(57) ABSTRACT

The present invention relates to lactam derivatives of formula (I) for use as medicaments as well as pharmaceutical compositions comprising these compounds, particularly for use as inhibitors of the bromodomain-containing protein TAF1 (i.e., transcription initiation factor TFIID subunit 1) and for use in the treatment or prevention of cancer.

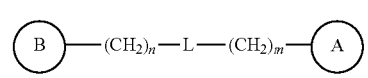

(I)

14 Claims, 29 Drawing Sheets
Specification includes a Sequence Listing.

(56) References Cited

OTHER PUBLICATIONS

PubChem CID No. 4695025, Sep. 16, 2005.
PubChem CID No. 5216403, Oct. 7, 2005.
PubChem CID No. 52898818, May 20, 2011.
PubChem CID No. 52905404, May 20, 2011.
PubChem CID No. 5308052, Dec. 9, 2005.
PubChem CID No. 6624959, Jun. 5, 2006.
PubChem CID No. 22334689, Dec. 5, 2007.
PubChem CID No. 23883170, Feb. 20, 2008.
PubChem CID No. 24152379, Feb. 20, 2008.
PubChem CID No. 110693119, Jan. 18, 2016.
Sdelci, S., et al., "Mapping the Chemical Chromatin Reactivation Landscape Identifies BRD4-TAF1 Cross-Talk", *Nature Chemical Biology*, vol. 12, No. 7, pp. 504-510 +3, May 9, 2016.

\* cited by examiner

Figure 1:
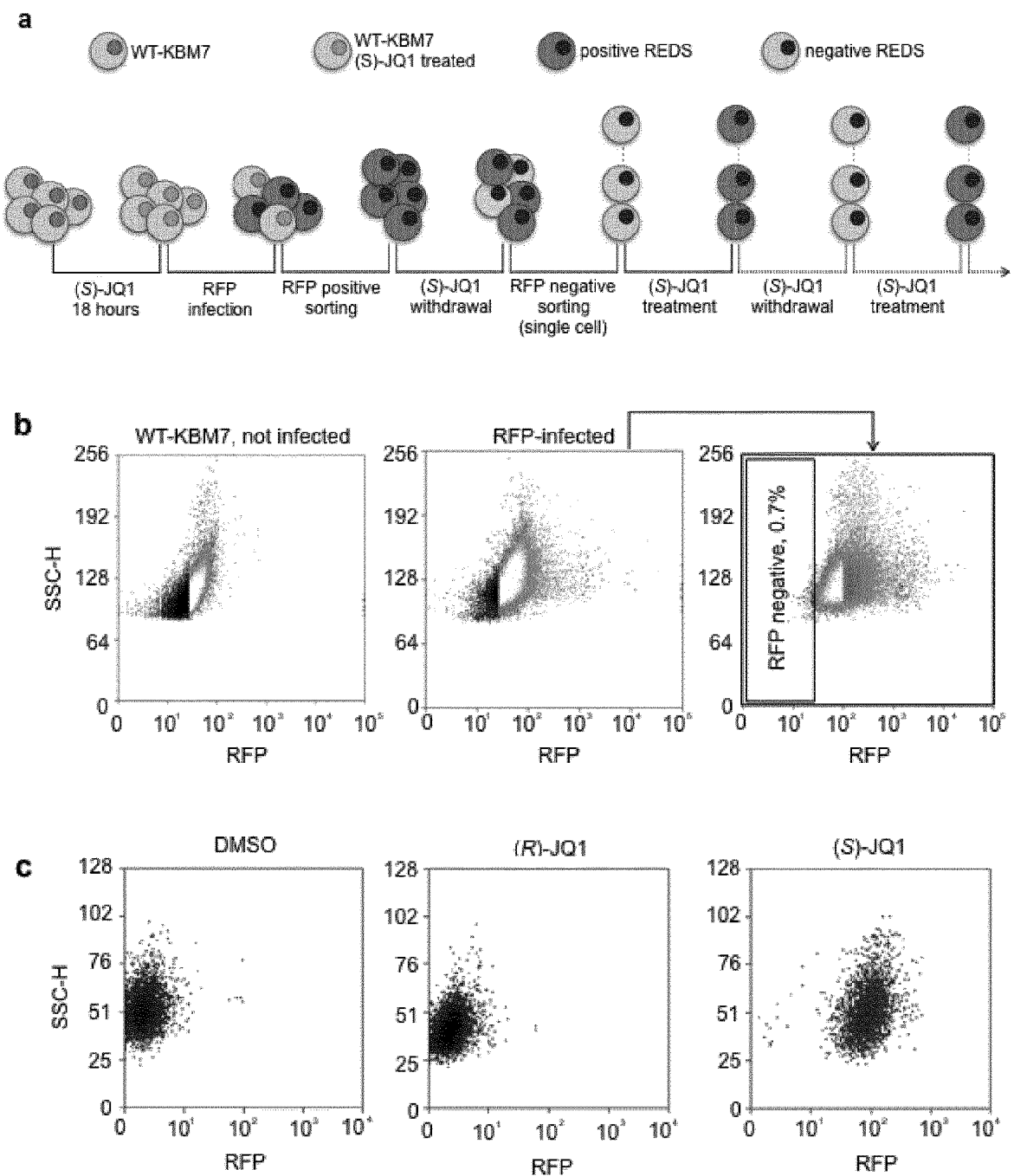

Fig. 1 (cont.)
d
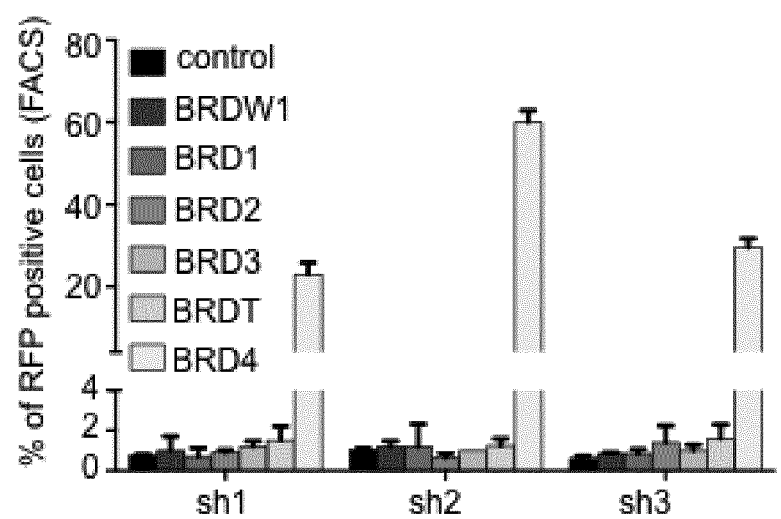
e
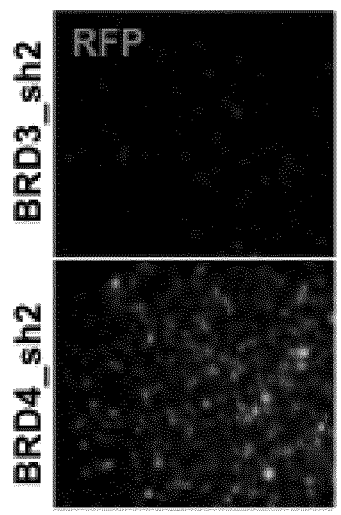

Figure 2:
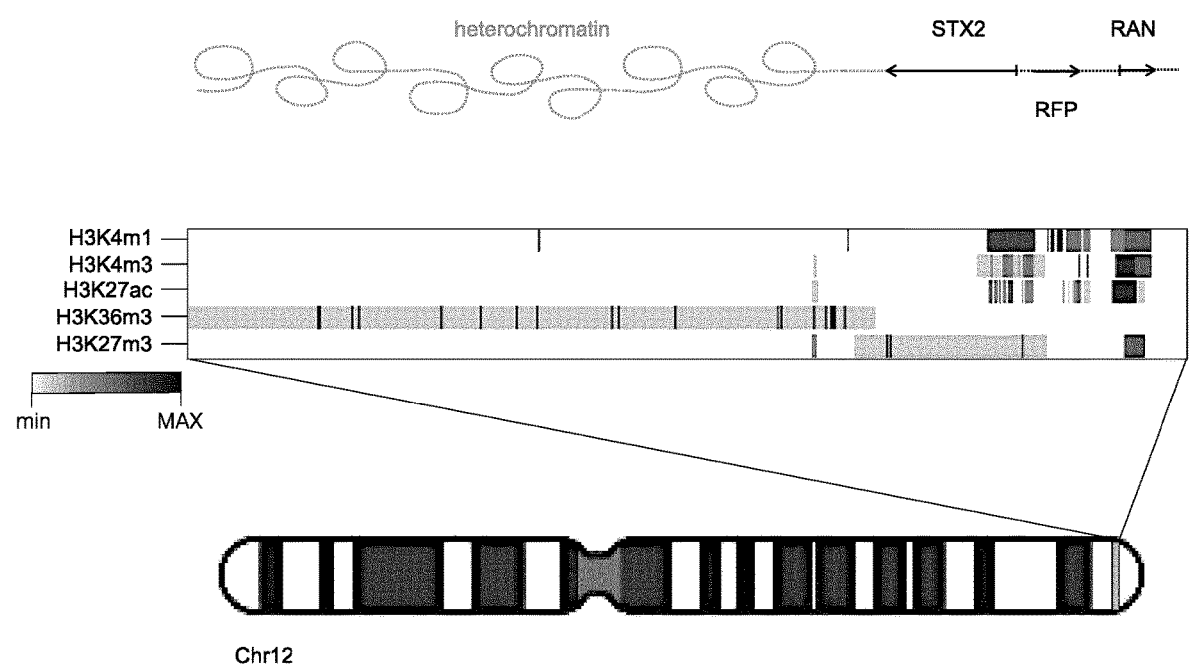
Figure 2:
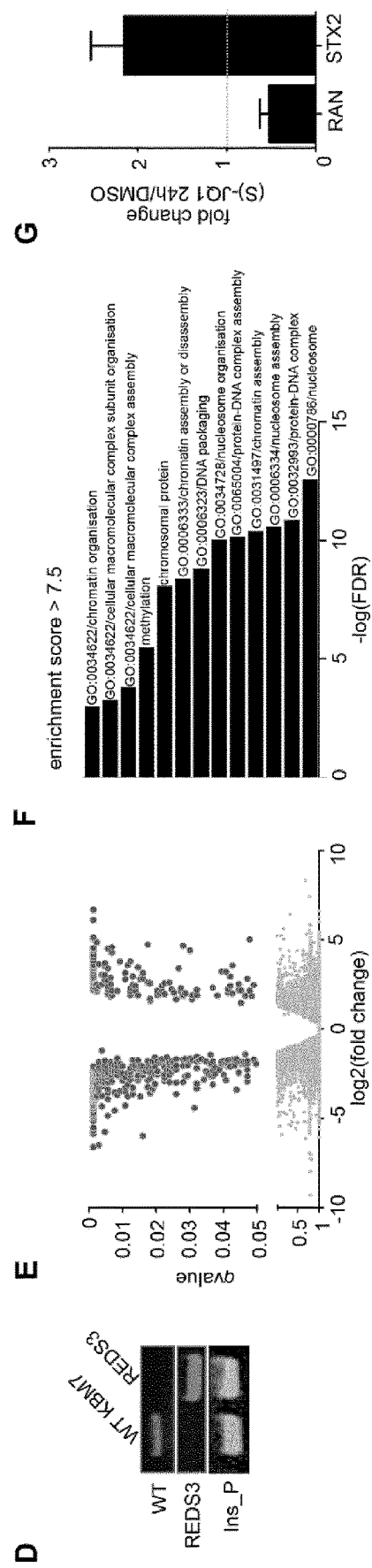

Fig. 2
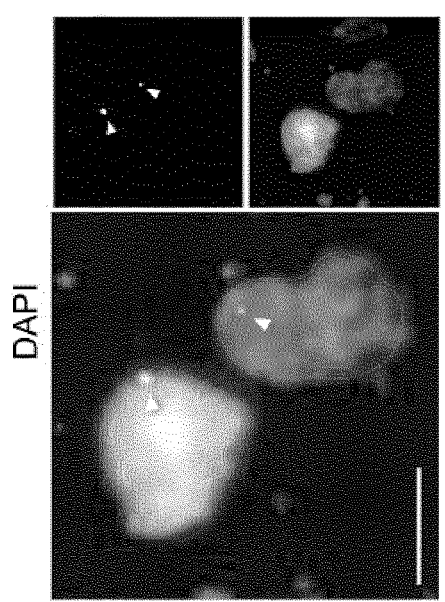
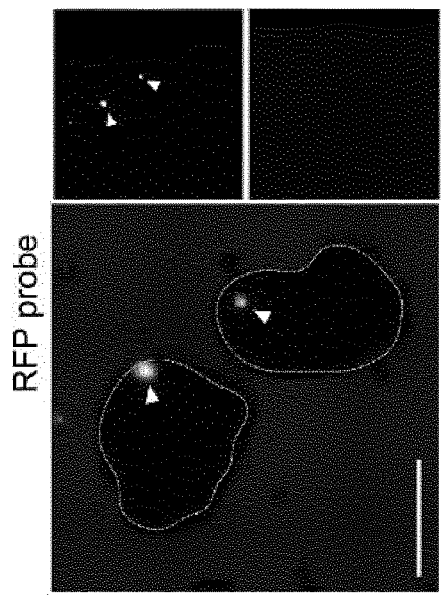
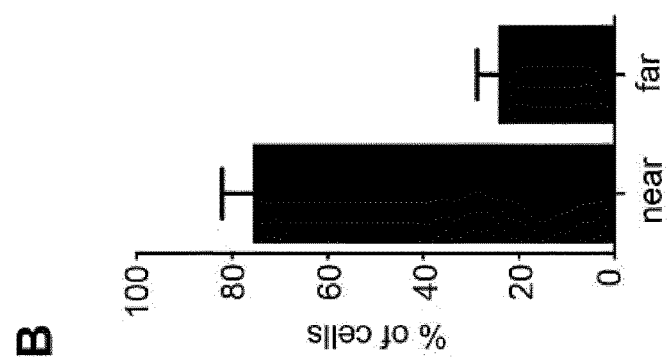

a

Figure 3:
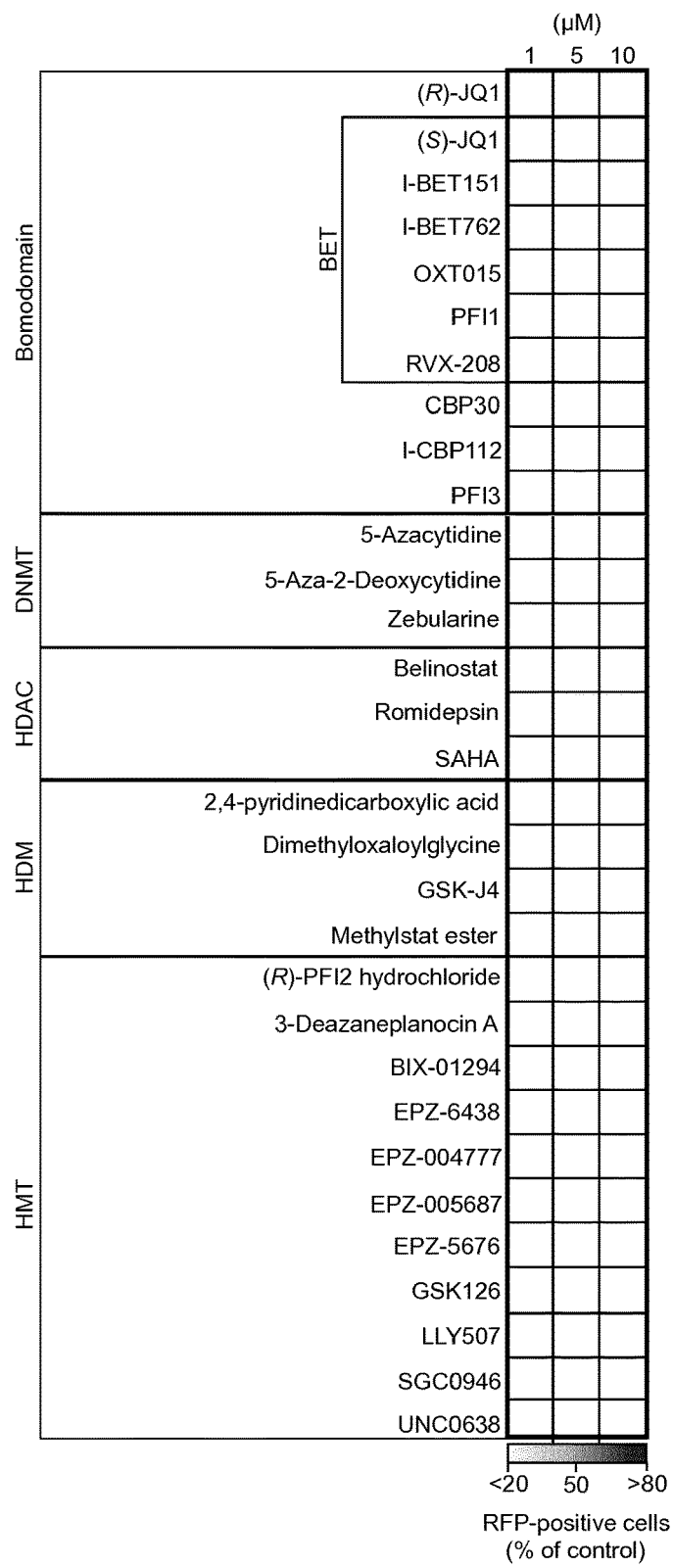

Fig. 3 (cont.)
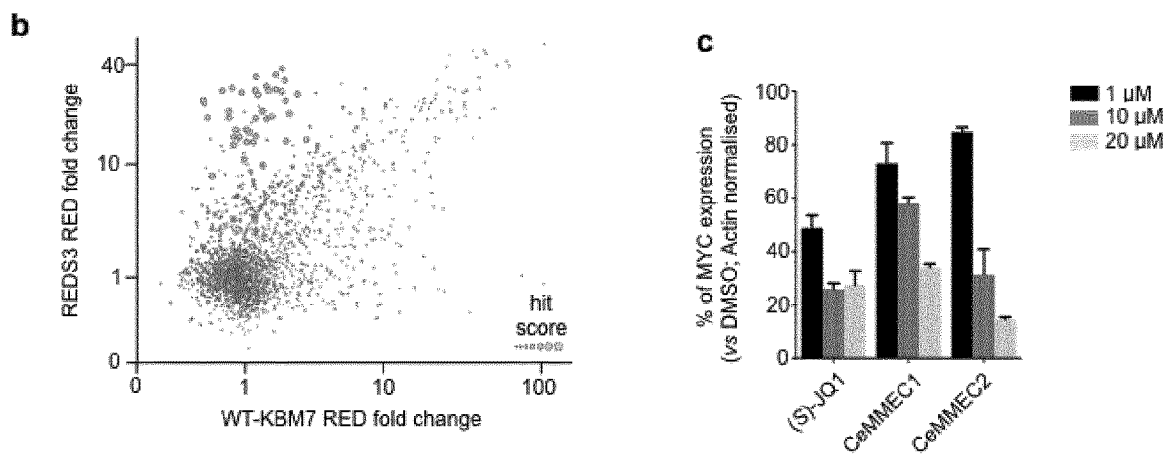
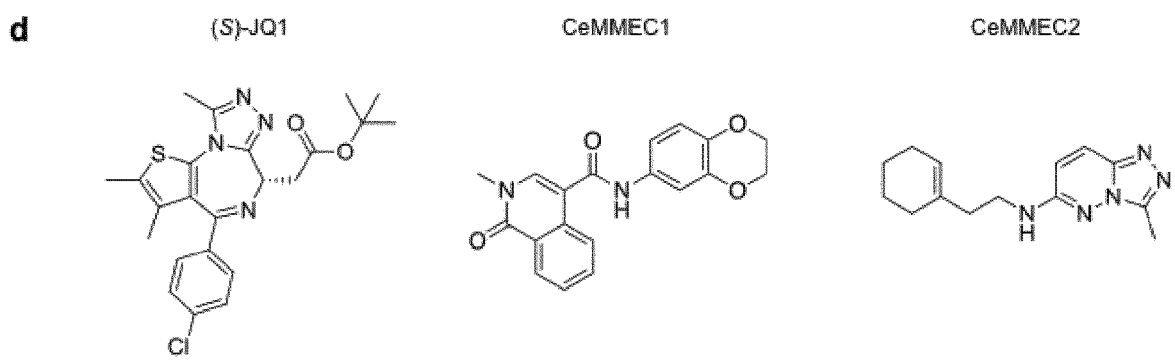
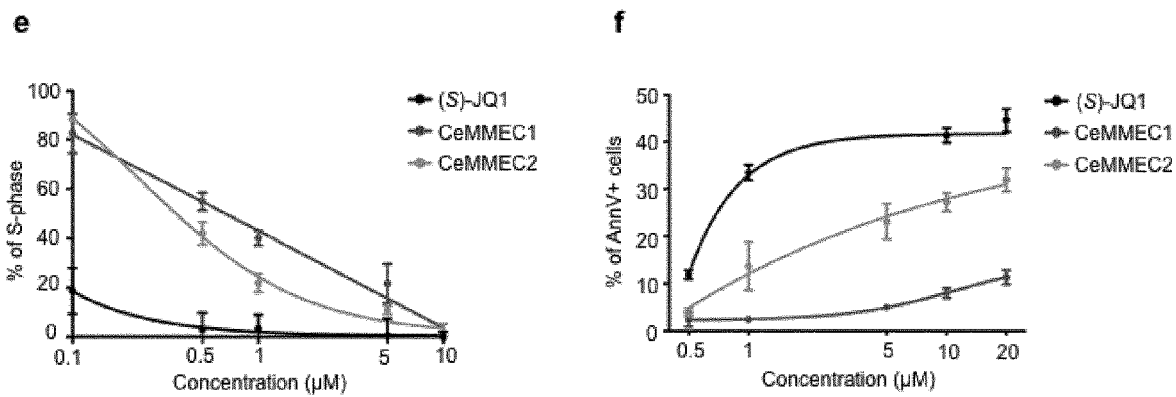

Figure 4:
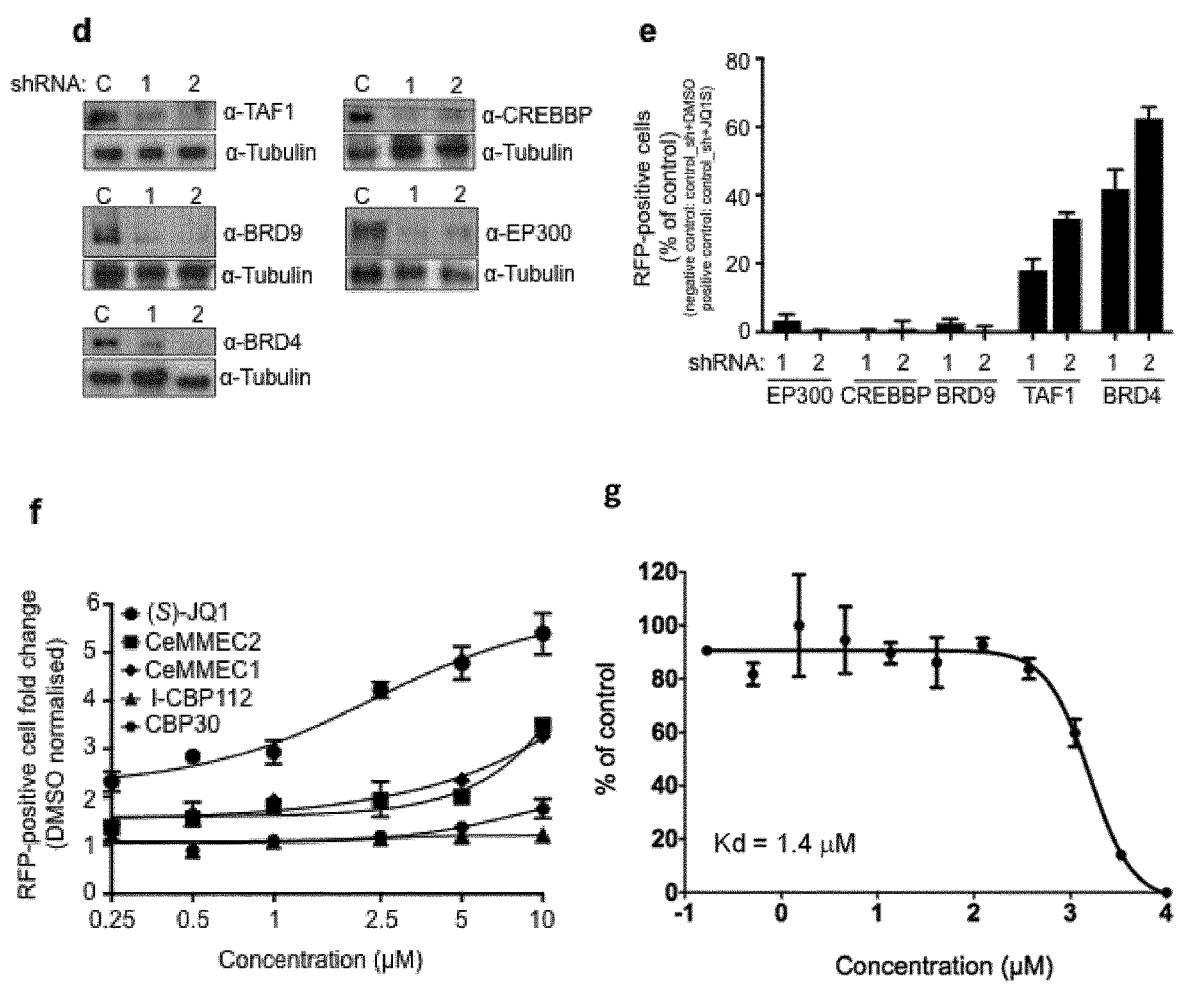

Fig. 4
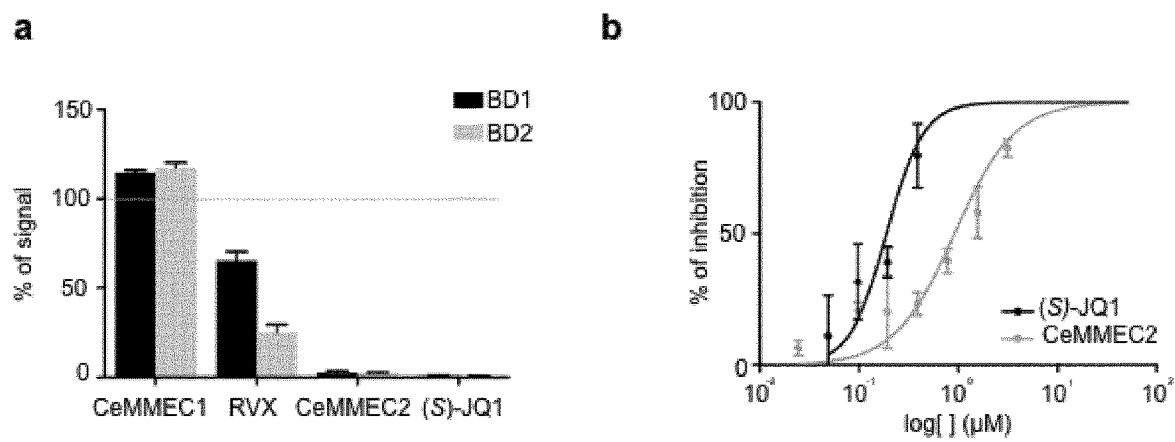
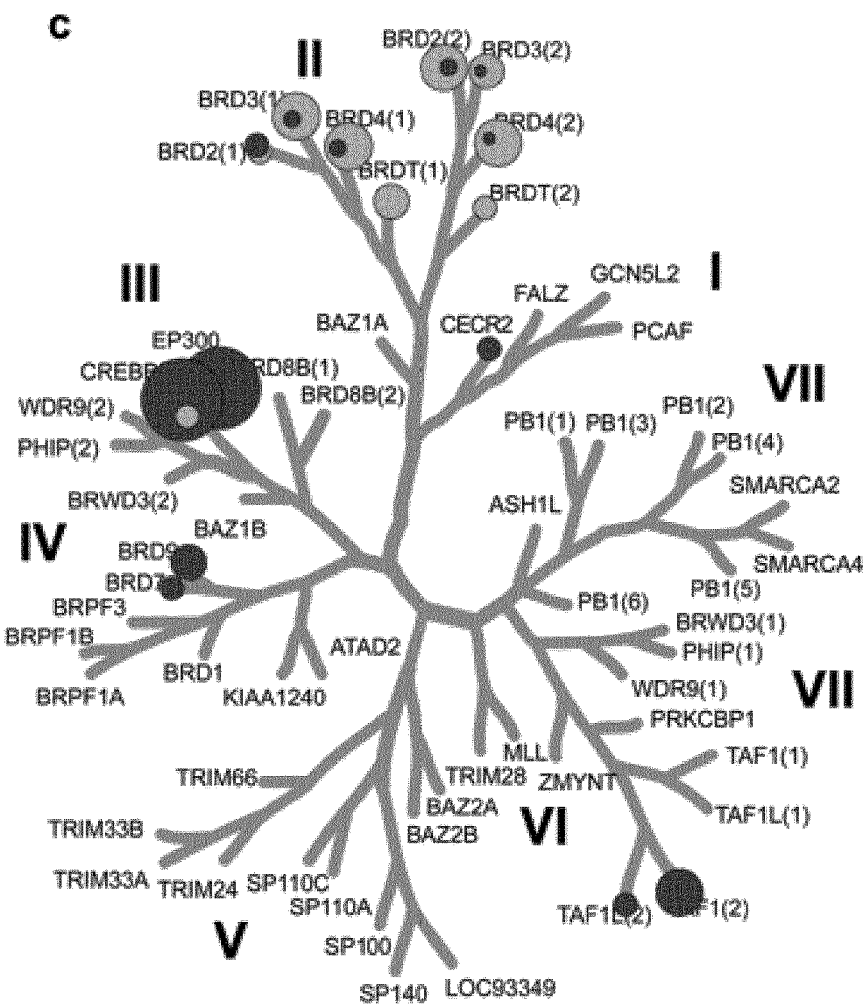

Fig. 4 (cont.)
h
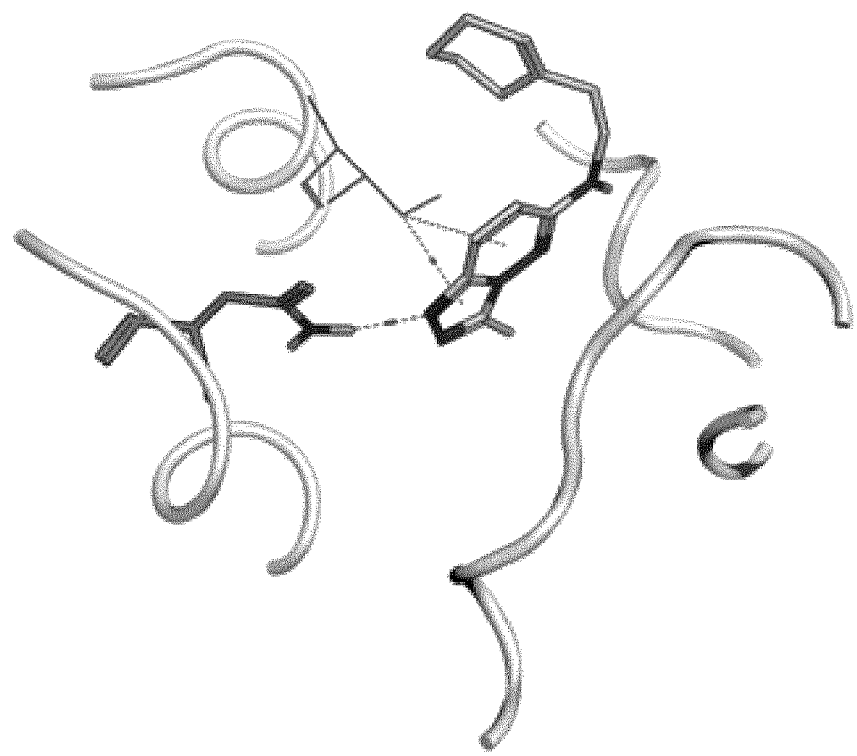
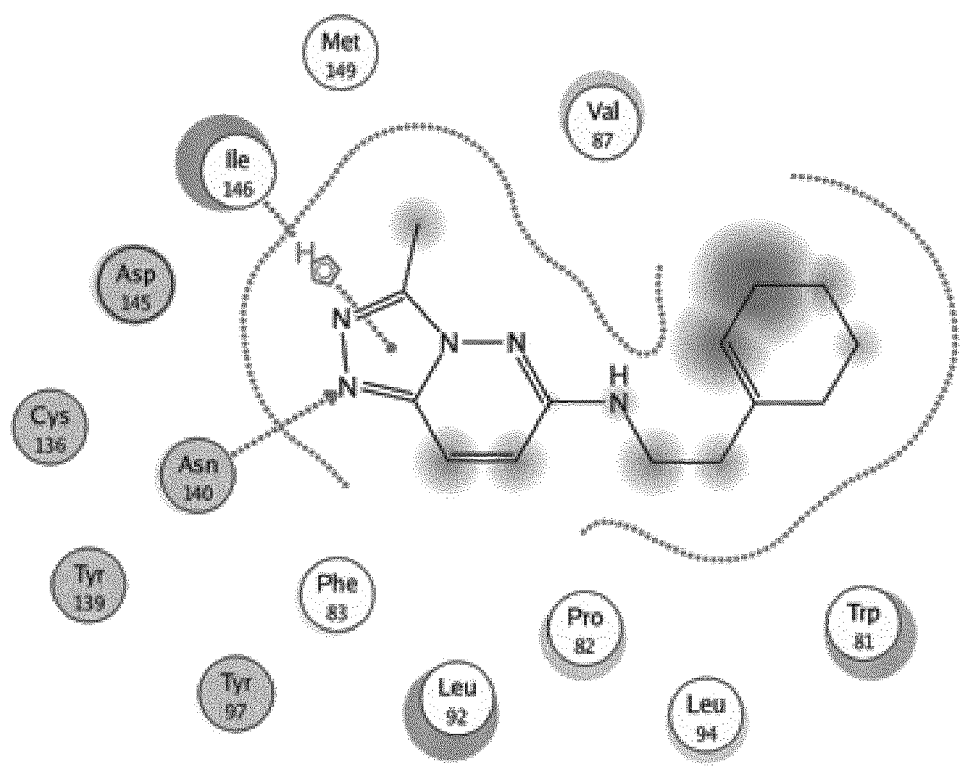

Fig. 4 (cont.)
i
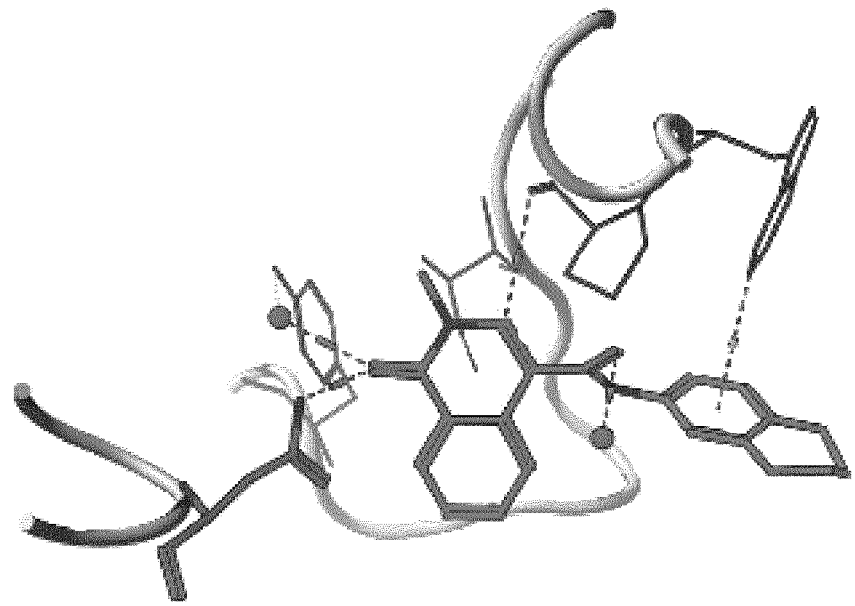
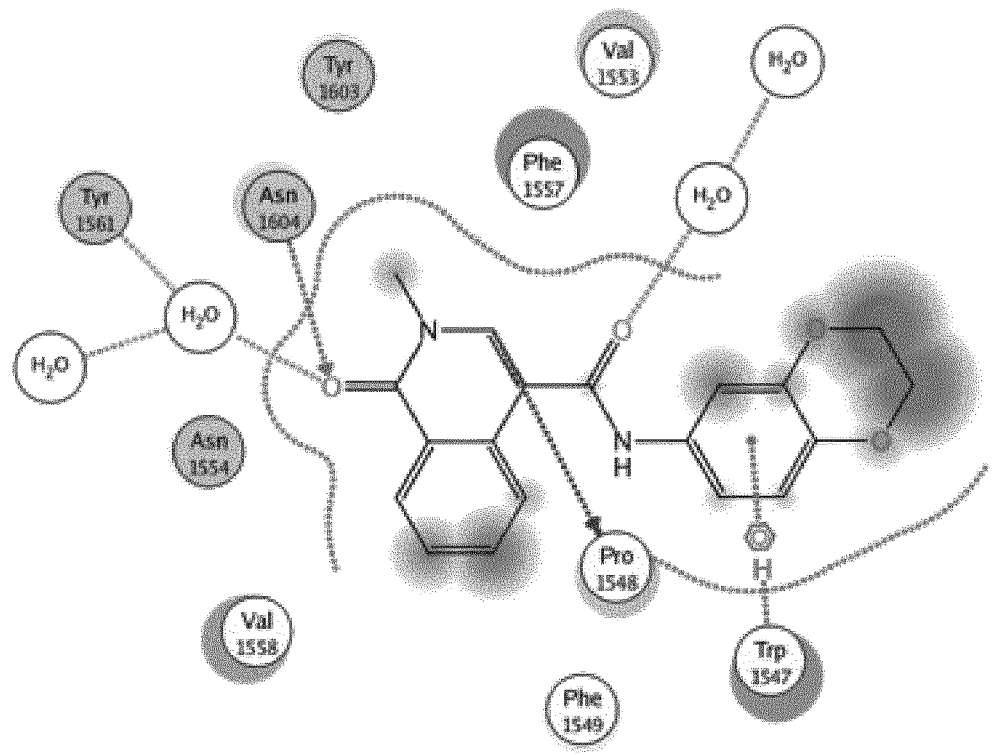

f g

Fig. 6
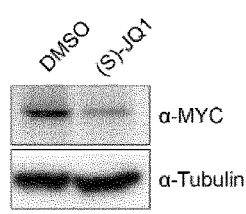
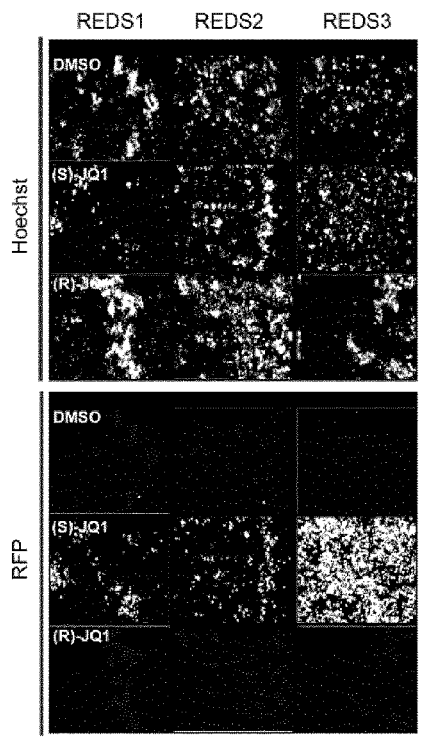
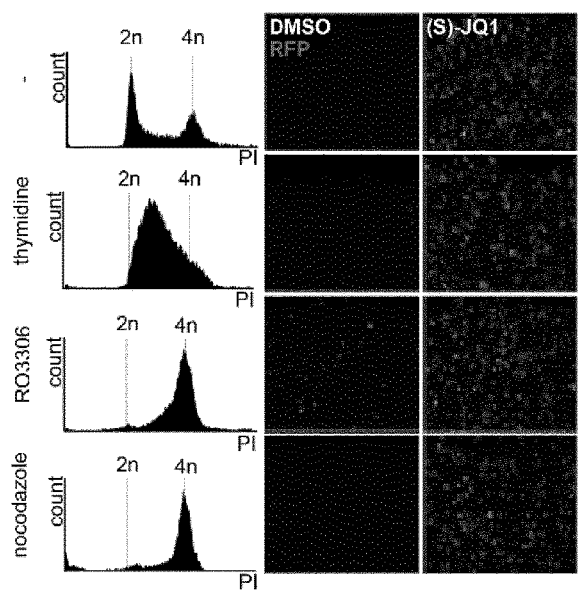
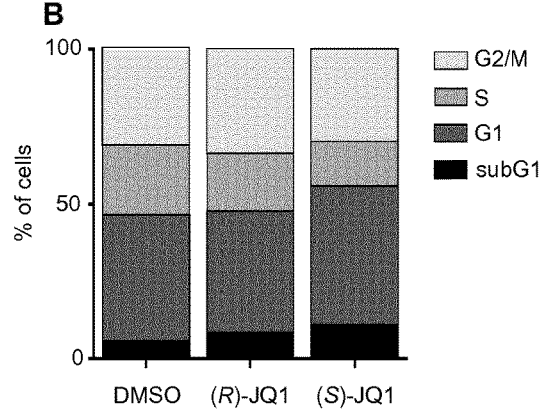
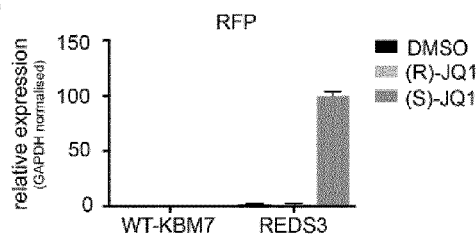
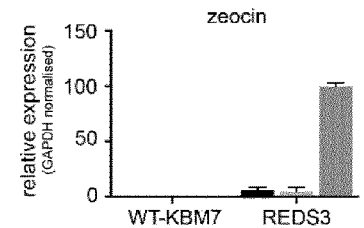
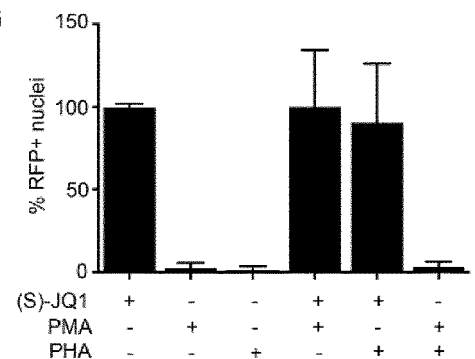
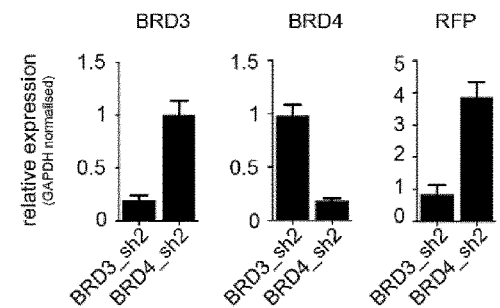

Fig. 7
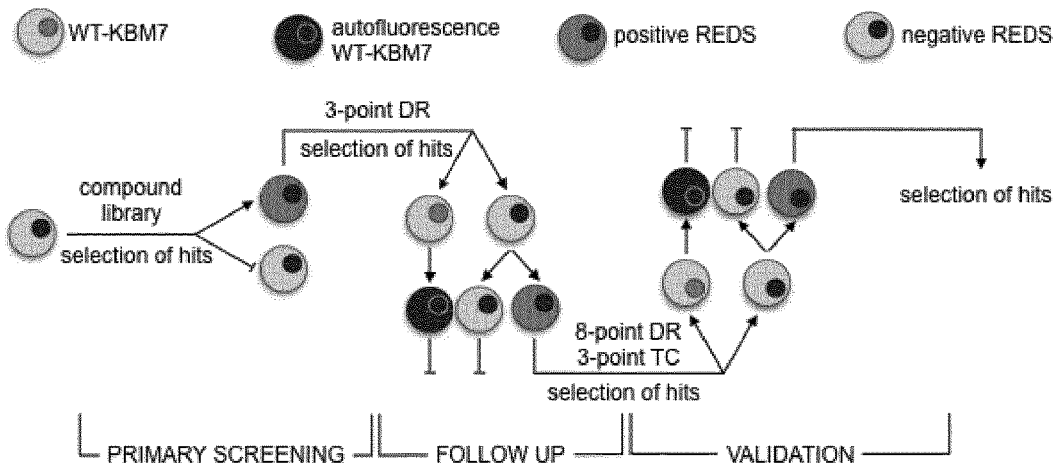
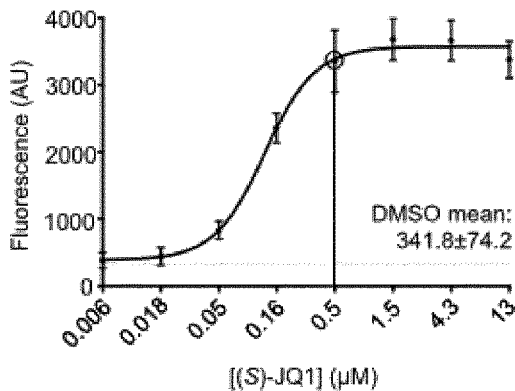
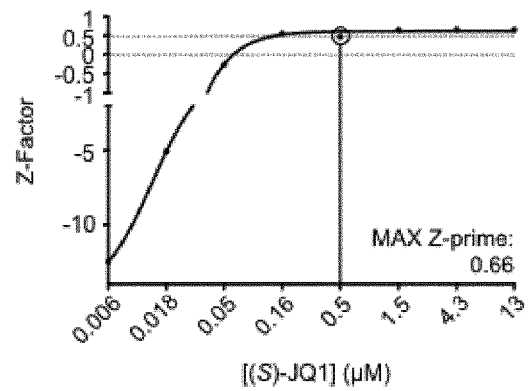
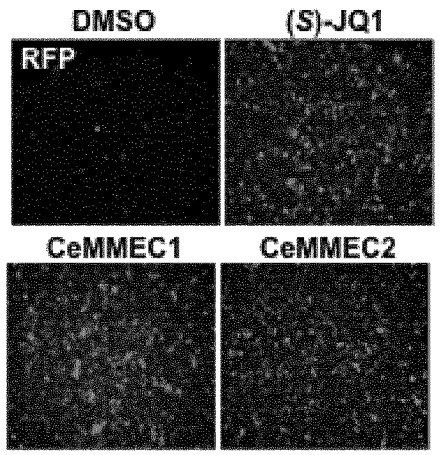
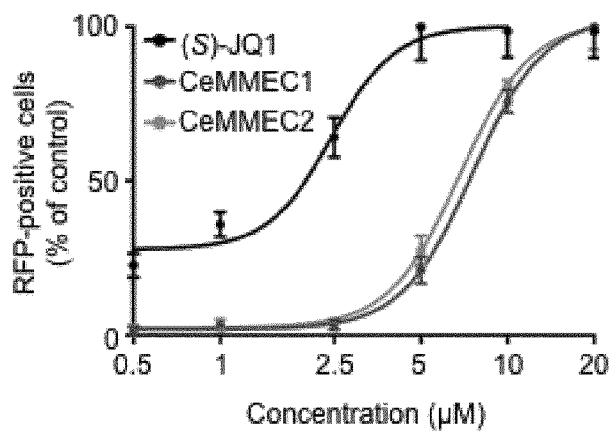

Figure 8:
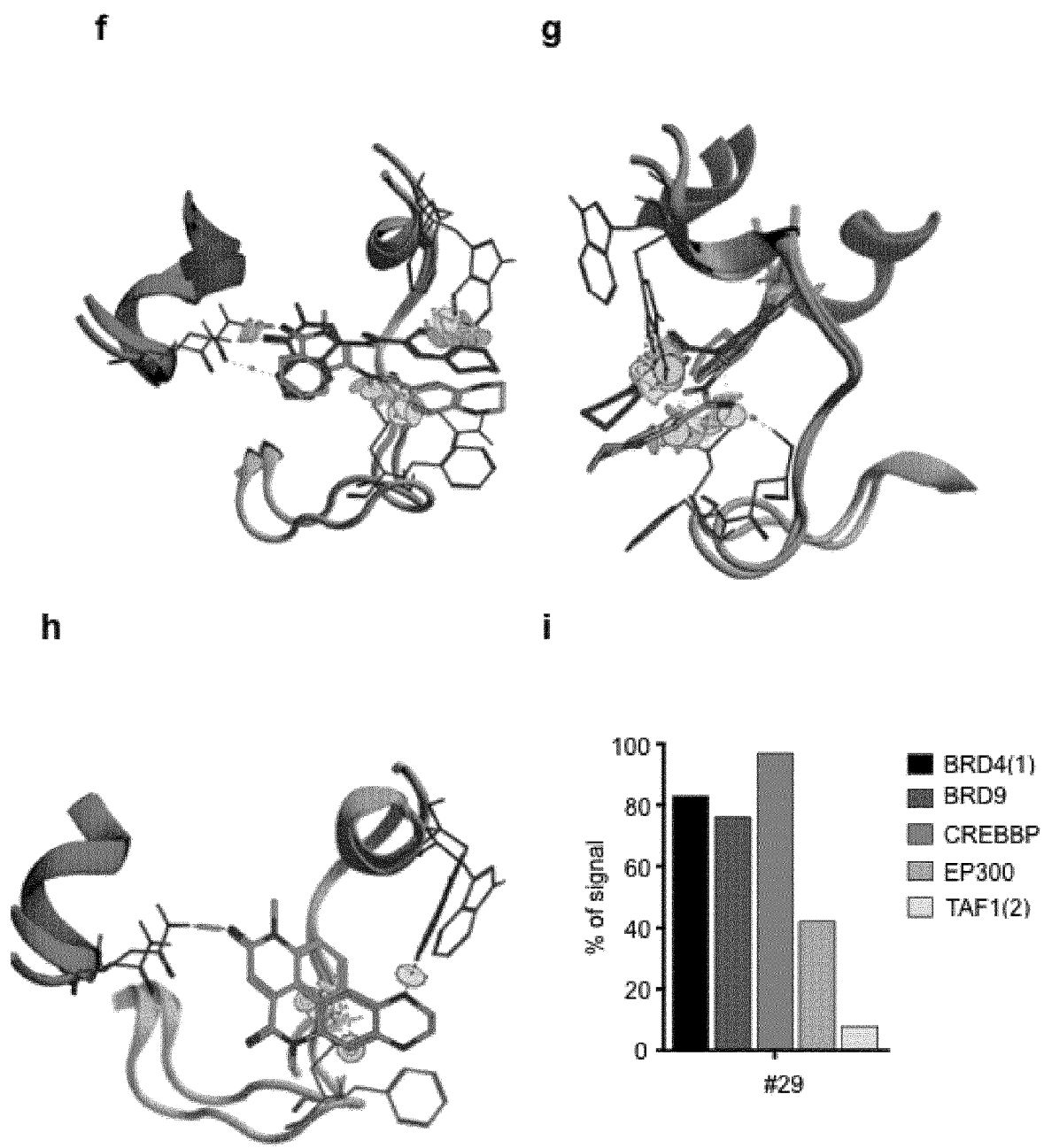

Fig. 7 (cont.)
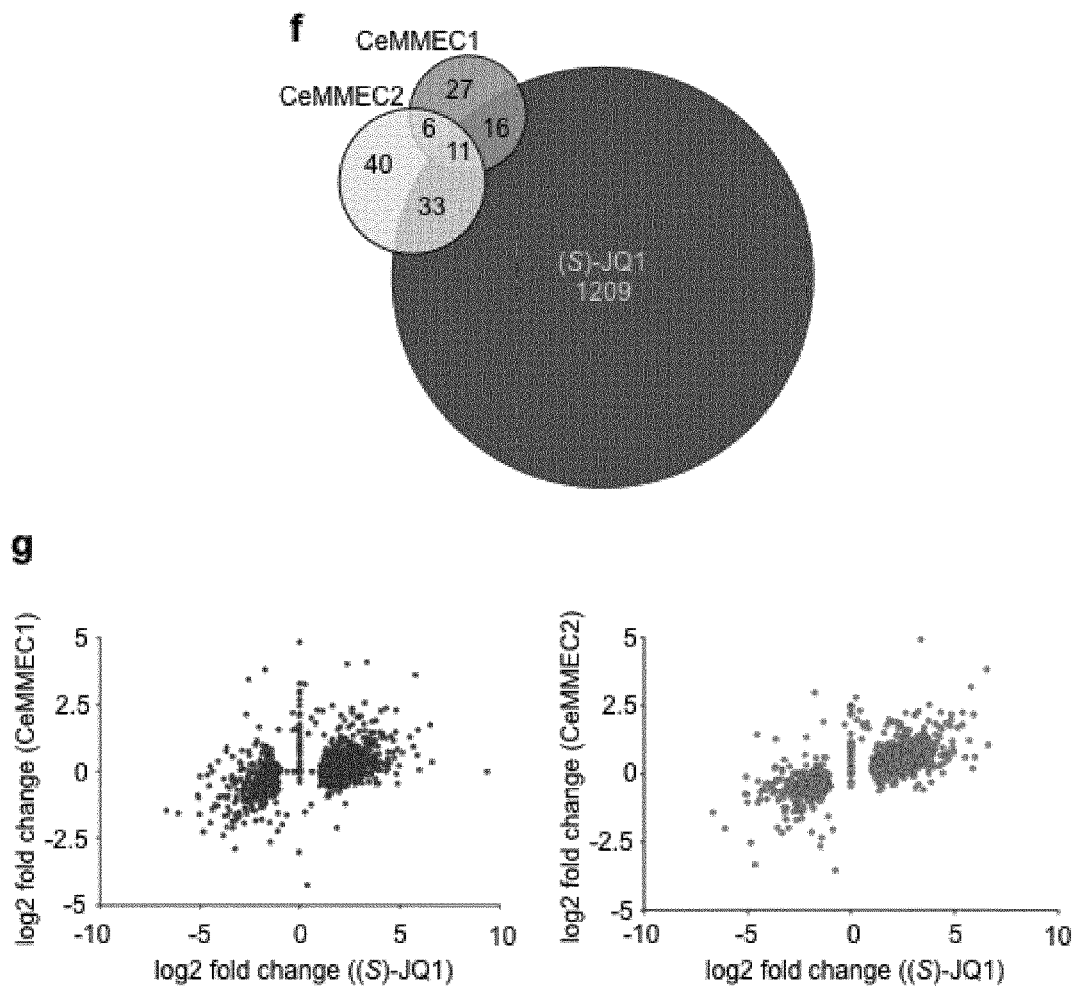
Fig. 8
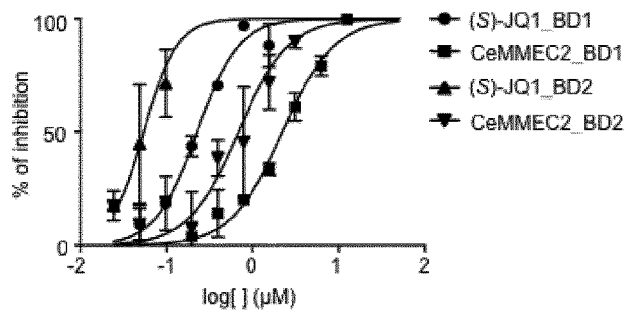
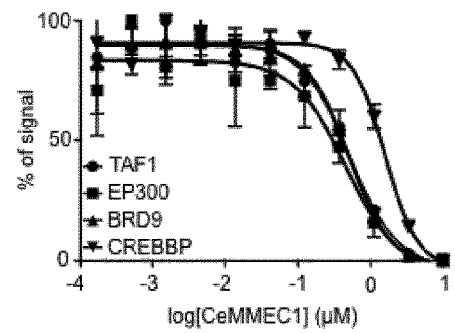

Fig. 8 (cont.)
d
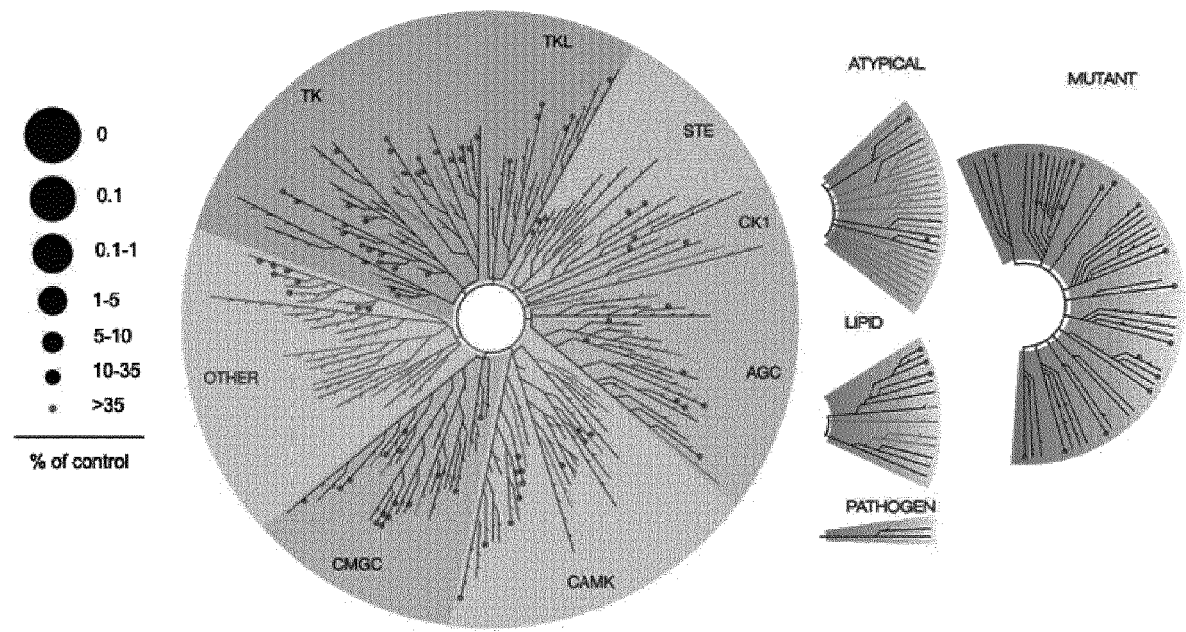
e
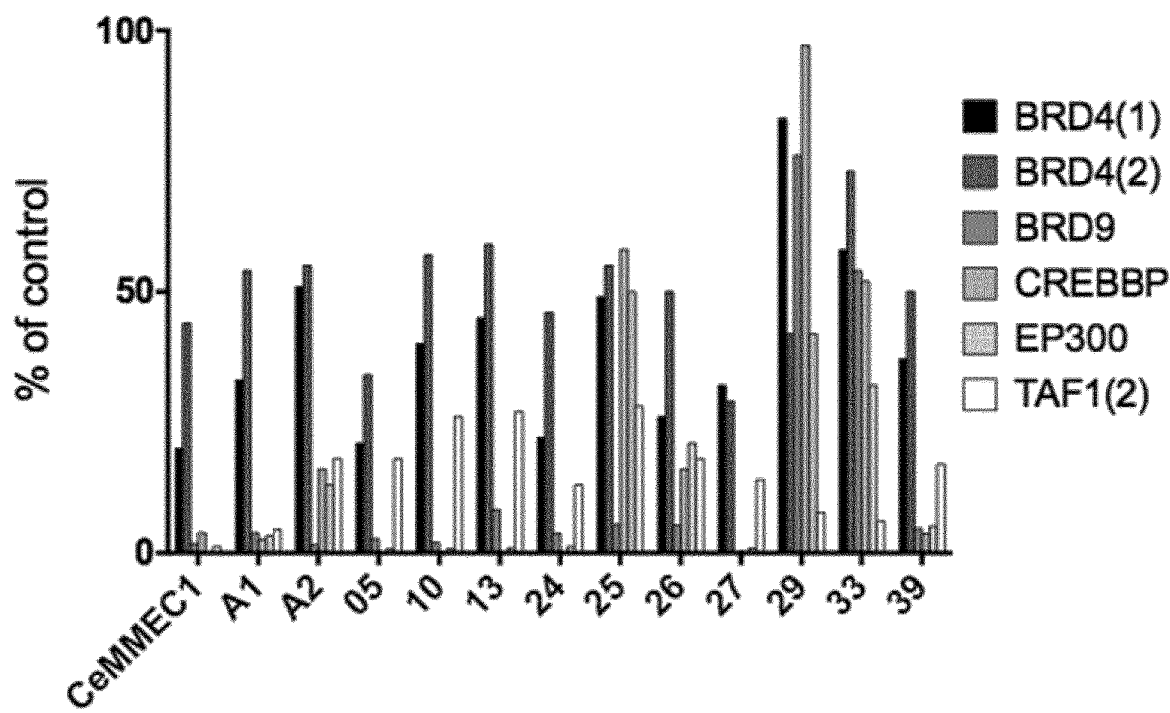

Figure 9:
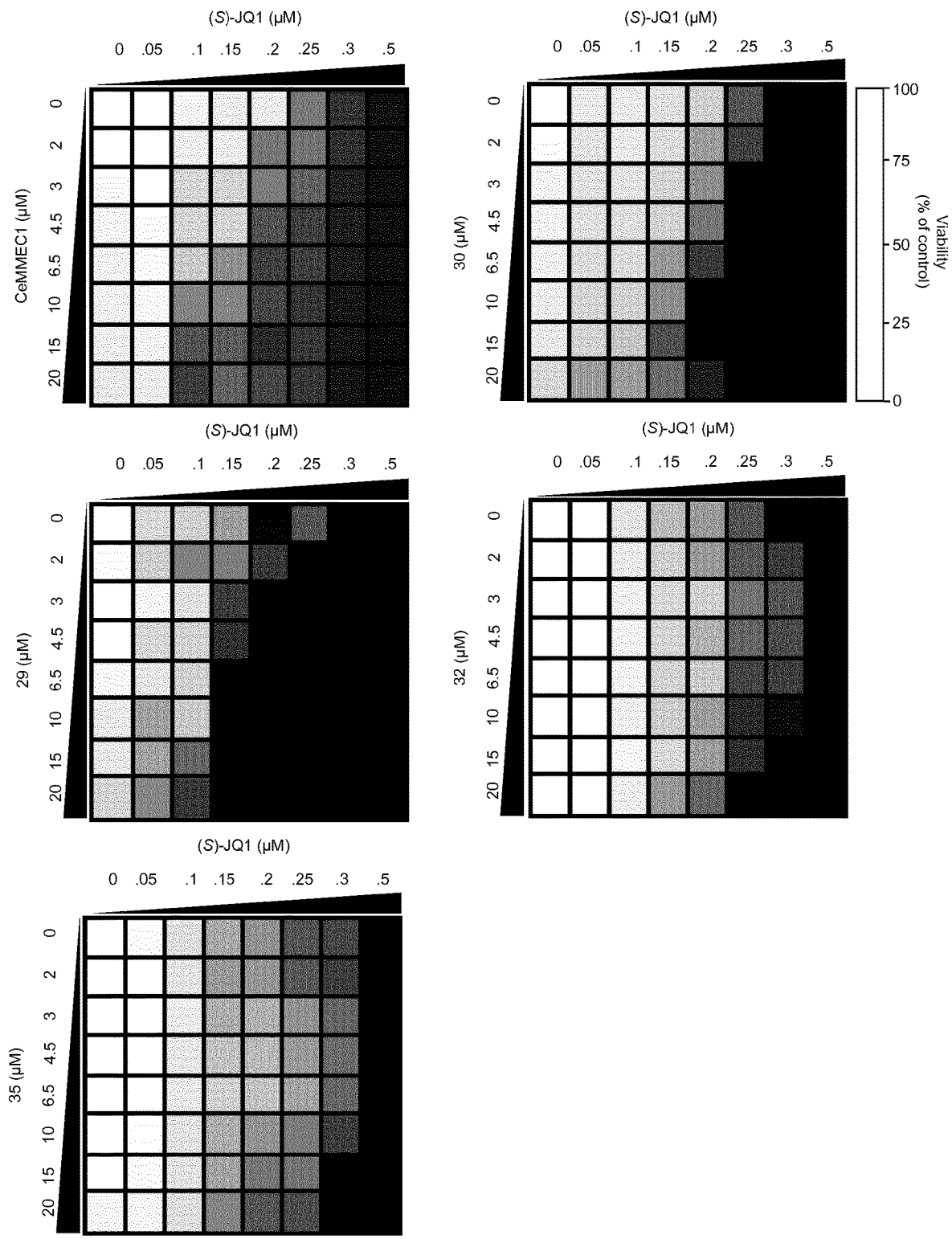

Fig. 9
a
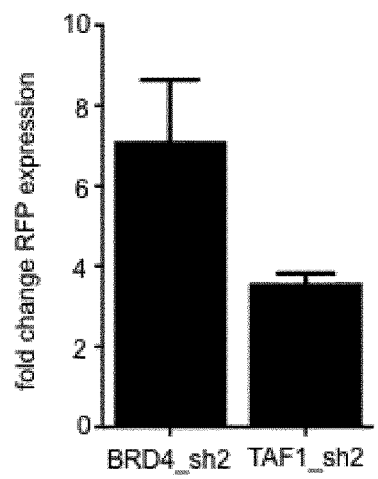
b
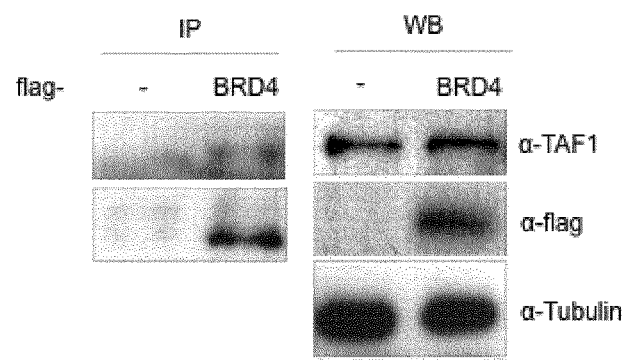
c
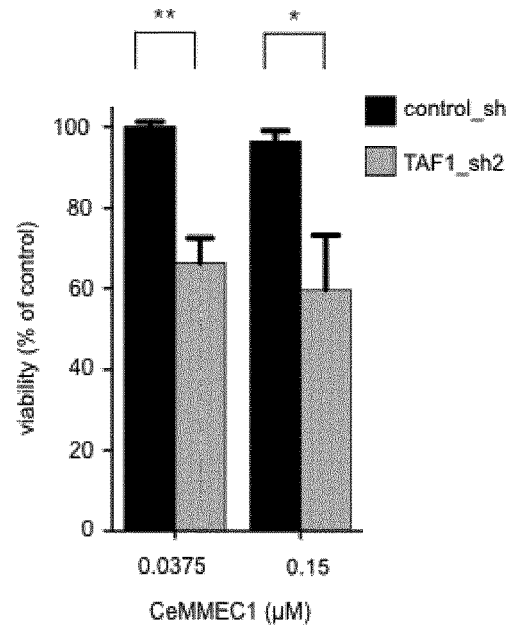

d

Fig. 9 (cont.)

e

| Differential Volume | H23 | THP1 |
|---|---|---|
| CeMMEC1 | 11,48 | 11,66 |
| 29 | 17,32 | 34,49 |
| 30 | 7,43 | 14,53 |
| 32 | 3,41 | -1,85 |
| 35 | 1,62 | -0,76 |

Fig. 10

| Category | Parameter | Description |
|---|---|---|
| Assay | Type of assay | Cell-based reporter assay |
| | Target | BRD4<br>UniProtKB O60885 |
| | Primary measurement | High content imaging for RFP expression |
| | Key reagents | - |
| | Assay protocol | See Compound Screening in Materials and Methods |
| | Additional comments | - |
| Library | Library size | 89,355 small molecules |
| | Library composition | Structural diversity, NIH clinical collection, natural products, approved drugs, known bioactives (e.g. kinase, epigenetic modifiers, ...), natural products, drug-like molecules |
| | Source | Cayman chemical, Enamine Ltd, LC Labs, MedChem Express, Selleck Chemicals, Sigma Aldrich, Tocris, Toronto Research Chemicals |
| | Additional comments | - |

Fig. 10 (cont).

| Category | Parameter | Description |
|---|---|---|
| Library | Library size | 89,355 small molecules |
| | Library composition | Structural diversity, NIH clinical collection, natural products, approved drugs, known bioactives (e.g. kinase, epigenetic modifiers, ...), natural products, drug-like molecules |
| | Source | Cayman chemical, Enamine Ltd, LC Labs, MedChem Express, Selleck Chemicals, Sigma Aldrich, Tocris, Toronto Research Chemicals |
| | Additional comments | - |
| Screen | Format | 384-well plate (Corning 3712) |
| | Concentration(s) tested | Typically 10 µM (0.1% DMSO) |
| | Plate controls | 32 positive control wells ((S)-JQ1, 0.5 µM), 32 negative control wells (DMSO) |
| | Reagent/ compound dispensing system | Echo 520 Liquid Handler<br>Multidrop™ Combi Reagent Dispenser |
| | Detection instrument and software | PerkinElmer Operetta® High Content Imaging System (20X objective and non-confocal mode)<br>PerkinElmer Harmony® High Content Imaging and Analysis Software 3.1.1 |
| | Assay validation/QC | Z' ~ 0.5 (maximum effect with the lowest possible plate-internal positive control, see Suppl. Fig. 2B/C) |
| | Correction factors | - |
| | Normalization | - |
| | Additional comments | - |
| Post-HTS analysis | Hit criteria | For each compound well, the number of RFP-positive cells was compared to that of the mean of the number of RFP-positive cells for the plate-internal negative control wells: 4 standard deviations away were required, or for each compound well, the number of RFP-positive cells needed to be greater than that of the difference between the mean of the number of RFP-positive cells for the plate-internal positive control wells and the mean of the number of RFP-positive cells for the plate-internal negative control wells. |
| | Hit rate | Primary screening hits: 1,286 small molecules (including autofluorescent and toxic compounds as well as technical imaging artefacts)<br>Final screening hits: 22 small molecules |
| | Additional assay(s) | See Compound Screening in Materials and Methods |
| | Confirmation of hit purity and structure | UPLC-MS |
| | Additional comments | See supplementary table 1 for structures and assay results of the 22 screening hits. |

Fig. 11
| Structure | Name | REDness | AlphaLISA | "True hit" | Cell cycle | AnnV+ | Myc |
|---|---|---|---|---|---|---|---|
| 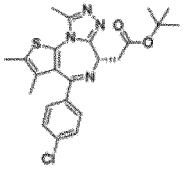 | (S)-JQ1 | > 10 fold | ~90 | Y | subG1/ G1 arrest | ~40 | ~25 |
| 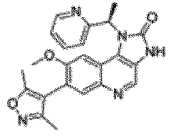 | IBET-151 | > 10 fold | ~90 | Y | ND | ND | ND |
| 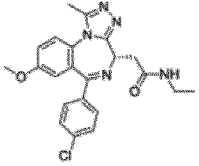 | IBET-762 | > 10 fold | ~90 | Y | ND | ND | ND |
| 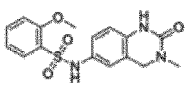 | PFI1 | > 10 fold | ~90 | Y | ND | ND | ND |
| 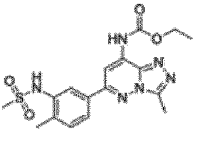 | Bromosporine | 10 fold | ~80 | Y | ND | ND | ND |
| 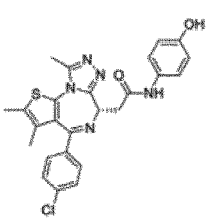 | OXT015 | > 10 fold | ~90 | Y | ND | ND | ND |
| 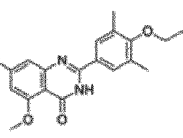 | RVX208 | 2 fold | ~50 | Y | ND | ND | ND |
| 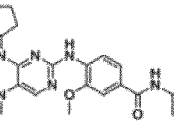 | Bi2536 | > 10 fold | ~90 | Y | ND | ND | ND |
| 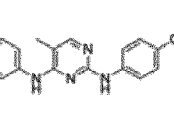 | TG101348 | > 10 fold | ~90 | Y | ND | ND | ND |

Fig. 11 (cont.)

| structure | name | redness | alphaLISA | "true hit" | cell cycle | AnnV+ | Myc |
|---|---|---|---|---|---|---|---|
| 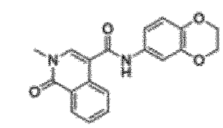 | CeMMEC1 | 2 fold | ~5 | Y | G1 arrest | ~10 | ~50 |
| 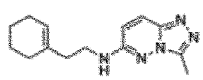 | CeMMEC2 | 2 fold | ~90 | Y | G1 arrest/ subG1 | ~25 | ~30 |
| 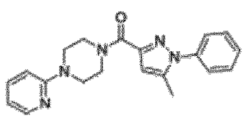 | CeMMEC3 | 1.5 fold | 0 | Y | subG1/ G1 arrest | ~40 | ~40 |
| 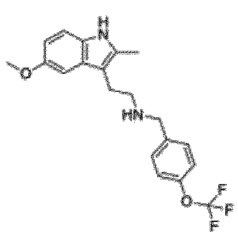 | CeMMEC4 | > 10 fold | ~70 | N | ND | ND | ~80 |
| 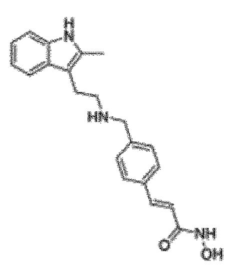 | Panobinostat | 1.5 fold | ~70 | N | subG1/ G1 arrest | ~60 | ~70 |

Fig. 11 (cont.)
| structure | name | redness | alphaLISA | "true hit" | cell cycle | AnnV+ | Myc |
|---|---|---|---|---|---|---|---|
| 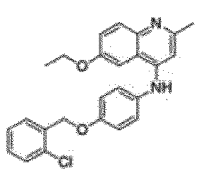 | CeMMEC5 | 1.5 fold | ~40 | N | ND | ~60 | ND |
| 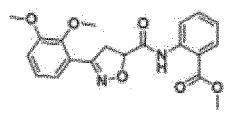 | CeMMEC6 | 2 fold | ~15 | Y | ND | ND | ~90 |
| 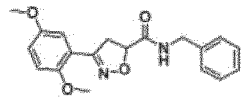 | CeMMEC7 | 1.5 fold | ~20 | Y | ND | ND | ~10 |
| 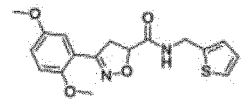 | CeMMEC8 | 1.3 fold | ~20 | Y | ND | ND | ~10 |
| 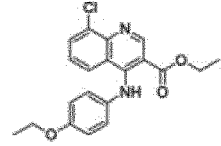 | CeMMEC9 | 4 fold | ~10 | N | ND | ~70 | ND |
| 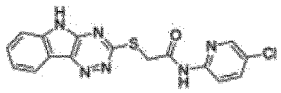 | CeMMEC10 | 3 fold | ~10 | Y | G1 arrest | ND | ~90 |
| 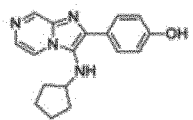 | CeMMEC11 | 1.5 fold | ~5 | Y | ND | ND | 100 |
| 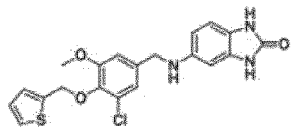 | CeMMEC12 | 3 fold | Y | ND | ND | ~20 | ~90 |

Fig. 12   R1-CO-NH-R2
| Compound | R1 | R2 | REDNESS (% induction at 10 μM) | BRD4 BD1 (% inhibition at 10 μM) | BRD4 BD2 (% inhibition at 10 μM) | BRD9 (% inhibition at 10 μM) | CREBBP (% inhibition at 10 μM) | EP300 (% inhibition at 10 μM) | TAF1 BD2 (% inhibition at 10 μM) |
|---|---|---|---|---|---|---|---|---|---|
| CeMMEC1 |  |  |  | 80 | 56 | 98.2 | 96.1 | 100 | 98.8 |
| 38 |  |  | 35 |  |  |  |  |  |  |
| 29 |  |  | 27 | 17 | 58 | 24 | 3 | 58 | 92.2 |
| 33 |  |  | 4 | 42 | 27 | 46 | 48 | 68 | 93.8 |
| 37 |  |  | 30 |  |  |  |  |  |  |
| 35 |  |  | 1 |  |  |  |  |  |  |
| 32 |  |  | 2 |  |  |  |  |  |  |
| 36 |  |  | 0 |  |  |  |  |  |  |
| A3 |  |  | 0 |  |  |  |  |  |  |
| A5 |  |  | 0 |  |  |  |  |  |  |
| A4 |  |  | 0 |  |  |  |  |  |  |

Fig. 12 (cont.) R1-CO-NH-R2

| Compound | R1 | R2 | REDNESS (% induction at 10 µM) | BRD4 BD1 (% inhibition at 10 µM) | BRD4 BD2 (% inhibition at 10 µM) | BRD9 (% inhibition at 10 µM) | CREBBP (% inhibition at 10 µM) | EP300 (% inhibition at 10 µM) | TAF1 BD2 (% inhibition at 10 µM) |
|---|---|---|---|---|---|---|---|---|---|
| A1 | | | 23 | 67 | 46 | 96.1 | 97.4 | 96.7 | 95.5 |
| 1 | | | 20 | | | | | | |
| 27 | | | 90 | 68 | 71 | 100 | 100 | 99.1 | 86 |
| 3 | | | 20 | | | | | | |
| 5 | | | 80 | 79 | 66 | 97.3 | 100 | 99.25 | 82 |
| 4 | | | 2 | | | | | | |
| 39 | | | 54 | 63 | 50 | 95.3 | 96.3 | 94.9 | 83 |
| 6 | | | 3 | | | | | | |
| 8 | | | 50 | | | | | | |
| 10 | | | 89 | 60 | 43 | 98 | 100 | 99.25 | 74 |
| A2 | | | 18 | 49 | 45 | 98.4 | 84 | 87 | 82 |
| 13 | | | 80 | | | | | | |
| 25 | | | 67 | 55 | 41 | 91.7 | 100 | 99.05 | 73 |
| 26 | | | 80 | 51 | 45 | 94.5 | 42 | 50 | 72 |
| 24 | | | 79 | 74 | 50 | 94.7 | 84 | 79 | 82 |
| 12 | | | 27 | 78 | 54 | 96.2 | 100 | 98.8 | 87 |
| 15 | | | 0 | | | | | | |
| 16 | | | 3 | | | | | | |
| 30 | | | 20 | | | | | | |

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Standard PCR primer WT-KBM7 genome forward

<400> SEQUENCE: 1
cagttccgct acacgtgctg                    20

<210> SEQ ID NO 2
<211> LENGTH: 22
<212> TYPE: DNA
<213> ORGANISM: Artificial Sequence
<220> FEATURE:
<223> OTHER INFORMATION: Standard PCR primer WT-KBM7 genome reverse

<400> SEQUENCE: 2
cgtggaccct taaagagaag gt                 22

<210> SEQ ID NO 3
<211> LENGTH: 20

```
<212> TYPE: DNA
<213> ORGANISM: Artificial Sequence
<220> FEATURE:
<223> OTHER INFORMATION: Standard PCR primer REDS3 genome forward

<400> SEQUENCE: 3
cagttccgct acacgtgctg                                              20

<210> SEQ ID NO 4
<211> LENGTH: 21
<212> TYPE: DNA
<213> ORGANISM: Artificial Sequence
<220> FEATURE:
<223> OTHER INFORMATION: Standard PCR primer REDS3 genome reverse

<400> SEQUENCE: 4
gcgcatgaac tccttgatga c                                            21

<210> SEQ ID NO 5
<211> LENGTH: 25
<212> TYPE: DNA
<213> ORGANISM: Artificial Sequence
<220> FEATURE:
<223> OTHER INFORMATION: Standard PCR primer insulin promoter forward

<400> SEQUENCE: 5
ctctccttga gatgttaatg tggct                                        25

<210> SEQ ID NO 6
<211> LENGTH: 25
<212> TYPE: DNA
<213> ORGANISM: Artificial Sequence
<220> FEATURE:
<223> OTHER INFORMATION: Standard PCR primer insulin promoter reverse

<400> SEQUENCE: 6
cacacggaag atgaggtccg agtgg                                        25

<210> SEQ ID NO 7
<211> LENGTH: 22
<212> TYPE: DNA
<213> ORGANISM: Artificial Sequence
<220> FEATURE:
<223> OTHER INFORMATION: QPCR primer BRD4 forward

<400> SEQUENCE: 7
caggagggtt gtacttatag ca                                           22

<210> SEQ ID NO 8
<211> LENGTH: 22
<212> TYPE: DNA
<213> ORGANISM: Artificial Sequence
<220> FEATURE:
<223> OTHER INFORMATION: QPCR primer BRD4 reverse

<400> SEQUENCE: 8
ctactgtgac atcatcaagc ac                                           22

<210> SEQ ID NO 9
<211> LENGTH: 23
<212> TYPE: DNA
<213> ORGANISM: Artificial Sequence
<220> FEATURE:
<223> OTHER INFORMATION: QPCR primer c-MYC forward

<400> SEQUENCE: 9
```
gaaggtgatc cagactctga cct                                                    23

<210> SEQ ID NO 10
<211> LENGTH: 22
<212> TYPE: DNA
<213> ORGANISM: Artificial Sequence
<220> FEATURE:
<223> OTHER INFORMATION: QPCR primer c-MYC reverse

<400> SEQUENCE: 10
cttctctccg tcctcggatt ct                                                     22

<210> SEQ ID NO 11
<211> LENGTH: 20
<212> TYPE: DNA
<213> ORGANISM: Artificial Sequence
<220> FEATURE:
<223> OTHER INFORMATION: QPCR primer Actin forward

<400> SEQUENCE: 11
atgatgatat cgccgcgctc                                                        20

<210> SEQ ID NO 12
<211> LENGTH: 17
<212> TYPE: DNA
<213> ORGANISM: Artificial Sequence
<220> FEATURE:
<223> OTHER INFORMATION: QPCR primer Actin reverse

<400> SEQUENCE: 12
ccaccatcac gccctgg                                                           17

<210> SEQ ID NO 13
<211> LENGTH: 22
<212> TYPE: DNA
<213> ORGANISM: Artificial Sequence
<220> FEATURE:
<223> OTHER INFORMATION: QPCR primer BRD3 forward

<400> SEQUENCE: 13
aagaagaagg acaaggagaa gg                                                     22

<210> SEQ ID NO 14
<211> LENGTH: 20
<212> TYPE: DNA
<213> ORGANISM: Artificial Sequence
<220> FEATURE:
<223> OTHER INFORMATION: QPCR primer BRD3 reverse

<400> SEQUENCE: 14
cttcttggca ggagccttct                                                        20

<210> SEQ ID NO 15
<211> LENGTH: 20
<212> TYPE: DNA
<213> ORGANISM: Artificial Sequence
<220> FEATURE:
<223> OTHER INFORMATION: QPCR primer TAF1 forward

<400> SEQUENCE: 15
tgcccaggag attgtgaacg                                                        20

<210> SEQ ID NO 16
<211> LENGTH: 18
<212> TYPE: DNA
<213> ORGANISM: Artificial Sequence

```
<220> FEATURE:
<223> OTHER INFORMATION: QPCR primer TAF1 reverse

<400> SEQUENCE: 16
ggcttagcct gaggcgtg                                                  18

<210> SEQ ID NO 17
<211> LENGTH: 20
<212> TYPE: DNA
<213> ORGANISM: Artificial Sequence
<220> FEATURE:
<223> OTHER INFORMATION: QPCR primer CREBP forward

<400> SEQUENCE: 17
agcagcagct ggttctactg                                                20

<210> SEQ ID NO 18
<211> LENGTH: 20
<212> TYPE: DNA
<213> ORGANISM: Artificial Sequence
<220> FEATURE:
<223> OTHER INFORMATION: QPCR primer CREBP reverse

<400> SEQUENCE: 18
cacaatgggc aacttggcag                                                20

<210> SEQ ID NO 19
<211> LENGTH: 20
<212> TYPE: DNA
<213> ORGANISM: Artificial Sequence
<220> FEATURE:
<223> OTHER INFORMATION: QPCR primer EP300 forward

<400> SEQUENCE: 19
gcagtgtgcc aaaccagatg                                                20

<210> SEQ ID NO 20
<211> LENGTH: 20
<212> TYPE: DNA
<213> ORGANISM: Artificial Sequence
<220> FEATURE:
<223> OTHER INFORMATION: QPCR primer EP300 reverse

<400> SEQUENCE: 20
catagcccat aggcgggttg                                                20

<210> SEQ ID NO 21
<211> LENGTH: 23
<212> TYPE: DNA
<213> ORGANISM: Artificial Sequence
<220> FEATURE:
<223> OTHER INFORMATION: QPCR primer STX2 forward

<400> SEQUENCE: 21
ggcaagaagg aaattgatgt tca                                            23

<210> SEQ ID NO 22
<211> LENGTH: 20
<212> TYPE: DNA
<213> ORGANISM: Artificial Sequence
<220> FEATURE:
<223> OTHER INFORMATION: QPCR primer STX2 reverse

<400> SEQUENCE: 22
agacgttcgg ttgtgcttct                                                20
```

```
<210> SEQ ID NO 23
<211> LENGTH: 21
<212> TYPE: DNA
<213> ORGANISM: Artificial Sequence
<220> FEATURE:
<223> OTHER INFORMATION: QPCR primer RAN forward

<400> SEQUENCE: 23
gagaagaacc accttgggtg t                                            21

<210> SEQ ID NO 24
<211> LENGTH: 20
<212> TYPE: DNA
<213> ORGANISM: Artificial Sequence
<220> FEATURE:
<223> OTHER INFORMATION: QPCR primer RAN reverse

<400> SEQUENCE: 24
tccaccgaat ttctcctggc                                              20

<210> SEQ ID NO 25
<211> LENGTH: 20
<212> TYPE: DNA
<213> ORGANISM: Artificial Sequence
<220> FEATURE:
<223> OTHER INFORMATION: QPCR primer RFP forward

<400> SEQUENCE: 25
gggagcgcgt gatgaacttc                                              20

<210> SEQ ID NO 26
<211> LENGTH: 20
<212> TYPE: DNA
<213> ORGANISM: Artificial Sequence
<220> FEATURE:
<223> OTHER INFORMATION: QPCR primer RFP reverse

<400> SEQUENCE: 26
ggaagttcac gccgatgaac                                              20

<210> SEQ ID NO 27
<211> LENGTH: 20
<212> TYPE: DNA
<213> ORGANISM: Artificial Sequence
<220> FEATURE:
<223> OTHER INFORMATION: RFP specific primer forward

<400> SEQUENCE: 27
cggttaaagg tgccgtctcg                                              20

<210> SEQ ID NO 28
<211> LENGTH: 20
<212> TYPE: DNA
<213> ORGANISM: Artificial Sequence
<220> FEATURE:
<223> OTHER INFORMATION: RFP specific primer reverse

<400> SEQUENCE: 28
aggcttccca ggtcacgatg                                              20
```

TAF1 INHIBITORS FOR THE THERAPY OF CANCER

This application is a national phase application under 35 U.S.C. § 371 of International Application No. PCT/EP2017/053403, filed Feb. 15, 2017, which claims benefit of European Application No. 16155781.4, filed Feb. 15, 2016, the entire contents of each of which are hereby incorporated by reference.

The present invention relates to lactam derivatives of formula (I) for use as medicaments as well as pharmaceutical compositions comprising these compounds, particularly for use as inhibitors of the bromodomain-containing protein TAF1 (i.e., transcription initiation factor TFIID subunit 1) and for use in the treatment or prevention of cancer.

Bromodomain proteins of the BET (bromodomain and extraterminal domain) family recognize histone lysine acetylation and mediate transcriptional activation of target genes such as the c-MYC oncogene. Pharmacological BET domain inhibitors promise therapeutic benefits in a variety of cancers. In particular, BRD4 (bromodomain-containing protein 4) is an acetyl-lysine reader of the BET family (Wang, R. et al., 2012; Dey et al., 2003; Filippakopoulos et al., *Cell*, 2012). This protein binds to acetylated histones at promoter and enhancer regions and recruits transcription factors, cofactors and RNA polymerase II (RNApol II), thus modulating the transcription of a subset of genes in a highly context dependent way. Through its effect on target gene expression (Zuber et al., 2011; Wyce et al., 2013), the bromodomain-histone interaction plays a key role regulating cell cycle progression (Dey et al., 2003; Devaiah et al., 2013; Yang et al., 2008; Wu et al., 2007), genomic structure and stability (Wu et al., 2007; Floyd et al., 2013) and development of several pathologies, including cancer (Zuber et al., 2011; Yang et al., 2008; Nagarajan et al., 2014; Wu et al., 2015). The design of chemical probe compounds targeting the two bromodomains of BRD4, such as the pan-BET inhibitors JQ1 (Filippakopoulos et al., 2010) and I-BET-151 (Seal et al., 2012) and their compelling efficacy in cancer models, has prompted the development of drug candidates for these protein interaction modules that are now undergoing clinical trials (Filippakopoulos et al., 2014).

Despite the large number of competing clinical programs, the mechanistic and chemical diversity of currently available BRD4 inhibitors is limited (Filippakopoulos et al., *Cell*, 2012; Filippakopoulos et al., 2014). Furthermore, there is a lack of detailed understanding of the factors affecting BRD4 function, and druggable targets upstream or downstream of BRD4 have remained elusive.

In the context of the present invention, the inventors set out to design a strategy allowing the unbiased scouting of high diversity chemical space for modulators of a BRD4-dependent inactive chromatin state. In the background of the human haploid cell line KBM7 (Andersson et al., 1995), allowing unambiguous monoallelic genetic configurations, the RFP (Red Fluorescent Protein) gene was integrated in heterochromatic loci which are specifically activated by BRD4 inhibition. As described in Example 1, a high-diverse compound library of 89,355 small molecules was then chosen and compounds were selected for their ability to reactivate RFP expression. The efficient identification of many BRD4 inhibitors, including all the BET inhibitors in this library, validated the experimental strategy. Importantly, the setup allowed the identification of small molecules that efficiently induced RFP expression but failed to bind BRD4, indicating a novel mechanism of action that mimics BRD4 inhibition without direct engagement. The inventors surprisingly found that one such compound, CeMMEC1, functioned by binding and potently inhibiting the second bromodomain of the transcription initiation factor TAF1. Moreover, by investigating the properties of this new compound and its derivatives, the inventors surprisingly found a strong synergy between the targeting of TAF1 and BRD4, which resulted in efficient killing of BRD4-dependent cancer cells, as also described in Example 1.

TAF1 is the largest component of the TAF subunits contained in the TFIID core, which is part of the pre-initiation complex (PIC) and serves to recognize the TATA box and correctly place RNAPol II for transcription initiation (Lee et al., 2005; Kloet et al., 2012; Kandiah et al., 2014). Thereby, TAF1 plays a fundamental role in the assembly of the transcription machinery. Similar to BRD4, TAF1 is essential for the viability of many different cell lines (Wang et al., 2015; Blomen et al., 2015), and the two proteins interact not only in the regulation of transcription but also physically in co-immunoprecipitation experiments. It has been demonstrated in the context of the present invention that TAF1 knockdown increases sensitivity to BRD4 inhibition, and BRD4 inhibitors synergize with TAF1 inhibitors (such as the compounds of formula (I) provided herein) to impair viability of BRD4-dependent cancer cell lines. Thus, while the specific functions of the bromodomains of TAF1 have remained elusive, the results provided herein indicate that the second bromodomain of TAF1 is a relevant target in BRD4 driven cancers. Certain BRD4 inhibitors, including bromosporine and a specific 3,5-dimethylisoxazole derivative (McKeown et al., 2014), are known to bind TAF1, but currently there is no specific inhibitor available for this bromodomain-containing protein.

The inventors also found a novel and potent, direct BRD4 inhibitor, i.e., CeMMEC2. Other bromodomain inhibitors have already been described, e.g., in WO 2012/174487, WO 2013/027168, WO 2014/076146, US 2014/0135336, WO 2014/134583, WO 2014/191894, WO 2014/191896, US 2014/0349990, WO 2014/191906, and WO 2016/016316. Furthermore, certain lactam derivatives have been disclosed as having other pharmacological activities, e.g., in WO 2010/072597, WO 2013/068489, WO 2014/120808, WO 2015/106272, and WO 2016/004417.

The present invention solves the problem of providing novel potent inhibitors of TAF1 which can advantageously be used in therapy, particularly in the treatment or prevention of cancer. The invention also provides TAF1 inhibitors that are highly selective for TAF1 over other bromodomain-containing proteins, particularly BRD4.

Accordingly, the present invention provides a compound of the following formula (I)

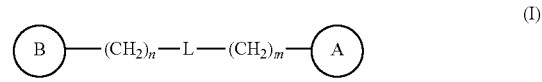

or a pharmaceutically acceptable salt, solvate or prodrug thereof, for use as a medicament and, in particular, for use in the treatment or prevention of cancer.

In formula (I), ring B is a group having the following structure:

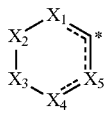

In ring B, one of the ring atoms $X_2$ and $X_3$ is $N(R^{X1})$, and the other one of said ring atoms $X_2$ and $X_3$ is $C(=O)$.

The ring atom $X_1$ is selected from $N(R^{X1})$, $C(R^{X2})$ and $C(=O)$, and the ring atoms $X_4$ and $X_5$ are each independently selected from $N(R^{X1})$, $C(R^{X3})$ and $C(=O)$, wherein at least one of said ring atoms $X_1$, $X_4$, and $X_5$ is different from $N(R^{X1})$ and $C(=O)$.

In the compounds of formula (I), if $X_3$ and $X_5$ are $C(=O)$, $X_4$ is $N(R^{X1})$, and $X_1$ is $C(R^{X2})$, then $X_2$ is $N(H)$.

Each ≈≈≈ is independently a single bond or a double bond, wherein at least one of any two adjacent bonds ≈≈≈ is a single bond.

Each $R^{X1}$ is independently selected from hydrogen, $C_{1-5}$ alkyl, $-CO(C_{1-5}$ alkyl), $-(C_{0-3}$ alkylene)-aryl, and $-(C_{0-3}$ alkylene)-heteroaryl, wherein the aryl comprised in said $-(C_{0-3}$ alkylene)-aryl and the heteroaryl comprised in said $-(C_{0-3}$ alkylene)-heteroaryl are each optionally substituted with one or more groups $R^{X11}$.

$R^{X2}$ is selected from hydrogen, $C_{1-5}$ alkyl, $C_{2-5}$ alkenyl, $C_{2-5}$ alkynyl, $-(C_{0-3}$ alkylene)-OH, $-(C_{0-3}$ alkylene)-O$(C_{1-5}$ alkyl), $-(C_{0-3}$ alkylene)-O$(C_{1-5}$ alkylene)-OH, $-(C_{0-3}$ alkylene)-O$(C_{1-5}$ alkylene)-O$(C_{1-5}$ alkyl), $-(C_{0-3}$ alkylene)-SH, $-(C_{0-3}$ alkylene)-S$(C_{1-5}$ alkyl), $-(C_{0-3}$ alkylene)-NH$_2$, $-(C_{0-3}$ alkylene)-NH$(C_{1-5}$ alkyl), $-(C_{0-3}$ alkylene)-N$(C_{1-5}$ alkyl)$(C_{1-5}$ alkyl), $-(C_{0-3}$ alkylene)-halogen, $-(C_{0-3}$ alkylene)-$(C_{1-5}$ haloalkyl), $-(C_{0-3}$ alkylene)-O$-(C_{1-5}$ haloalkyl), $-(C_{0-3}$ alkylene)-CF$_3$, $-(C_{0-3}$ alkylene)-CN, $-(C_{0-3}$ alkylene)-NO$_2$, $-(C_{0-3}$ alkylene)-CHO, $-(C_{0-3}$ alkylene)-CO$-(C_{1-5}$ alkyl), $-(C_{0-3}$ alkylene)-COOH, $-(C_{0-3}$ alkylene)-CO$-$O$-(C_{1-5}$ alkyl), $-(C_{0-3}$ alkylene)-O$-$CO$-(C_{1-5}$ alkyl), $-(C_{0-3}$ alkylene)-CO$-$NH$_2$, $-(C_{0-3}$ alkylene)-CO$-$NH$(C_{1-5}$ alkyl), $-(C_{0-3}$ alkylene)-CO$-$N$(C_{1-5}$ alkyl)$(C_{1-5}$ alkyl), $-(C_{0-3}$ alkylene)-NH$-$CO$-(C_{1-5}$ alkyl), $-(C_{0-3}$ alkylene)-N$(C_{1-5}$ alkyl)-CO$-(C_{1-5}$ alkyl), $-(C_{0-3}$ alkylene)-SO$_2$$-$NH$_2$, $-(C_{0-3}$ alkylene)-SO$_2$$-$NH$(C_{1-5}$ alkyl), $-(C_{0-3}$ alkylene)-SO$_2$$-$N$(C_{1-5}$ alkyl)$(C_{1-5}$ alkyl), $-(C_{0-3}$ alkylene)-NH$-$SO$_2$$-(C_{1-5}$ alkyl), and $-(C_{0-3}$ alkylene)-N$(C_{1-5}$ alkyl)-SO$_2$$-(C_{1-5}$ alkyl).

The two groups $R^{X3}$ are either mutually linked to form, together with the ring carbon atoms that they are attached to, a 5- or 6-membered cyclyl group which is optionally substituted with one or more groups $R^{X31}$, or the two groups $R^{X3}$ are each independently selected from hydrogen, $C_{1-5}$ alkyl, $C_{2-5}$ alkenyl, $C_{2-5}$ alkynyl, $-$OH, $-$O$(C_{1-5}$ alkyl), $-$O$(C_{1-5}$ alkylene)-OH, $-$O$(C_{1-5}$ alkylene)-O$(C_{1-5}$ alkyl), $-$SH, $-$S$(C_{1-5}$ alkyl), $-$NH$_2$, $-$NH$(C_{1-5}$ alkyl), $-$N$(C_{1-5}$ alkyl)$(C_{1-5}$ alkyl), halogen, $C_{1-5}$ haloalkyl, $-$O$-(C_{1-5}$ haloalkyl), $-$CF$_3$, $-$CN, $-$NO$_2$, $-$CHO, $-$CO$-(C_{1-5}$ alkyl), $-$COOH, $-$CO$-$O$-(C_{1-5}$ alkyl), $-$O$-$CO$-(C_{1-5}$ alkyl), $-$CO$-$NH$_2$, $-$CO$-$NH$(C_{1-5}$ alkyl), $-$CO$-$N$(C_{1-5}$ alkyl)$(C_{1-5}$ alkyl), $-$NH$-$CO$-(C_{1-5}$ alkyl), $-$N$(C_{1-5}$ alkyl)-CO$-(C_{1-5}$ alkyl), $-$SO$_2$$-$NH$_2$, $-$SO$_2$$-$NH$(C_{1-5}$ alkyl), $-$SO$_2$$-$N$(C_{1-5}$ alkyl)$(C_{1-5}$ alkyl), $-$NH$-$SO$_2$$-(C_{1-5}$ alkyl), and $-$N$(C_{1-5}$ alkyl)-SO$_2$$-(C_{1-5}$ alkyl).

Each $R^{X11}$ is independently selected from $C_{1-5}$ alkyl, $C_{2-5}$ alkenyl, $C_{2-5}$ alkynyl, $-(C_{0-3}$ alkylene)-OH, $-(C_{0-3}$ alkylene)-O$(C_{1-5}$ alkyl), $-(C_{0-3}$ alkylene)-O$(C_{1-5}$ alkylene)-OH, $-(C_{0-3}$ alkylene)-O$(C_{1-5}$ alkylene)-O$(C_{1-5}$ alkyl), $-(C_{0-3}$ alkylene)-SH, $-(C_{0-3}$ alkylene)-S$(C_{1-5}$ alkyl), $-(C_{0-3}$ alkylene)-NH$_2$, $-(C_{0-3}$ alkylene)-NH$(C_{1-5}$ alkyl), $-(C_{0-3}$ alkylene)-N$(C_{1-5}$ alkyl)$(C_{1-5}$ alkyl), $-(C_{0-3}$ alkylene)-halogen, alkylene)-$(C_{1-5}$ haloalkyl), $-(C_{0-3}$ alkylene)-O$-(C_{1-5}$ haloalkyl), alkylene)-CF$_3$, $-(C_{0-3}$ alkylene)-CN, $-(C_{0-3}$ alkylene)-NO$_2$, $-(C_{0-3}$ alkylene)-CHO, $-(C_{0-3}$ alkylene)-CO$-(C_{1-5}$ alkyl), $-(C_{0-3}$ alkylene)-COOH, $-(C_{0-3}$ alkylene)-CO$-$O$-(C_{1-5}$ alkyl), $-(C_{0-3}$ alkylene)-O$-$CO$-(C_{1-5}$ alkyl), $-(C_{0-3}$ alkylene)-CO$-$NH$_2$, $-(C_{0-3}$ alkylene)-CO$-$NH$(C_{1-5}$ alkyl), $-(C_{0-3}$ alkylene)-CO$-$N$(C_{1-5}$ alkyl)$(C_{1-5}$ alkyl), $-(C_{0-3}$ alkylene)-NH$-$CO$-(C_{1-5}$ alkyl), $-(C_{0-3}$ alkylene)-N$(C_{1-5}$ alkyl)-CO$-(C_{1-5}$ alkyl), $-(C_{0-3}$ alkylene)-SO$_2$$-$NH$_2$, $-(C_{0-3}$ alkylene)-SO$_2$$-$NH$(C_{1-5}$ alkyl), $-(C_{0-3}$ alkylene)-SO$_2$$-$N$(C_{1-5}$ alkyl)$(C_{1-5}$ alkyl), $-(C_{0-3}$ alkylene)-NH$-$SO$_2$$-(C_{1-5}$ alkyl), and $-(C_{0-3}$ alkylene)-N$(C_{1-5}$ alkyl)-SO$_2$$-(C_{1-5}$ alkyl).

Each $R^{X31}$ is independently selected from $C_{1-5}$ alkyl, $C_{2-5}$ alkenyl, $C_{2-5}$ alkynyl, $-(C_{0-3}$ alkylene)-OH, $-(C_{0-3}$ alkylene)-O$(C_{1-5}$ alkyl), $-(C_{0-3}$ alkylene)-O$(C_{1-5}$ alkylene)-OH, $-(C_{0-3}$ alkylene)-O$(C_{1-5}$ alkylene)-O$(C_{1-5}$ alkyl), $-(C_{0-3}$ alkylene)-SH, $-(C_{0-3}$ alkylene)-S$(C_{1-5}$ alkyl), $-(C_{0-3}$ alkylene)-NH$_2$, $-(C_{0-3}$ alkylene)-NH$(C_{1-5}$ alkyl), $-(C_{0-3}$ alkylene)-N$(C_{1-5}$ alkyl)$(C_{1-5}$ alkyl), $-(C_{0-3}$ alkylene)-halogen, $-(C_{0-3}$ alkylene)-$(C_{1-5}$ haloalkyl), $-(C_{0-3}$ alkylene)-O$-(C_{1-5}$ haloalkyl), $-(C_{0-3}$ alkylene)-CF$_3$, $-(C_{0-3}$ alkylene)-CN, $-(C_{0-3}$ alkylene)-NO$_2$, $-(C_{0-3}$ alkylene)-CHO, $-(C_{0-3}$ alkylene)-CO$-(C_{1-5}$ alkyl), $-(C_{0-3}$ alkylene)-COOH, $-(C_{0-3}$ alkylene)-CO$-$O$-(C_{1-5}$ alkyl), $-(C_{0-3}$ alkylene)-O$-$CO$-(C_{1-5}$ alkyl), $-(C_{0-3}$ alkylene)-CO$-$NH$_2$, $-(C_{0-3}$ alkylene)-CO$-$NH$(C_{1-5}$ alkyl), $-(C_{0-3}$ alkylene)-CO$-$N$(C_{1-5}$ alkyl)$(C_{1-5}$ alkyl), $-(C_{0-3}$ alkylene)-NH$-$CO$-(C_{1-5}$ alkyl), $-(C_{0-3}$ alkylene)-N$(C_{1-5}$ alkyl)-CO$-(C_{1-5}$ alkyl), $-(C_{0-3}$ alkylene)-SO$_2$$-$NH$_2$, $-(C_{0-3}$ alkylene)-SO$_2$$-$NH$(C_{1-5}$ alkyl), $-(C_{0-3}$ alkylene)-SO$_2$$-$N$(C_{1-5}$ alkyl)$(C_{1-5}$ alkyl), $-(C_{0-3}$ alkylene)-NH$-$SO$_2$$-(C_{1-5}$ alkyl), and $-(C_{0-3}$ alkylene)-N$(C_{1-5}$ alkyl)-SO$_2$$-(C_{1-5}$ alkyl).

Ring B is attached to the remainder of the compound of formula (I) via the ring carbon atom that is marked with an asterisk (*) or, if $X_4$ and $X_5$ are each $C(R^{X3})$ and the two groups $R^{X3}$ are mutually linked to form, together with the ring carbon atoms that they are attached to, a 5- or 6-membered cyclyl group which is optionally substituted with one or more groups $R^{X31}$, then ring B may also be attached to the remainder of the compound of formula (I) via any ring carbon atom of said 5- or 6-membered cyclyl group.

Ring A is aryl or heteroaryl, wherein said aryl and said heteroaryl are each optionally substituted with one or more groups $R^A$.

Each $R^A$ is independently selected from $C_{1-5}$ alkyl, $C_{2-5}$ alkenyl, $C_{2-5}$ alkynyl, $-(C_{0-3}$ alkylene)-OH, $-(C_{0-3}$ alkylene)-O$(C_{1-5}$ alkyl), $-(C_{0-3}$ alkylene)-O$(C_{1-5}$ alkylene)-OH, $-(C_{0-3}$ alkylene)-O$(C_{1-5}$ alkylene)-O$(C_{1-5}$ alkyl), $-(C_{0-3}$ alkylene)-SH, $-(C_{0-3}$ alkylene)-S$(C_{1-5}$ alkyl), $-(C_{0-3}$ alkylene)-NH$_2$, $-(C_{0-3}$ alkylene)-NH$(C_{1-5}$ alkyl), $-(C_{0-3}$ alkylene)-N$(C_{1-5}$ alkyl)$(C_{1-5}$ alkyl), $-(C_{0-3}$ alkylene)-halogen, $-(C_{0-3}$ alkylene)-$(C_{1-5}$ haloalkyl), $-(C_{0-3}$ alkylene)-O$-(C_{1-5}$ haloalkyl), alkylene)-CF$_3$, $-(C_{0-3}$ alkylene)-CN, $-(C_{0-3}$ alkylene)-NO$_2$, $-(C_{0-3}$ alkylene)-CHO, $-(C_{0-3}$ alkylene)-CO$-(C_{1-5}$ alkyl), $-(C_{0-3}$ alkylene)-COOH, $-(C_{0-3}$ alkylene)-CO$-$O$-(C_{1-5}$ alkyl), $-(C_{0-3}$ alkylene)-O$-$CO$-(C_{1-5}$ alkyl), $-(C_{0-3}$ alkylene)-CO$-$NH$_2$, $-(C_{0-3}$ alkylene)-CO$-$NH$(C_{1-5}$ alkyl), $-(C_{0-3}$ alkylene)-CO$-$N$(C_{1-5}$ alkyl)$(C_{1-5}$ alkyl), $-(C_{0-3}$ alkylene)-NH$-$CO$-(C_{1-5}$ alkyl), $-(C_{0-3}$ alkylene)-N$(C_{1-5}$ alkyl)-CO$-(C_{1-5}$ alkyl), $-(C_{0-3}$ alkylene)-SO$_2$$-$NH$_2$, $-(C_{0-3}$ alkylene)-SO$_2$$-$NH$(C_{1-5}$ alkyl), $-(C_{0-3}$ alkylene)-SO$_2$$-$N$(C_{1-5}$ alkyl)$(C_{1-5}$ alkyl), $-(C_{0-3}$ alkylene)-NH$-$SO$_2$$-(C_{1-5}$ alkyl), —(C$_{0-3}$ alkylene)-N(C$_{1-5}$ alkyl)-SO$_2$—(C$_{1-5}$ alkyl), —(C$_{0-3}$ alkylene)-cycloalkyl, —(C$_{0-3}$ alkylene)-O-cycloalkyl, —(C$_{0-3}$ alkylene)-O(C$_{1-5}$ alkylene)-cycloalkyl, —(C$_{0-3}$ alkylene)-heterocycloalkyl, —(C$_{0-3}$ alkylene)-O-heterocycloalkyl, and —(C$_{0-3}$ alkylene)-O(C$_{1-5}$ alkylene)-heterocycloalkyl.

L is selected from —CO—N(R$^{L1}$)—, —N(R$^{L1}$)—CO—, —CO—O—, —O—CO—, —C(=N—R$^{L2}$)—N(R$^{L1}$)—, —N(R$^{L1}$)—C(=N—R$^{L2}$)—, —C(=S)—N(R$^{L1}$)—, —N(R$^{L1}$)—C(=S)—, —N(R$^{L1}$)—CO—N(R$^{L1}$)—, —N(R$^{L1}$)—CO—O—, —N(R$^{L1}$)—C(=N—R$^{L2}$)—N(R$^{L1}$)—, —O—C(=N—R$^{L2}$)—N(R$^{L1}$)—, —N(R$^{L1}$)—C(=N—R$^{L2}$)—O—, —S—C(=N—R$^{L2}$)—N(R$^{L1}$)—, —N(R$^{L1}$)—C(=S)—N(R$^{L1}$)—, —O—C(=S)—N(R$^{L1}$)—, —N(R$^{L1}$)—C(=S)—O—, —S—CO—N(R$^{L1}$)—, and —N(R$^{L1}$)—CO—S—.

Each R$^{L1}$ is independently selected from hydrogen and C$_{1-5}$ alkyl.

Each R$^{L2}$ is independently selected from hydrogen, C$_{1-5}$ alkyl, —CN, and —NO$_2$.

n is 0 or 1.
m is 0 or 1.

The present invention also provides a pharmaceutical composition comprising a compound of formula (I), as described and defined herein, or a pharmaceutically acceptable salt, solvate or prodrug thereof, in combination with a pharmaceutically acceptable excipient.

Moreover, the invention relates to the use of a compound of formula (I) or a pharmaceutically acceptable salt, solvate or prodrug thereof in the preparation of a medicament, particularly for the treatment or prevention of a disease/disorder such as, e.g., cancer.

The compounds of formula (I) have been found to be potent inhibitors of TAF1, specifically of the second bromodomain of TAF1, as also demonstrated in the appended examples, and can thus be used for the treatment or prevention of cancer, particularly BRD4-driven cancer and/or c-MYC-driven cancer, as well as other diseases/disorders associated with TAF1 and/or BRD4.

The present invention thus particularly relates to a compound of formula (I), as described and defined herein, or a pharmaceutically acceptable salt, solvate or prodrug thereof, for use in the treatment or prevention of cancer.

The invention also provides a pharmaceutical composition comprising a compound of formula (I) or a pharmaceutically acceptable salt, solvate or prodrug thereof, in combination with a pharmaceutically acceptable excipient, for use in the treatment or prevention of cancer.

The present invention furthermore relates to the use of a compound of formula (I) or a pharmaceutically acceptable salt, solvate or prodrug thereof in the preparation of a medicament for the treatment or prevention of cancer.

The invention likewise provides a method of treating or preventing cancer, the method comprising administering a compound of formula (I) or a pharmaceutically acceptable salt, solvate or prodrug thereof, or a pharmaceutical composition comprising any of the aforementioned entities and a pharmaceutically acceptable excipient, to a subject (e.g., a human) in need thereof.

Moreover, the present invention relates to a compound of formula (I) or a pharmaceutically acceptable salt, solvate or prodrug thereof, or a pharmaceutical composition comprising any of the aforementioned entities and a pharmaceutically acceptable excipient, for use in inhibiting TAF1 or for use in treating or preventing cancer by inhibiting TAF1. The invention further refers to the use of a compound of formula (I) or a pharmaceutically acceptable salt, solvate or prodrug thereof in the preparation of a medicament for inhibiting TAF1 or for treating or preventing cancer by inhibiting TAF1. In addition thereto, the invention provides a method of inhibiting TAF1 in a subject, the method comprising administering a compound of formula (I) or a pharmaceutically acceptable salt, solvate or prodrug thereof, or a pharmaceutical composition comprising any of the aforementioned entities and a pharmaceutically acceptable excipient, to a subject (e.g., a human) in need thereof. The invention also provides a method of treating or preventing cancer by inhibiting TAF1, the method comprising administering a compound of formula (I) or a pharmaceutically acceptable salt, solvate or prodrug thereof, or a pharmaceutical composition comprising any of the aforementioned entities and a pharmaceutically acceptable excipient, to a subject (e.g., a human) in need thereof.

The invention further provides novel compounds embraced by formula (I), particularly the compounds 1, 3, 4, 5, 6, 8, 10, 12, 13, 15, 16, 24, 25, 26, 27, 29, 30, 33, 36, 37, 38 and 39 (as shown further below) as well as pharmaceutically acceptable salts, solvates and prodrugs of any of these compounds.

The present invention also relates to a TAF1 inhibitor (which is preferably a compound of formula (I) or a pharmaceutically acceptable salt, solvate or prodrug thereof) for use in therapy, particularly for use in the treatment or prevention of cancer, wherein the TAF1 inhibitor is to be administered in combination with a BRD4 inhibitor. The invention likewise relates to a BRD4 inhibitor for use in therapy, particularly for use in the treatment or prevention of cancer, wherein the BRD4 inhibitor is to be administered in combination with a TAF1 inhibitor. Moreover, the invention provides a pharmaceutical composition comprising a TAF1 inhibitor and a BRD4 inhibitor, and its use in therapy, particularly for use in the treatment or prevention of cancer. The invention further provides a method of treating or preventing cancer, the method comprising administering a TAF1 inhibitor in combination with a BRD4 inhibitor to a subject (e.g., a human) in need thereof. The TAF1 inhibitor is preferably a compound of formula (I) or a pharmaceutically acceptable salt, solvate or prodrug thereof, as described and defined herein. The BRD4 inhibitor is preferably a direct BRD4 inhibitor and may be, e.g., the compound CeMMEC2 shown below, or a pharmaceutically acceptable salt, solvate or prodrug thereof, or any one of the compounds JQ1 (also referred to as (S)-JQ1), I-BET 151 (or GSK1210151A), I-BET 762 (or GSK525762), PF-1, bromosporine, OTX-015, TEN-010, CPI-203, CPI-0610, RVX-208, BI2536, TG101348, LY294002, or a pharmaceutically acceptable salt, solvate or prodrug of any of these agents, or any one of the compounds disclosed in WO 2012/174487, WO 2014/076146, US 2014/0135336, WO 2014/134583, WO 2014/191894, WO 2014/191896, US 2014/0349990, or WO 2014/191906.

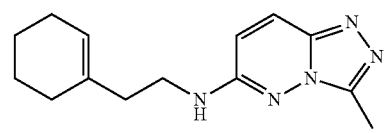

CeMMEC2

-continued

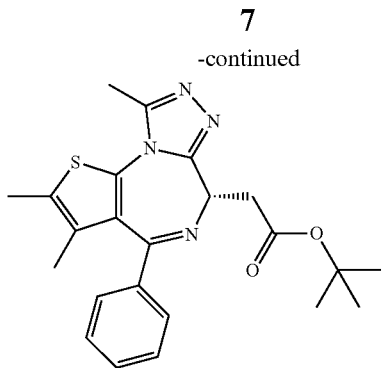
(S)-JQ1

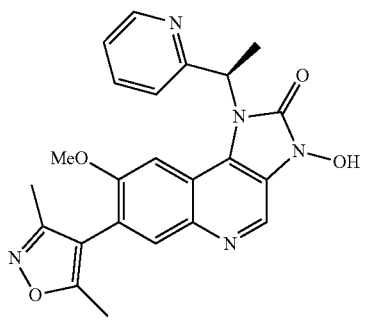
IBET-151

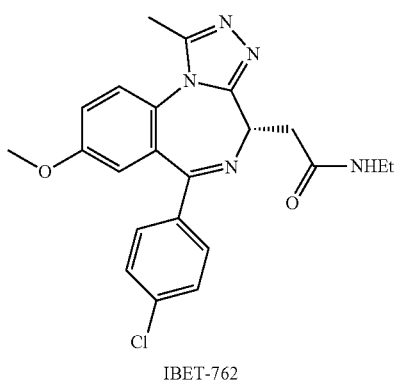
IBET-762

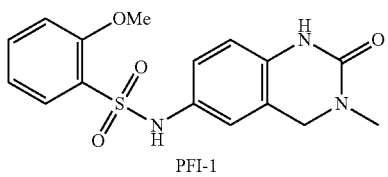
PFI-1

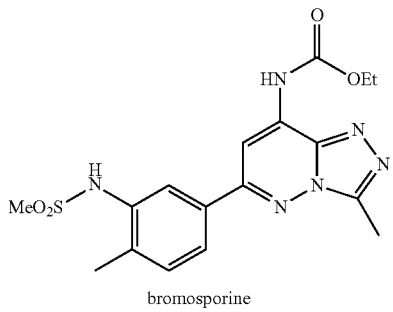
bromosporine

-continued

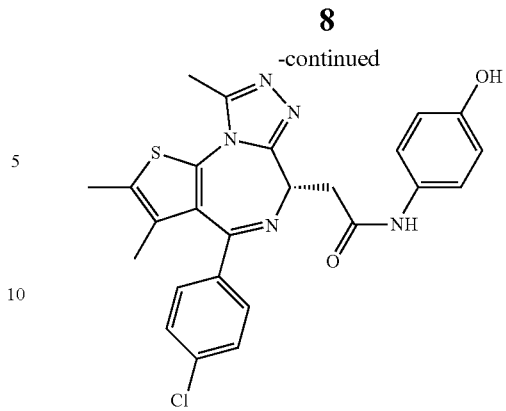
OTX015

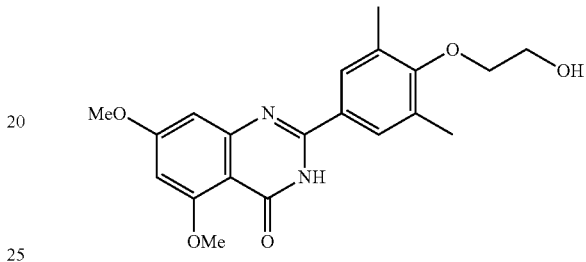
RVX208

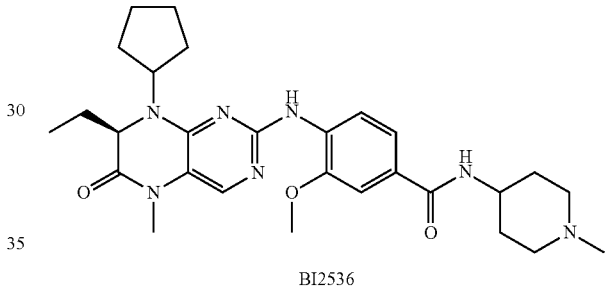
BI2536

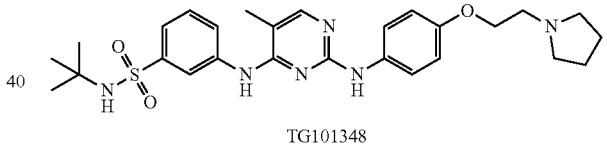
TG101348

The invention furthermore relates to the compound CeM-MEC2 or a pharmaceutically acceptable salt, solvate or prodrug thereof, or a pharmaceutical composition comprising any of the aforementioned entities and a pharmaceutically acceptable excipient, for use in therapy, particularly for use in the treatment or prevention of cancer (including any one of the specific types of cancer referred to herein). The invention also refers to each one of the compounds depicted in FIG. 11, particularly CeMMEC3, CeMMEC4, CeMMEC5, CeMMEC6, CeMMEC7, CeMMEC8, CeMMEC9, CeMMEC10, CeMMEC11, CeMMEC12, or a pharmaceutically acceptable salt, solvate or prodrug of any of these compounds, or a pharmaceutical composition comprising any of the aforementioned entities and a pharmaceutically acceptable excipient, for use in therapy, particularly as functional BRD4 inhibitors, and particularly for use in the treatment or prevention of cancer.

The present invention relates to the treatment or prevention of cancer, particularly BRD4-dependent cancer and/or c-MYC-dependent cancer, using a compound of formula (I) as described and defined herein, optionally in combination with a BRD4 inhibitor (such as, e.g., CeMMEC2). The cancer to be treated or prevented in accordance with the invention is preferably selected from prostate carcinoma, breast cancer, acute myeloid leukemia, multiple myeloma, glioblastoma, and NUT midline carcinoma.

The present invention furthermore relates to the use of a compound of formula (I) or a pharmaceutically acceptable salt, solvate or prodrug thereof as a TAF1 inhibitor in research, particularly as a research tool compound. Accordingly, the invention refers to the in vitro use of a compound of formula (I) or a pharmaceutically acceptable salt, solvate or prodrug thereof as a TAF1 inhibitor and, in particular, to the in vitro use of a compound of formula (I) or a pharmaceutically acceptable salt, solvate or prodrug thereof as a research tool compound acting as a TAF1 inhibitor. It is to be understood that the term "in vitro" is used in this specific context in the sense of "outside a living human or animal body", which includes, in particular, experiments performed with cells, cellular or subcellular extracts, and/or biological molecules in an artificial environment such as an aqueous solution or a culture medium which may be provided, e.g., in a flask, a test tube, a Petri dish, a microtiter plate, etc. The invention likewise relates to an in vitro method of inhibiting TAF1, comprising the use of a compound of formula (I) or a pharmaceutically acceptable salt, solvate or prodrug thereof as a TAF1 inhibitor. The present invention further provides a method (particularly an in vitro method) of inhibiting TAF1 in a sample, the method comprising applying a compound of formula (I) or a pharmaceutically acceptable salt, solvate or prodrug thereof to the sample.

The compound of formula (I) will be described in more detail in the following.

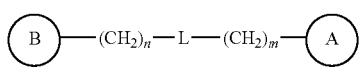
(I)

In formula (I), ring B is a group having the following structure:

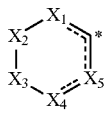

In ring B, one of the ring atoms $X_2$ and $X_3$ is $N(R^{X1})$, and the other one of said ring atoms $X_2$ and $X_3$ is $C(=O)$.

Preferably, $X_2$ is $C(=O)$, and $X_3$ is $N(R^{X1})$.

The ring atom $X_1$ is selected from $N(R^{X1})$, $C(R^{X2})$ and $C(=O)$, and the ring atoms $X_4$ and $X_5$ are each independently selected from $N(R^{X1})$, $C(R^{X3})$ and $C(=O)$, wherein at least one of said ring atoms $X_1$, $X_4$, and $X_5$ is different from $N(R^{X1})$ and $C(=O)$. The requirement that at least one of the ring atoms $X_1$, $X_4$, and $X_5$ is different from $N(R^{X1})$ and $C(=O)$ can also be expressed as a requirement that at least one of these ring atoms must be $C(R^{X2})$ or $C(R^{X3})$.

Preferably, not more than one (if any) of the ring atoms $X_1$, $X_4$, and $X_5$ is $N(R^{X1})$, and not more than one (if any) of said ring atoms $X_1$, $X_4$, and $X_5$ is $C(=O)$. More preferably, the ring atom $X_1$ is $C(R^{X2})$, and the ring atoms $X_4$ and $X_5$ are each $C(R^{X3})$.

In the compounds of formula (I), if $X_3$ and $X_5$ are $C(=O)$, $X_4$ is $N(R^{X1})$, and $X_1$ is $C(R^{X2})$, then $X_2$ is $N(H)$.

Each ===== is independently a single bond or a double bond, wherein at least one of any two adjacent bonds ===== is a single bond (i.e., at least one of any two bonds ===== that are attached to the same ring atom is a single bond).

Preferably, at least one of the bonds ===== in formula (I) is a double bond. More preferably, the bond ===== between the ring atom $X_1$ and the ring carbon atom which is bound to the moiety —$(CH_2)_n$-L-$(CH_2)_m$— is a double bond, the bond ===== between said ring carbon atom which is bound to the moiety —$(CH_2)_n$-L-$(CH_2)_m$— and the ring atom $X_5$ is a single bond, and the bond ===== between the ring atoms $X_4$ and $X_5$ is a single bond or a double bond (preferably a double bond).

It is particularly preferred that the ring atom $X_1$ is $C(R^{X2})$, the ring atoms $X_4$ and $X_5$ are each $C(R^{X3})$, the bond ===== between the ring atom $X_1$ and the ring carbon atom which is bound to the moiety —$(CH_2)_n$-L-$(CH_2)_m$— is a double bond, the bond ===== between said ring carbon atom which is bound to the moiety —$(CH_2)_n$-L-$(CH_2)_m$— and the ring atom $X_5$ is a single bond, and the bond ===== between the ring atoms $X_4$ and $X_5$ is a double bond.

Accordingly, it is particularly preferred that ring B has the following structure:

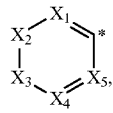

wherein the ring atom $X_1$ is $C(R^{X2})$, and the ring atoms $X_4$ and $X_5$ are each $C(R^{X3})$.

Each $R^{X1}$ is independently selected from hydrogen, $C_{1-5}$ alkyl, —CO($C_{1-5}$ alkyl), —($C_{0-3}$ alkylene)-aryl, and —($C_{0-3}$ alkylene)-heteroaryl, wherein the aryl comprised in said —($C_{0-3}$ alkylene)-aryl and the heteroaryl comprised in said —($C_{0-3}$ alkylene)-heteroaryl are each optionally substituted with one or more (e.g., one, two, or three) groups $R^{X11}$.

Preferably, each $R^{X1}$ is independently selected from hydrogen, $C_{1-5}$ alkyl, —($C_{0-3}$ alkylene)-aryl, and —($C_{0-3}$ alkylene)-heteroaryl, wherein the aryl comprised in said —($C_{0-3}$ alkylene)-aryl and the heteroaryl comprised in said —($C_{0-3}$ alkylene)-heteroaryl are each optionally substituted with one or more (e.g., one, two, or three) groups $R^{X11}$. More preferably, each $R^{X1}$ is independently selected from hydrogen, $C_{1-5}$ alkyl, and —($C_{0-3}$ alkylene)-phenyl, wherein the phenyl comprised in said —($C_{0-3}$ alkylene)-phenyl is optionally substituted with one or more (e.g., one, two, or three) groups R. Even more preferably, each $R^{X1}$ is independently selected from hydrogen and $C_{1-5}$ alkyl. Yet even more preferably, each $R^{X1}$ is independently selected from hydrogen, methyl and ethyl. Still more preferably, each $R^{X1}$ is independently selected from methyl and ethyl. Most preferably, each $R^{X1}$ is methyl.

$R^{X2}$ is selected from hydrogen, $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), and —($C_{0-3}$ alkylene)-N($C_{1-5}$ alkyl)-$SO_2$—($C_{1-5}$ alkyl).

Preferably, $R^{X2}$ is selected from hydrogen, $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —$CF_3$, —CN, —$NO_2$, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), and —N($C_{1-5}$ alkyl)-$SO_2$—($C_{1-5}$ alkyl). More preferably, $R^{X2}$ is selected from hydrogen, $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —$CF_3$, and —CN. Even more preferably, $R^{X2}$ is selected from hydrogen, $C_{1-4}$ alkyl, —OH, —O($C_{1-4}$ alkyl), —$NH_2$, —NH($C_{1-4}$ alkyl), —N($C_{1-4}$ alkyl)($C_{1-4}$ alkyl), halogen, —$CF_3$, and —CN. Most preferably, $R^{X2}$ is hydrogen.

The two groups $R^{X3}$ (which are present if $X^4$ and $X^5$ are each C($R^{X3}$)) are either mutually linked (i.e., joined) to form, together with the ring carbon atoms that they are attached to (i.e., the ring carbon atoms in positions $X^4$ and $X^5$), a 5- or 6-membered cyclyl group which is optionally substituted with one or more (e.g., one, two, or three) groups $R^{X31}$, or the two groups $R^{X3}$ are each independently selected from hydrogen, $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —$CF_3$, —CN, —$NO_2$, —CHO, —CO—($C_{1-5}$ alkyl), —COOH, —CO—O—($C_{1-5}$ alkyl), —O—CO—($C_{1-5}$alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), and —N($C_{1-5}$ alkyl)-$SO_2$—($C_{1-5}$ alkyl). It is preferred that the two groups $R^{X3}$ are mutually linked.

If the two groups $R^{X3}$ are not mutually linked, it is preferred that they are each independently selected from hydrogen, $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —$CF_3$, —CN, —$NO_2$, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), and —N($C_{1-5}$ alkyl)-$SO_2$—($C_{1-5}$ alkyl), more preferably from hydrogen, $C_{1-5}$ alkyl, $C_{2-5}$ alkenyl, $C_{2-5}$ alkynyl, —OH, —O($C_{1-5}$ alkyl), —O($C_{1-5}$ alkylene)-OH, alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —$CF_3$, and —CN, and even more preferably from hydrogen, $C_{1-4}$ alkyl, —OH, —O($C_{1-4}$ alkyl), —$NH_2$, —NH($C_{1-4}$ alkyl), —N($C_{1-4}$ alkyl)($C_{1-4}$ alkyl), halogen, —$CF_3$, and —CN.

If the two groups $R^{X3}$ are mutually linked to form, together with the ring carbon atoms that they are attached to, a 5- or 6-membered cyclyl group which is optionally substituted with one or more groups $R^{X31}$, it is preferred that said cyclyl group is a 5- or 6-membered cycloalkyl group (e.g., cyclopentyl or cyclohexyl), a 5- or 6-membered cycloalkenyl group (e.g., cyclopentenyl, cyclopentadienyl, cyclohexenyl, or cyclohexadienyl), a phenyl group, a 5- or 6-membered heterocycloalkyl group, a 5- or 6-membered heterocycloalkenyl group, or a 5- or 6-membered heteroaryl group, wherein each one of the aforementioned groups is optionally substituted with one or more (e.g., one, two, or three) groups $R^{X31}$. More preferably, said cyclyl group is a 5- or 6-membered cycloalkyl group (e.g., cyclopentyl or cyclohexyl), a 5- or 6-membered cycloalkenyl group (e.g., cyclopentenyl, cyclopentadienyl, cyclohexenyl, or cyclohexadienyl), or a phenyl group, wherein each one of the aforementioned groups is optionally substituted with one or more (e.g., one, two, or three) groups $R^{X31}$. Even more preferably, said cyclyl group is a phenyl group, wherein said phenyl group is optionally substituted with one or more (e.g., one, two, or three) groups $R^{X31}$. It will be understood that the cyclyl group (including any of the aforementioned preferred cyclyl groups) is formed from the two groups $R^{X3}$ and the ring carbon atoms (in positions $X^4$ and $X^5$) that these groups $R^{X3}$ are attached to, i.e., the corresponding cyclyl group is fused to the ring containing the ring atoms $X^1$ to $X^5$.

It is particularly preferred that the two groups $R^{X3}$ are mutually linked to form, together with the ring carbon atoms that they are attached to, a 5- or 6-membered cycloalkyl group, a 5- or 6-membered cycloalkenyl group, or a phenyl group, wherein said cycloalkyl group, said cycloalkenyl group, and said phenyl group are each optionally substituted with one or more (e.g., one, two, or three) groups $R^{X31}$. It is even more preferred that the ring atoms $X^4$ and $X^5$ are each C($R^{X3}$) and are connected by a double bond, thus forming a moiety —C($R^{X3}$)=C($R^{X3}$)—, and that the two groups $R^{X3}$ are mutually linked to form, together with the ring carbon atoms that they are attached to, a cyclopentenyl group, a cyclohexenyl group, or a phenyl group, wherein said cyclopentenyl group, said cyclohexenyl group, and said phenyl group are each optionally substituted with one or more (e.g., one, two, or three) groups $R^{X31}$. It is still more preferred that the ring atoms $X^4$ and $X^5$ are each C($R^{X3}$) and are connected by a double bond, thus forming a moiety —C($R^{X3}$)=C($R^{X3}$)—, and that the two groups $R^{X3}$ are mutually linked to form, together with the ring carbon atoms that they are attached to, a phenyl group, wherein said phenyl group is optionally substituted with one or more (e.g., one, two, or three) groups $R^{X31}$.

Each $R^{X11}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-$CF_3$, —($C_{0-3}$ alkylene)-CN, —($C_{0-3}$ alkylene)-$NO_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—

CO—($C_{1-5}$ alkyl), —($C_{0-3}$ alkylene)-N($C_{1-5}$ alkyl)-CO—($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), and —($C_{0-3}$ alkylene)-N($C_{1-5}$ alkyl)-$SO_2$—($C_{1-5}$ alkyl).

Preferably, each $R^{X11}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, haloalkyl), —$CF_3$, —CN, —$NO_2$, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-z}$ alkyl), and —N($C_{1-5}$ alkyl)-$SO_2$—($C_{1-z}$ alkyl). More preferably, each $R^{X11}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —$CF_3$, and —CN. Even more preferably, each $R^{X11}$ is independently selected from $C_{1-4}$ alkyl, —OH, —O($C_{1-4}$ alkyl), —$NH_2$, —NH($C_{1-4}$ alkyl), —N($C_{1-4}$ alkyl)($C_{1-4}$ alkyl), halogen, —$CF_3$, and —CN.

Each $R^{X31}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-$CF_3$, —($C_{0-3}$ alkylene)-CN, —($C_{0-3}$ alkylene)-$NO_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), and —($C_{0-3}$ alkylene)-N($C_{1-5}$ alkyl)-$SO_2$—($C_{1-5}$ alkyl).

Preferably, each $R^{X31}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —$CF_3$, —CN, —$NO_2$, —CHO, —CO—($C_{1-5}$ alkyl), —COOH, —CO—O—($C_{1-5}$ alkyl), —O—CO—($C_{1-z}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), and —N($C_{1-5}$ alkyl)-$SO_2$—($C_{1-5}$ alkyl). More preferably, each $R^{X31}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —$CF_3$, and —CN. Even more preferably, each $R^{X31}$ is independently selected from $C_{1-4}$ alkyl, —OH, —O($C_{1-4}$ alkyl), —$NH_2$, —NH($C_{1-4}$ alkyl), —N($C_{1-4}$ alkyl)($C_{1-4}$ alkyl), halogen, —$CF_3$, and —CN.

Ring B is attached to the remainder of the compound of formula (I), i.e. to the moiety —$(CH_2)_n$-L-$(CH_2)_m$— comprised in the compound of formula (I), via the ring carbon atom that is marked with an asterisk (*) or, if $X_4$ and $X_5$ are each $C(R^{X3})$ and the two groups $R^{X3}$ are mutually linked to form, together with the ring carbon atoms that they are attached to, a 5- or 6-membered cyclyl group (which is optionally substituted with one or more groups $R^{X31}$), then ring B may also be attached to the remainder of the compound of formula (I) via any ring carbon atom of said 5- or 6-membered cyclyl group.

If $X_4$ and $X_5$ are each $C(R^{X3})$ and the two groups $R^{X3}$ are mutually linked to form, together with the ring carbon atoms that they are attached to, a 6-membered cyclyl group (including any one of the specific or preferred 6-membered groups described herein, such as phenyl or cyclohexenyl) which is optionally substituted with one or more groups $R^{X31}$, then it is preferred that ring B is attached either via the ring carbon atom that is marked with an asterisk or via a ring carbon atom in the same position of the 6-membered cyclyl group as in compound 30.

It is particularly preferred that ring B is attached via the ring carbon atom that is marked with an asterisk (*). In this case, the compound of formula (I) has the following structure:

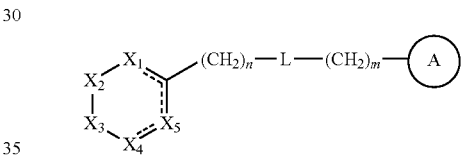

If $X_4$ and $X_5$ are each $C(R^{X3})$ and the two groups $R^{X3}$ are mutually linked to form, together with the ring carbon atoms that they are attached to, a 6-membered cyclyl group (including any one of the specific or preferred 6-membered groups described herein above, such as phenyl or cyclohexenyl) which is optionally substituted with one or more groups $R^{X31}$, then it is also particularly preferred that ring B is attached via a ring carbon atom in the same position of the 6-membered cyclyl group as in compound 30. Corresponding preferred examples of the compound of formula (I) are illustrated in the following:

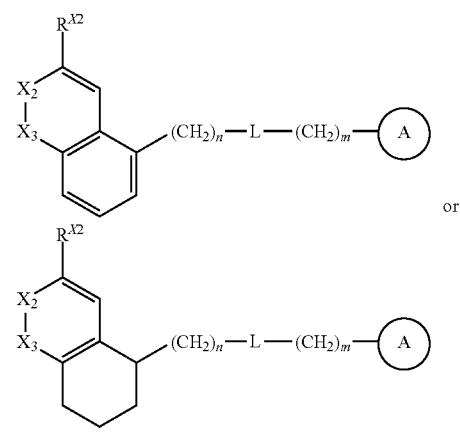

Ring A is aryl or heteroaryl, wherein said aryl and said heteroaryl are each optionally substituted with one or more (e.g., one, two, or three) groups $R^A$.

If ring A is aryl (which is optionally substituted with one or more groups $R^A$), it is preferred that said aryl is phenyl.

If ring A is heteroaryl (which is optionally substituted with one or more groups $R^A$), it is preferred that said heteroaryl is selected from the heteroaryl groups specified in the subsequent paragraph, more preferably from 1,4-benzodioxanyl (particularly 1,4-benzodioxan-6-yl), benzoxanyl (particularly 1-benzoxan-6-yl), 1,3-benzodioxolanyl (particularly 1,3-benzodioxolan-5-yl), benzoxolanyl (particularly 1-benzoxolan-5-yl), 1,5-benzodioxepanyl (particularly 1,5-benzodioxepan-7-yl), and benzoxepanyl (particularly 1-benzoxepan-7-yl), and is even more preferably selected from 1,4-benzodioxanyl (particularly 1,4-benzodioxan-6-yl), benzoxanyl (particularly 1-benzoxan-6-yl), 1,3-benzodioxolanyl (particularly 1,3-benzodioxolan-5-yl), benzoxolanyl (particularly 1-benzoxolan-5-yl), and 1,5-benzodioxepanyl (particularly 1,5-benzodioxepan-7-yl).

Preferably, ring A is selected from 1,4-benzodioxanyl (particularly 1,4-benzodioxan-6-yl), benzoxanyl (particularly 1-benzoxan-6-yl), 1,3-benzodioxolanyl (particularly 1,3-benzodioxolan-5-yl), benzoxolanyl (particularly 1-benzoxolan-5-yl), 1,5-benzodioxepanyl (particularly 1,5-benzodioxepan-7-yl), benzodioxepanyl (particularly 1-benzodioxepan-7-yl), phenyl, and a 5- or 6-membered monocyclic heteroaryl (such as, e.g., pyridinyl (particularly pyridin-3-yl) or oxadiazolyl (particularly 1,2,4-oxadiazolyl or 1,3,4-oxadiazolyl)), wherein each of the aforementioned groups is optionally substituted with one or more (e.g., one, two, or three) groups $R^A$. More preferably, ring A is selected from 1,4-benzodioxanyl (particularly 1,4-benzodioxan-6-yl), benzoxanyl (particularly 1-benzoxan-6-yl), 1,3-benzodioxolanyl (particularly 1,3-benzodioxolan-5-yl), benzoxolanyl (particularly 1-benzoxolan-5-yl), 1,5-benzodioxepanyl (particularly 1,5-benzodioxepan-7-yl), and phenyl, wherein each of the aforementioned groups is optionally substituted with one or more (e.g., one, two, or three) groups $R^A$. Even more preferably, ring A is selected from 1,4-benzodioxan-6-yl, 1-benzoxan-6-yl, and 4-($C_{1-5}$ alkoxy)-phenyl (particularly 4-methoxyphenyl), wherein the phenyl moiety comprised in said 1,4-benzodioxan-6-yl or in said 1-benzoxan-6-yl is optionally substituted with one or more (e.g., one or two) groups $R^A$. Yet even more preferably, ring A is selected from 1,4-benzodioxan-6-yl, 1-benzoxan-6-yl, and 4-methoxyphenyl.

Each $R^A$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), —($C_{0-3}$ alkylene)-N($C_{1-5}$ alkyl)-SO$_2$—($C_{1-5}$ alkyl), —($C_{0-3}$ alkylene)-cycloalkyl, —($C_{0-3}$ alkylene)-O-cycloalkyl, —($C_{0-3}$ alkylene)-O($C_{1-5}$ alkylene)-cycloalkyl, alkylene)-heterocycloalkyl, —($C_{0-3}$ alkylene)-O-heterocycloalkyl, and —($C_{0-3}$ alkylene)-O($C_{1-5}$ alkylene)-heterocycloalkyl.

Preferably, each $R^A$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —NO$_2$, —CHO, —CO—($C_{1-5}$ alkyl), —COOH, —CO—O—($C_{1-5}$ alkyl), —O—CO—($C_{1-5}$ alkyl), —CO—NH$_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —SO$_2$—NH$_2$, —SO$_2$—NH($C_{1-5}$ alkyl), —SO$_2$—N($C_{1-5}$ alkyl)($C_{1-5}$ alkyl), —NH—SO$_2$—($C_{1-5}$ alkyl), —N($C_{1-5}$ alkyl)-SO$_2$—($C_{1-5}$ alkyl), cycloalkyl, —O-cycloalkyl, —O—($C_{1-5}$ alkylene)-cycloalkyl, heterocycloalkyl, —O-heterocycloalkyl, and —O—($C_{1-5}$ alkylene)-heterocycloalkyl. More preferably, each $R^A$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —CF$_3$, and —CN. Even more preferably, each $R^A$ is independently selected from $C_{1-4}$ alkyl, —OH, —O($C_{1-4}$ alkyl) (particularly —OCH$_3$), —NH$_2$, —NH($C_{1-4}$ alkyl), —N($C_{1-4}$ alkyl)($C_{1-4}$ alkyl), halogen, —CF$_3$, and —CN.

L is selected from —CO—N($R^{L1}$)—, —N($R^{L1}$)—CO—, —CO—O—, —O—CO—, —C(=N—$R^{L2}$)—N($R^{L1}$)—, —N($R^{L1}$)—C(=N—$R^{L2}$)—, —C(=S)—N($R^{L1}$)—, —N($R^{L1}$)—C(=S)—, —N($R^{L1}$)—CO—N($R^{L1}$)—, —O—CO—N($R^{L1}$)—, —N($R^{L1}$)—CO—O—, —N($R^{L1}$)—C(=N—$R^{L2}$)—N($R^{L1}$)—, —O—C(=N—$R^{L2}$)—N($R^{L1}$)—, —N($R^{L1}$)—C(=N—$R^{L2}$)—O—, —S—C(=N—$R^{L2}$)—N($R^{L1}$)—, —N($R^{L1}$)—C(=N—$R^{L2}$)—S—, —N($R^{L1}$)—C(=S)—N($R^{L1}$)—, —O—C(=S)—N($R^{L1}$)—, —N($R^{L1}$)—C(=S)—O—, —S—CO—N($R^{L1}$)—, and —N($R^{L1}$)—CO—S—.

Preferably, L is selected from —CO—N($R^{L1}$)—, —N($R^{L1}$)—CO—, —CO—O—, —O—CO—, —N($R^{L1}$)—CO—N($R^{L1}$)—, —O—CO—N($R^{L1}$)—, and —N($R^{L1}$)—CO—O—. More preferably, L is selected from —CO—N($R^{L1}$)—, —N($R^{L1}$)—CO—, —CO—O—, and —O—CO—. Even more preferably, L is —CO—N(R")— or —N($R^{L1}$)—CO—;

accordingly, it is particularly preferred that the moiety —(CH$_2$)$_n$-L-(CH$_2$)$_m$— comprised in the compound of formula (I) is selected from —(CH$_2$)$_n$—CO—N($R^{L1}$)—(CH$_2$)$_m$— and —(CH$_2$)$_n$—N($R^{L1}$)—CO—(CH$_2$)$_m$—. Most preferably, L is —N($R^{L1}$)—CO—, wherein said —N($R^{L1}$)—CO— is bound via its —N($R^{L1}$)— group to the moiety —(CH$_2$)$_n$— comprised in the compound of formula (I), and wherein said —N($R^{L1}$)—CO— is bound via its —CO— group to the moiety —(CH$_2$)$_n$— comprised in the compound of formula (I); accordingly, it is most preferred that the moiety —(CH$_2$)$_n$-L-(CH$_2$)$_m$— comprised in the compound of formula (I) is —(CH$_2$)$_n$—N($R^{L1}$)—CO—(CH$_2$)$_m$—.

Each $R^{L1}$ is independently selected from hydrogen and $C_{1-5}$ alkyl. Preferably, each $R^{L1}$ is independently selected from hydrogen, methyl, and ethyl. More preferably, each $R^{L1}$ is hydrogen.

Each $R^{L2}$ is independently selected from hydrogen, $C_{1-5}$ alkyl, —CN, and —NO$_2$. Preferably, each $R^{L2}$ is independently selected from hydrogen, methyl, ethyl, —CN, and —NO$_2$. More preferably, each $R^{L2}$ is independently selected from hydrogen, methyl, ethyl, and —CN. Even more preferably, each $R^{L2}$ is independently selected from hydrogen, methyl, and ethyl.

n is 0 or 1. Preferably, n is 0.

m is 0 or 1. Preferably, m is 0.

It is to be understood that n indicates the number of methylene groups —$(CH_2)_n$— that are present between the group L and the ring containing the ring atoms $X_1$ to $X_5$. If n is 0, then group L is directly bound (i.e., bound via a covalent single bond) to the ring containing $X_1$ to $X_5$. Likewise, m indicates the number of methylene groups —$(CH_2)_m$— that are present between the group L and the ring group A. If m is 0, then group L is directly bound (i.e., bound via a covalent single bond) to the ring group A.

In accordance with the preferred meanings of L, $R^{L1}$, $R^{L2}$, m and n described above, it is particularly preferred that L is —CO—N($R^{L1}$)— or —N($R^{L1}$)—CO—, wherein $R^{L1}$ is selected from hydrogen, methyl, and ethyl, and that n and m are each 0. Still more preferably, L is —N($R^{L1}$)—CO—, wherein $R^{L1}$ is selected from hydrogen, methyl, and ethyl, and n and m are each 0. Most preferably, L is —NH—CO—, n is 0, and m is 0. Accordingly, it is most preferred that the moiety —$(CH_2)_n$-L-$(CH_2)_m$— comprised in the compound of formula (I) is —$(CH_2)_n$—NH—CO—$(CH_2)_m$—, wherein n and m are each 0.

The compound of formula (I) may be, for example, any one of the following compounds or a pharmaceutically acceptable salt, solvate or prodrug thereof:

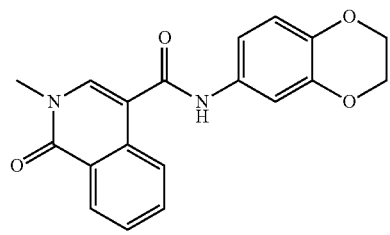

CeMMEC1

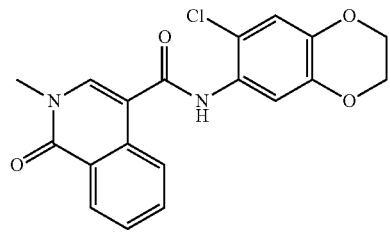

1

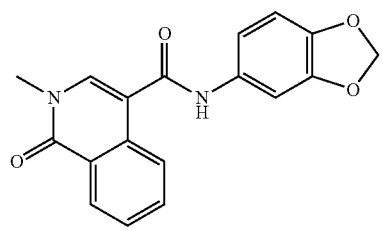

3

-continued

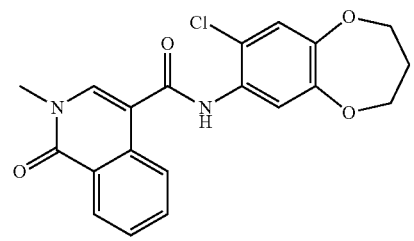

4

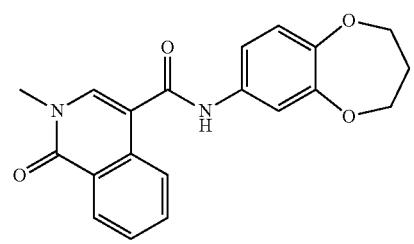

5

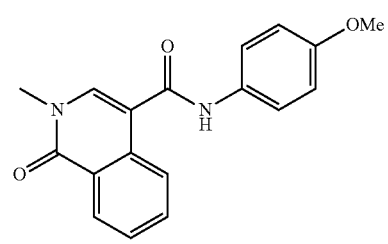

6

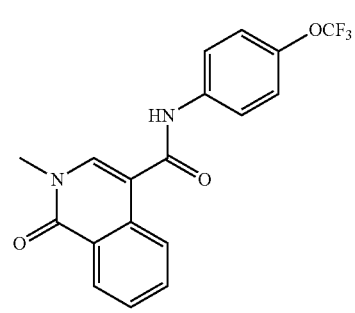

8

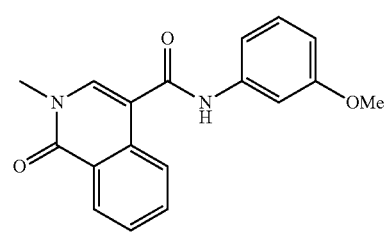

10

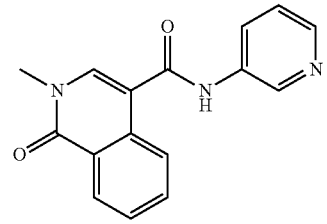

12

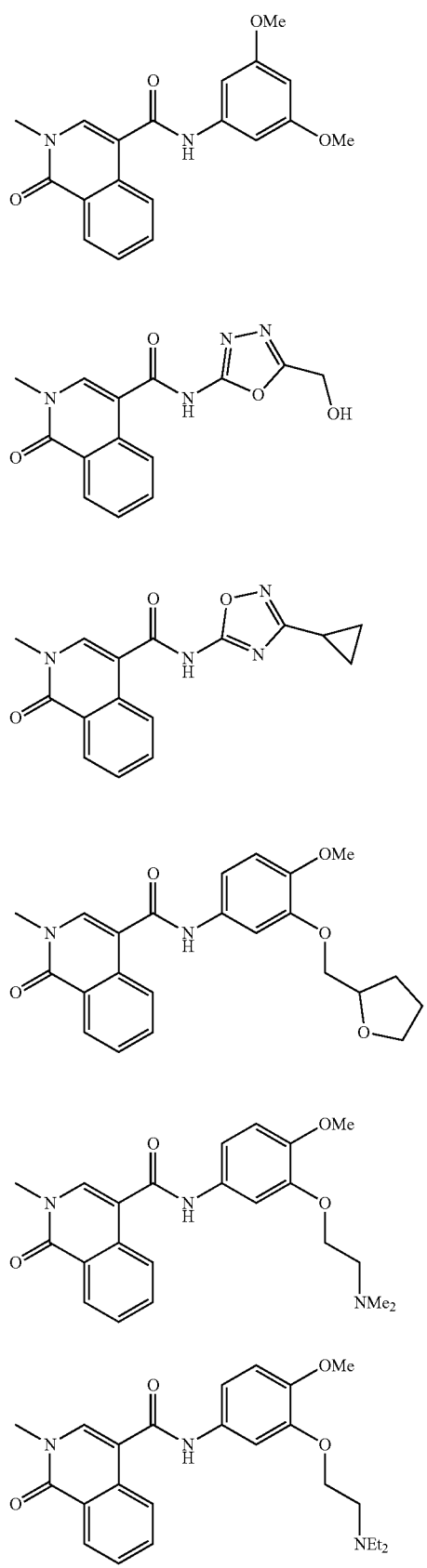
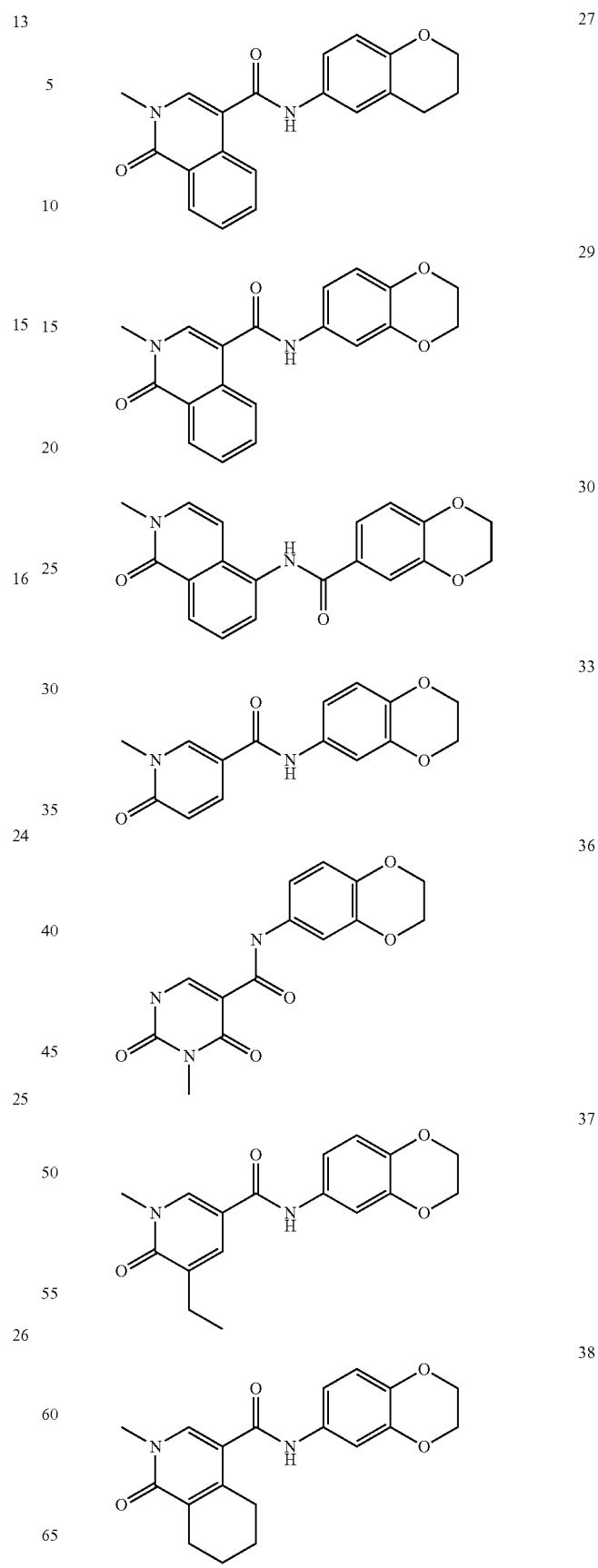

| | |
|---|---|
| 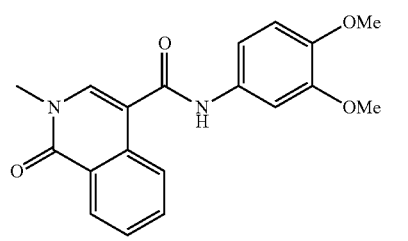 39 | 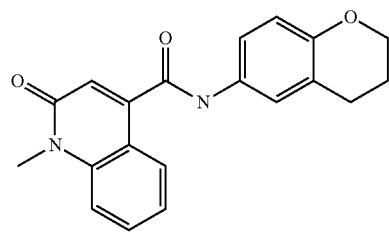 4-1 |
| 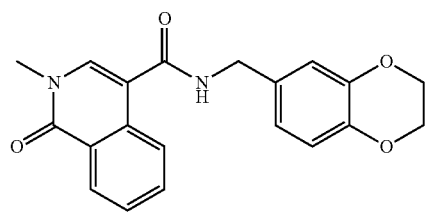 A1 | 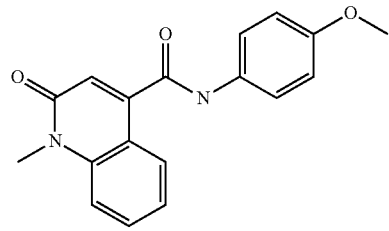 4-2 |
| 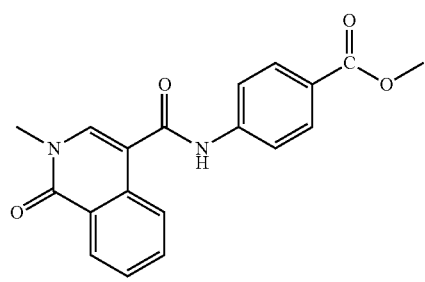 A2 | 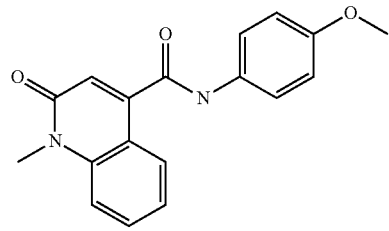 4-3 |
| 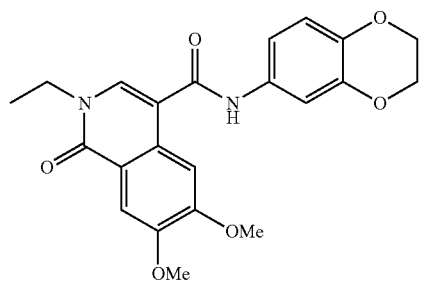 A3 | 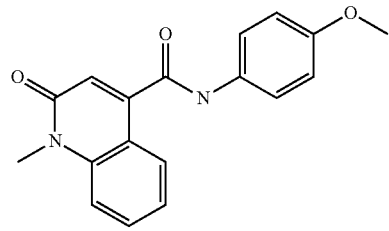 4-4 |
| 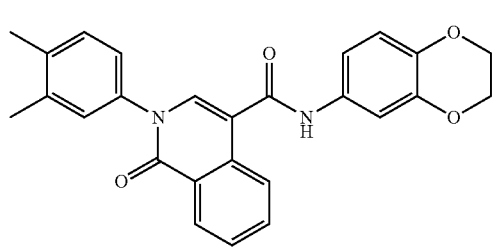 A4 | 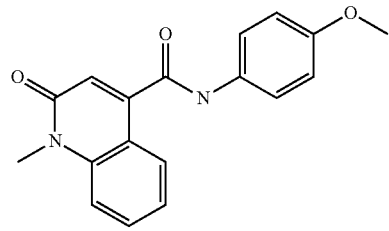 4-10 |
| 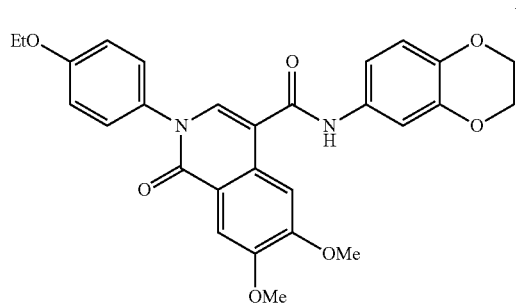 A5 | 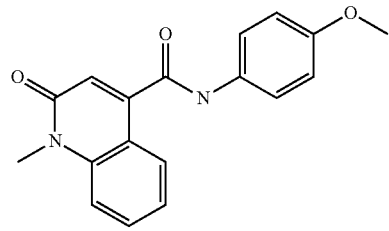 4-13 |
| | 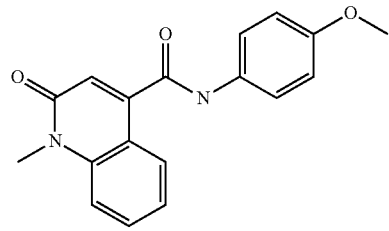 4-14 |

4-16 

4-17 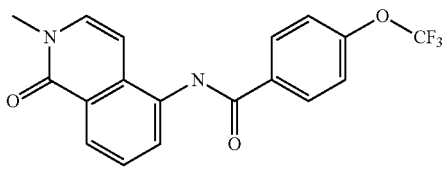

4-24 

4-25 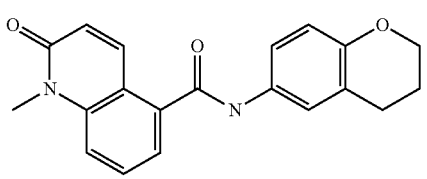

4-26 

4-28 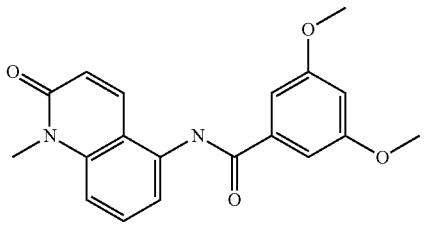

4-29 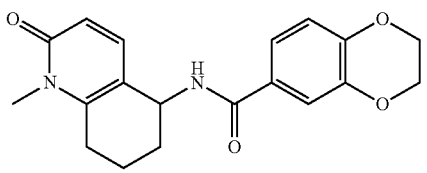

4-31 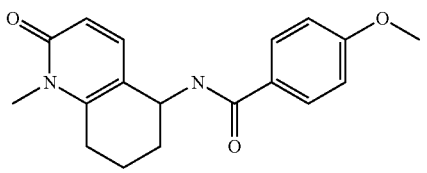

4-32 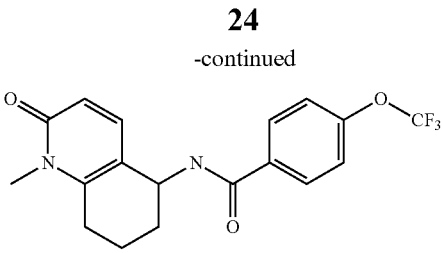

4-33 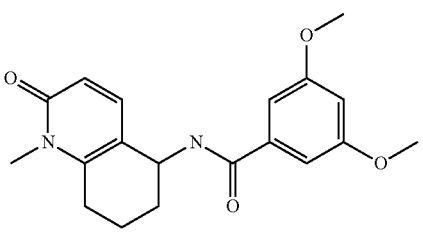

The above-depicted compounds 4-26, 4-1, 29, 30, CeM-MEC1, 38, 33, 37, A1, 27 and 6 as well as pharmaceutically acceptable salts, solvates and prodrugs thereof are particularly preferred examples of the compound of formula (I). The compounds 4-26, 4-1, 29 and 30 (particularly compound 4-26), and pharmaceutically acceptable salts, solvates and prodrugs thereof, are even more preferred.

It will be understood that in the above-depicted compounds 36, 4-1, 4-2, 4-3, 4-4, 4-10, 4-13, 4-14, 4-16, 4-17, 4-24, 4-25, 4-26, 4-28, 4-31, 4-32 and 4-33, the nitrogen atom in the linker group L (which is depicted as —N—), is substituted by a hydrogen atom (i.e., is present as —NH—).

In one embodiment of the compound of formula (I), $X_2$ is C(=O) and $X_3$ is N($R^{X1}$), the moiety —$(CH_2)_n$-L-$(CH_2)_m$— is —$(CH_2)_n$—CO—N($R^{L1}$)—$(CH_2)_m$—, and the further groups/variables comprised in formula (I) have the same meanings, including the same preferred meanings, as described and defined herein above.

In a further embodiment of the compound of formula (I), $X_2$ is C(=O) and $X_3$ is N($R^{X1}$), the moiety —$(CH_2)_n$-L-$(CH_2)_m$— is —$(CH_2)_n$—N($R^{L1}$)—CO—$(CH_2)_m$—, and the further groups/variables comprised in formula (I) have the same meanings, including the same preferred meanings, as described and defined herein above.

In a further embodiment of the compound of formula (I), $X_2$ is N($R^{X1}$) and $X_3$ is C(=O), the moiety —$(CH_2)_n$-L-$(CH_2)_m$— is —$(CH_2)_n$—CO—N($R^{L1}$)—$(CH_2)_m$—, and the further groups/variables comprised in formula (I) have the same meanings, including the same preferred meanings, as described and defined herein above.

In a further embodiment of the compound of formula (I), $X_2$ is N($R^{X1}$) and $X_3$ is C(=O), the moiety —$(CH_2)_n$-L-$(CH_2)_m$— is —$(CH_2)_n$—N($R^{L1}$)—CO—$(CH_2)_m$—, and the further groups/variables comprised in formula (I) have the same meanings, including the same preferred meanings, as described and defined herein above.

The compounds of formula (I) can be prepared by methods known in the field of synthetic chemistry. For example, these compounds can be prepared in accordance with or in analogy to the synthetic route described in Example 1.

The following definitions apply throughout the present specification, unless specifically indicated otherwise.

The term "hydrocarbon group" refers to a group consisting of carbon atoms and hydrogen atoms.

The term "alicyclic" is used in connection with cyclic groups and denotes that the corresponding cyclic group is non-aromatic.

As used herein, the term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. A "$C_{1-5}$ alkyl" denotes an alkyl group having 1 to 5 carbon atoms. Preferred exemplary alkyl groups are methyl, ethyl, propyl (e.g., n-propyl or isopropyl), or butyl (e.g., n-butyl, isobutyl, sec-butyl, or tert-butyl). Unless defined otherwise, the term "alkyl" preferably refers to $C_{1-4}$ alkyl, more preferably to methyl or ethyl, and even more preferably to methyl.

As used herein, the term "alkenyl" refers to a monovalent unsaturated acyclic hydrocarbon group which may be linear or branched and comprises one or more (e.g., one or two) carbon-to-carbon double bonds while it does not comprise any carbon-to-carbon triple bond. The term "$C_{2-5}$ alkenyl" denotes an alkenyl group having 2 to 5 carbon atoms. Preferred exemplary alkenyl groups are ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl). Unless defined otherwise, the term "alkenyl" preferably refers to $C_{2-4}$ alkenyl.

As used herein, the term "alkynyl" refers to a monovalent unsaturated acyclic hydrocarbon group which may be linear or branched and comprises one or more (e.g., one or two) carbon-to-carbon triple bonds and optionally one or more carbon-to-carbon double bonds. The term "$C_{2-5}$ alkynyl" denotes an alkynyl group having 2 to 5 carbon atoms. Preferred exemplary alkynyl groups are ethynyl, propynyl (e.g., propargyl), or butynyl. Unless defined otherwise, the term "alkynyl" preferably refers to $C_{2-4}$ alkynyl.

As used herein, the term "alkylene" refers to an alkanediyl group, i.e. a divalent saturated acyclic hydrocarbon group which may be linear or branched. A "$C_{1-5}$ alkylene" denotes an alkylene group having 1 to 5 carbon atoms, and the term "$C_{0-3}$ alkylene" indicates that a covalent bond (corresponding to the option "$C_0$ alkylene") or a $C_{1-3}$ alkylene is present. Preferred exemplary alkylene groups are methylene (—CH$_2$—), ethylene (e.g., —CH$_2$—CH$_2$— or —CH(—CH$_3$)—), propylene (e.g., —CH$_2$—CH$_2$—CH$_2$—, —CH(—CH$_2$—CH$_3$)—, —CH$_2$—CH(—CH$_3$)—, or —CH(—CH$_3$)—CH$_2$—), or butylene (e.g., —CH$_2$—CH$_2$—CH$_2$—CH$_2$—). Unless defined otherwise, the term "alkylene" preferably refers to $C_{1-4}$ alkylene (including, in particular, linear $C_{1-4}$ alkylene), more preferably to methylene or ethylene, and even more preferably to methylene.

As used herein, the term "alkoxy" refers to an —O-alkyl group, wherein the alkyl moiety comprised in this group is as defined above.

As used herein, the term "carbocyclyl" refers to a hydrocarbon ring group, including monocyclic rings as well as bridged ring, spiro ring and/or fused ring systems (which may be composed, e.g., of two or three rings), wherein said ring group may be saturated, partially unsaturated (i.e., unsaturated but not aromatic) or aromatic. Unless defined otherwise, "carbocyclyl" preferably refers to aryl, cycloalkyl or cycloalkenyl.

As used herein, the term "heterocyclyl" refers to a ring group, including monocyclic rings as well as bridged ring, Spiro ring and/or fused ring systems (which may be composed, e.g., of two or three rings), wherein said ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group may be saturated, partially unsaturated (i.e., unsaturated but not aromatic) or aromatic.

For example, each heteroatom-containing ring comprised in said ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. Unless defined otherwise, "heterocyclyl" preferably refers to heteroaryl, heterocycloalkyl or heterocycloalkenyl.

As used herein, the term "cyclyl" refers to a carbocyclyl or a heterocyclyl, as defined herein above.

As used herein, the term "aryl" refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). "Aryl" may, e.g., refer to phenyl, naphthyl, dialinyl (i.e., 1,2-dihydronaphthyl), tetralinyl (i.e., 1,2,3,4-tetrahydronaphthyl), indanyl, indenyl (e.g., 1H-indenyl), anthracenyl, phenanthrenyl, 9H-fluorenyl, or azulenyl. Unless defined otherwise, an "aryl" preferably has 6 to 14 ring atoms, more preferably 6 to 10 ring atoms, even more preferably refers to phenyl or naphthyl, and most preferably refers to phenyl.

As used herein, the term "heteroaryl" refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said aromatic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heteroaryl" may, e.g., refer to thienyl (i.e., thiophenyl), benzo[b]thienyl, naphtho[2,3-b]thienyl, thianthrenyl, furyl (i.e., furanyl), benzofuranyl, isobenzofuranyl, chromanyl, chromenyl (e.g., 2H-1-benzopyranyl or 4H-1-benzopyranyl), isochromenyl (e.g., 1H-2-benzopyranyl), chromonyl, xanthenyl, phenoxathiinyl, pyrrolyl (e.g., 1H-pyrrolyl), imidazolyl, pyrazolyl, pyridyl (i.e., pyridinyl; e.g., 2-pyridyl, 3-pyridyl, or 4-pyridyl), pyrazinyl, pyrimidinyl, pyridazinyl, indolyl (e.g., 3H-indolyl), isoindolyl, indazolyl, indolizinyl, purinyl, quinolyl, isoquinolyl, phthalazinyl, naphthyridinyl, quinoxalinyl, cinnolinyl, pteridinyl, carbazolyl, β-carbolinyl, phenanthridinyl, acridinyl, perimidinyl, phenanthrolinyl (e.g.,

[1,10]phenanthrolinyl, [1,7]phenanthrolinyl, or [4,7] phenanthrolinyl), phenazinyl, thiazolyl, isothiazolyl, phenothiazinyl, oxazolyl, isoxazolyl, oxadiazolyl (e.g., 1,2,4-oxadiazolyl, 1,2,5-oxadiazolyl (i.e., furazanyl), or 1,3,4-oxadiazolyl), thiadiazolyl (e.g., 1,2,4-thiadiazolyl, 1,2,5-thiadiazolyl, or 1,3,4-thiadiazolyl), phenoxazinyl, pyrazolo[1,5-a]pyrimidinyl (e.g., pyrazolo[1,5-a]pyrimidin-3-yl), 1,2-benzoisoxazol-3-yl, benzothiazolyl, benzothiadiazolyl, benzoxazolyl, benzisoxazolyl, benzimidazolyl, benzo[b]thiophenyl (i.e., benzothienyl), triazolyl (e.g., 1H-1,2,3-triazolyl, 2H-1,2,3-triazolyl, 1H-1,2,4-triazolyl, or 4H-1,2,4-triazolyl), benzotriazolyl, 1H-tetrazolyl, 2H-tetrazolyl, triazinyl (e.g., 1,2,3-triazinyl, 1,2,4-triazinyl, or 1,3,5-triazinyl), furo[2,3-c]pyridinyl, dihydrofuropyridinyl (e.g., 2,3-dihydrofuro[2,3-c]pyridinyl or 1,3-dihydrofuro[3,4-c]pyridinyl), imidazopyridinyl (e.g., imidazo[1,2-a]pyridinyl or imidazo[3,2-a]pyridinyl), quinazolinyl, thienopyridinyl, tetrahydrothienopyridinyl (e.g., 4,5,6,7-tetrahydrothieno[3,2-c]pyridinyl), dibenzofuranyl, 1,3-benzodioxolyl, benzodioxanyl (e.g., 1,3-benzodioxanyl or 1,4-benzodioxanyl), or coumarinyl. Unless defined otherwise, the term "heteroaryl" preferably refers to a 5 to 14 membered (more preferably 5 to 10 membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized; even more preferably, a "heteroaryl" refers to a 5 or 6 membered monocyclic ring comprising one or more (e.g., one, two or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, the term "heteroaryl" particularly preferably refers to pyridinyl (e.g., 2-pyridyl, 3-pyridyl, or 4-pyridyl), imidazolyl, thiazolyl, 1H-tetrazolyl, 2H-tetrazolyl, thienyl (i.e., thiophenyl), or pyrimidinyl.

As used herein, the term "cycloalkyl" refers to a saturated hydrocarbon ring group, including monocyclic rings as well as bridged ring, Spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, decalinyl (i.e., decahydronaphthyl), or adamantyl. Unless defined otherwise, "cycloalkyl" preferably refers to a $C_{3-11}$ cycloalkyl, and more preferably refers to a $C_{3-7}$ cycloalkyl. A particularly preferred "cycloalkyl" is a monocyclic saturated hydrocarbon ring having 3 to 7 ring members. Moreover, unless defined otherwise, the term "cycloalkyl" even more preferably refers to cyclohexyl or cyclopropyl, and yet even more preferably refers to cyclohexyl.

As used herein, the term "heterocycloalkyl" refers to a saturated ring group, including monocyclic rings as well as bridged ring, Spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said saturated ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkyl" may, e.g., refer to aziridinyl, azetidinyl, pyrrolidinyl, imidazolidinyl, pyrazolidinyl, piperidinyl, piperazinyl, azepanyl, diazepanyl (e.g., 1,4-diazepanyl), oxazolidinyl, isoxazolidinyl, thiazolidinyl, isothiazolidinyl, morpholinyl (e.g., morpholin-4-yl), thiomorpholinyl (e.g., thiomorpholin-4-yl), oxazepanyl, oxiranyl, oxetanyl, tetrahydrofuranyl, 1,3-dioxolanyl, tetrahydropyranyl, 1,4-dioxanyl, oxepanyl, thiiranyl, thietanyl, tetrahydrothiophenyl (i.e., thiolanyl), 1,3-dithiolanyl, thianyl, thiepanyl, decahydroquinolinyl, decahydroisoquinolinyl, or 2-oxa-5-aza-bicyclo[2.2.1]hept-5-yl. Unless defined otherwise, "heterocycloalkyl" preferably refers to a 3 to 11 membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized; more preferably, "heterocycloalkyl" refers to a 5 to 7 membered saturated monocyclic ring group containing one or more (e.g., one, two, or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, "heterocycloalkyl" even more preferably refers to tetrahydropyranyl, piperidinyl, piperazinyl, morpholinyl, pyrrolidinyl, or tetrahydrofuranyl.

As used herein, the term "cycloalkenyl" refers to an unsaturated alicyclic (non-aromatic) hydrocarbon ring group, including monocyclic rings as well as bridged ring, spiro ring and/or fused ring systems (which may be composed, e.g., of two or three rings; such as, e.g., a fused ring system composed of two or three fused rings), wherein said hydrocarbon ring group comprises one or more (e.g., one or two) carbon-to-carbon double bonds and does not comprise any carbon-to-carbon triple bond. "Cycloalkenyl" may, e.g., refer to cyclopropenyl, cyclobutenyl, cyclopentenyl, cyclohexenyl, cyclohexadienyl, cycloheptenyl, or cycloheptadienyl. Unless defined otherwise, "cycloalkenyl" preferably refers to a $C_{3-11}$ cycloalkenyl, and more preferably refers to a $C_{3-7}$ cycloalkenyl. A particularly preferred "cycloalkenyl" is a monocyclic unsaturated alicyclic hydrocarbon ring having 3 to 7 ring members and containing one or more (e.g., one or two; preferably one) carbon-to-carbon double bonds.

As used herein, the term "heterocycloalkenyl" refers to an unsaturated alicyclic (non-aromatic) ring group, including monocyclic rings as well as bridged ring, Spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group comprises at least one double bond between adjacent ring atoms and does not comprise any triple bond between adjacent ring atoms. For example, each heteroatom-containing ring comprised in said unsaturated alicyclic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkenyl" may, e.g., refer to imidazolinyl (e.g., 2-imidazolinyl (i.e., 4,5-dihydro-1H-imidazolyl), 3-imidazolinyl, or 4-imidazolinyl), tetrahydropyridinyl (e.g., 1,2,3,6-tetrahydropyridinyl), dihydropyridinyl (e.g., 1,2-dihydropyridinyl or 2,3-dihydropyridinyl), pyranyl (e.g., 2H-pyranyl or 4H-pyranyl), thiopyranyl (e.g., 2H-thiopyranyl or 4H-thiopyranyl), dihydropyranyl, dihydrofuranyl, dihydropyrazolyl, dihydropyrazinyl, dihydroisoindolyl, octahydroquinolinyl (e.g., 1,2,3,4,4a,5,6,7-octahydroquinolinyl), or octahydroisoquinolinyl (e.g., 1,2,3,4,5,6,7,8-octahydroisoquinolinyl). Unless defined otherwise, "heterocycloalkenyl" preferably refers to a 3 to 11 membered unsaturated alicyclic ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms; more preferably, "heterocycloalkenyl" refers to a 5 to 7 membered monocyclic unsaturated non-aromatic ring group containing one or more (e.g., one, two, or three) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms.

As used herein, the term "halogen" refers to fluoro (—F), chloro (—Cl), bromo (—Br), or iodo (—I).

As used herein, the term "haloalkyl" refers to an alkyl group substituted with one or more (preferably 1 to 6, more preferably 1 to 3) halogen atoms which are selected independently from fluoro, chloro, bromo and iodo, and are preferably all fluoro atoms. It will be understood that the maximum number of halogen atoms is limited by the number of available attachment sites and, thus, depends on the number of carbon atoms comprised in the alkyl moiety of the haloalkyl group. "Haloalkyl" may, e.g., refer to —CF$_3$, —CHF$_2$, —CH$_2$F, —CF$_2$—CH$_3$, —CH$_2$—CF$_3$, —CH$_2$—CHF$_2$, —CH$_2$—CF$_2$—CH$_3$, —CH$_2$—CF$_2$—CF$_3$, or —CH(CF$_3$)$_2$. A particularly preferred "haloalkyl" group is —CF$_3$.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

Various groups are referred to as being "optionally substituted" in this specification. Generally, these groups may carry one or more substituents, such as, e.g., one, two, three or four substituents. It will be understood that the maximum number of substituents is limited by the number of attachment sites available on the substituted moiety. Unless defined otherwise, the "optionally substituted" groups referred to in this specification carry preferably not more than two substituents and may, in particular, carry only one substituent. Moreover, unless defined otherwise, it is preferred that the optional substituents are absent, i.e. that the corresponding groups are unsubstituted.

A skilled person will appreciate that the substituent groups comprised in the compounds of formula (I) may be attached to the remainder of the respective compound via a number of different positions of the corresponding specific substituent group. Unless defined otherwise, the preferred attachment positions for the various specific substituent groups are as illustrated in the examples.

As used herein, unless explicitly indicated otherwise or contradicted by context, the terms "a", "an" and "the" are used interchangeably with "one or more" and "at least one". Thus, for example, a composition comprising "a" compound of formula (I) can be interpreted as referring to a composition comprising "one or more" compounds of formula (I).

As used herein, the term "comprising" (or "comprise", "comprises", "contain", "contains", or "containing"), unless explicitly indicated otherwise or contradicted by context, has the meaning of "containing, inter alia", i.e., "containing, among further optional elements, . . . ". In addition thereto, this term also includes the narrower meanings of "consisting essentially of" and "consisting of". For example, the term "A comprising B and C" has the meaning of "A containing, inter alia, B and C", wherein A may contain further optional elements (e.g., "A containing B, C and D" would also be encompassed), but this term also includes the meaning of "A consisting essentially of B and C" and the meaning of "A consisting of B and C" (i.e., no other components than B and C are comprised in A).

Moreover, unless indicated otherwise, any reference to an industry standard, a pharmacopeia, or a manufacturer's manual refers to the corresponding latest version that was available at the priority date (i.e., at the earliest filing date) of the present specification.

The scope of the invention embraces all pharmaceutically acceptable salt forms of the compounds provided herein, particularly the compounds of formula (I), which may be formed, e.g., by protonation of an atom carrying an electron lone pair which is susceptible to protonation, such as an amino group, with an inorganic or organic acid, or as a salt of an acid group (such as a carboxylic acid group) with a physiologically acceptable cation. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Exemplary acid addition salts comprise, for example: mineral acid salts such as hydrochloride, hydrobromide, hydroiodide, sulfate salts (such as, e.g., sulfate or hydrogensulfate salts), nitrate salts, phosphate salts (such as, e.g., phosphate, hydrogenphosphate, or dihydrogenphosphate salts), carbonate salts, hydrogencarbonate salts, perchlorate salts, borate salts, or thiocyanate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, adipate, gluconate, glycolate, nicotinate, benzoate, salicylate, ascorbate, pamoate (embonate), camphorate, glucoheptanoate, or pivalate salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthalenesulfonate (napsylate), 3-phenylsulfonate, or camphorsulfonate salts; glycerophosphate salts; and acidic amino acid salts such as aspartate or glutamate salts.

Moreover, the scope of the invention embraces the compounds provided herein, particularly the compounds of formula (I), in any solvated form, including, e.g., solvates with water (i.e., as a hydrate) or solvates with organic solvents such as, e.g., methanol, ethanol or acetonitrile (i.e., as a methanolate, ethanolate or acetonitrilate), or in any crystalline form (i.e., as any polymorph), or in amorphous form. It is to be understood that such solvates of the compounds provided herein, particularly the compounds of formula (I), also include solvates of pharmaceutically acceptable salts of the corresponding compounds.

Furthermore, the compounds provided herein, particularly the compounds of formula (I), may exist in the form of different isomers, in particular stereoisomers (including, e.g., geometric isomers (or cis/trans isomers), enantiomers and diastereomers) or tautomers. All such isomers of the compounds provided herein are contemplated as being part of the present invention, either in admixture or in pure or substantially pure form. As for stereoisomers, the invention embraces the isolated optical isomers of the compounds according to the invention as well as any mixtures thereof (including, in particular, racemic mixtures/racemates). The racemates can be resolved by physical methods, such as, e.g., fractional crystallization, separation or crystallization of diastereomeric derivatives, or separation by chiral column chromatography. The individual optical isomers can also be obtained from the racemates via salt formation with an optically active acid followed by crystallization. The present invention further encompasses any tautomers of the compounds provided herein.

The scope of the invention also embraces the compounds provided herein, particularly the compounds of formula (I), in which one or more atoms are replaced by a specific isotope of the corresponding atom. For example, the invention encompasses compounds of formula (I), in which one or more hydrogen atoms (or, e.g., all hydrogen atoms) are replaced by deuterium atoms (i.e., $^2$H; also referred to as "D"). Accordingly, the invention also embraces compounds of formula (I) which are enriched in deuterium. Naturally occurring hydrogen is an isotopic mixture comprising about 99.98 mol-% hydrogen-1 ($^1$H) and about 0.0156 mol-% deuterium ($^2$H or D). The content of deuterium in one or more hydrogen positions in the compounds of formula (I) can be increased using deuteration techniques known in the art. For example, a compound of formula (I) or a reactant or precursor to be used in the synthesis of the compound of formula (I) can be subjected to an H/D exchange reaction using, e.g., heavy water (D$_2$O). Further suitable deuteration techniques are described in: Atzrodt J et al., *Bioorg Med Chem*, 20(18), 5658-5667, 2012; William J S et al., *Journal of Labelled Compounds and Radiopharmaceuticals*, 53(11-12), 635-644, 2010; or Modvig A et al., *J Org Chem*, 79, 5861-5868, 2014. The content of deuterium can be determined, e.g., using mass spectrometry or NMR spectroscopy. Unless specifically indicated otherwise, it is preferred that the compound of formula (I) is not enriched in deuterium. Accordingly, the presence of naturally occurring hydrogen atoms or $^1$H hydrogen atoms in the compounds of formula (I) is preferred.

The present invention also embraces the compounds provided herein, particularly the compounds of formula (I), in which one or more atoms are replaced by a positron-emitting isotope of the corresponding atom, such as, e.g., $^{18}$F, $^{11}$C, $^{13}$N, $^{15}$O, $^{76}$Br, $^{77}$Br, $^{120}$I and/or $^{124}$I. Such compounds can be used as tracers or imaging probes in positron emission tomography (PET). The invention thus includes (i) compounds of formula (I), in which one or more fluorine atoms (or, e.g., all fluorine atoms) are replaced by $^{18}$F atoms, (ii) compounds of formula (I), in which one or more carbon atoms (or, e.g., all carbon atoms) are replaced by $^{11}$C atoms, (iii) compounds of formula (I), in which one or more nitrogen atoms (or, e.g., all nitrogen atoms) are replaced by $^{13}$N atoms, (iv) compounds of formula (I), in which one or more oxygen atoms (or, e.g., all oxygen atoms) are replaced by $^{15}$O atoms, (v) compounds of formula (I), in which one or more bromine atoms (or, e.g., all bromine atoms) are replaced by $^{76}$Br atoms, (vi) compounds of formula (I), in which one or more bromine atoms (or, e.g., all bromine atoms) are replaced by $^{77}$Br atoms, (vii) compounds of formula (I), in which one or more iodine atoms (or, e.g., all iodine atoms) are replaced by $^{120}$I atoms, and (viii) compounds of formula (I), in which one or more iodine atoms (or, e.g., all iodine atoms) are replaced by $^{124}$I atoms. In general, it is preferred that none of the atoms in the compounds of formula (I) are replaced by specific isotopes.

Pharmaceutically acceptable prodrugs of the compounds provided herein, particularly the compounds of formula (I), are derivatives which have chemically or metabolically cleavable groups and become, by solvolysis or under physiological conditions, the compounds of the invention which are pharmaceutically active in vivo. Prodrugs of the compounds according to the the present invention may be formed in a conventional manner with a functional group of the compounds such as, e.g., with an amino, hydroxy or carboxy group. The prodrug form often offers advantages in terms of solubility, tissue compatibility or delayed release in a mammalian organism (see, Bundgaard, H., Design of Prodrugs, pp. 7-9, 21-24, Elsevier, Amsterdam 1985). Prodrugs include acid derivatives, such as, e.g., esters prepared by reaction of the parent acidic compound with a suitable alcohol, or amides prepared by reaction of the parent acid compound with a suitable amine. If a compound of the present invention has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester, N,N-diethylglycolamidoester or α-acetoxyethylester. If a compound of the present invention has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—CH$_3$, —OC(=O)—C$_2$H$_5$, —OC(=O)-(tert-Bu), —OC(=O)—O$_{15}$H$_{31}$, —OC(=O)-(m-COONa-Ph), —OC(=O)—CH$_2$CH$_2$COONa, —O(C=O)—CH(NH$_2$)CH$_3$ or —OC(=O)—CH$_2$—N(CH$_3$)$_2$. If a compound of the present invention has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)$_2$OCH$_3$ or —NHC(=O)—CH(NH$_2$)CH$_3$.

The compounds provided herein, including in particular the compounds of formula (I), may be administered as compounds per se or may be formulated as medicaments. The medicaments/pharmaceutical compositions may optionally comprise one or more pharmaceutically acceptable excipients, such as carriers, diluents, fillers, disintegrants, lubricating agents, binders, colorants, pigments, stabilizers, preservatives, antioxidants, and/or solubility enhancers.

The pharmaceutical compositions may comprise one or more solubility enhancers, such as, e.g., poly(ethylene glycol), including poly(ethylene glycol) having a molecular weight in the range of about 200 to about 5,000 Da (e.g., PEG 200, PEG 300, PEG 400, or PEG 600), ethylene glycol, propylene glycol, glycerol, a non-ionic surfactant, tyloxapol, polysorbate 80, macrogol-15-hydroxystearate (e.g., Kolliphor® HS 15, CAS 70142-34-6), a phospholipid, lecithin, dimyristoyl phosphatidylcholine, dipalmitoyl phosphatidylcholine, distearoyl phosphatidylcholine, a cyclodextrin, α-cyclodextrin, β-cyclodextrin, γ-cyclodextrin, hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, sulfobutylether-β-cyclodextrin, sulfobutylether-γ-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, a carboxyalkyl thioether, hydroxypropyl methylcellulose, hydroxypropylcellulose, polyvinylpyrrolidone, a vinyl acetate copolymer, vinyl pyrrolidone, sodium lauryl sulfate, dioctyl sodium sulfosuccinate, or any combination thereof.

The pharmaceutical compositions can be formulated by techniques known to the person skilled in the art, such as the techniques published in "Remington: The Science and Practice of Pharmacy", Pharmaceutical Press, 22$^{nd}$ edition. The pharmaceutical compositions can be formulated as dosage forms for oral, parenteral, such as intramuscular, intravenous, subcutaneous, intradermal, intraarterial, intracardial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds provided herein, particularly the compounds of formula (I), or the above described pharmaceutical compositions comprising such a compound may be administered to a subject by any convenient route of administration, whether systemically/peripherally or at the site of desired action, including but not limited to one or more of: oral (e.g., as a tablet, capsule, or as an ingestible solution), topical (e.g., transdermal, intranasal, ocular, buccal, and sublingual), parenteral (e.g., using injection techniques or infusion techniques, and including, for example, by injection, e.g., subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g., through mouth or nose), gastrointestinal, intrauterine, intraocular, subcutaneous, ophthalmic (including intravitreal or intracameral), rectal, or vaginal administration.

If said compounds or pharmaceutical compositions are administered parenterally, then examples of such administration include one or more of: intravenously, intraarterially, intraperitoneally, intrathecally, intraventricularly, intraurethrally, intrasternally, intracardially, intracranially, intramuscularly or subcutaneously administering the compounds or pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Alternatively, said compounds or pharmaceutical compositions can be administered in the form of a suppository or pessary, or may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by sustained release systems. Suitable examples of sustained-release compositions include semipermeable polymer matrices in the form of shaped articles, e.g., films, or microcapsules. Sustained-release matrices include, e.g., polylactides (see, e.g., U.S. Pat. No. 3,773, 919), copolymers of L-glutamic acid and gamma-ethyl-L-glutamate (Sidman, U. et al., Biopolymers 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP133988). Sustained-release pharmaceutical compositions also include liposomally entrapped compounds. Liposomes containing a compound of the present invention can be prepared by methods known in the art, such as, e.g., the methods described in any one of: DE3218121; Epstein et al., Proc. Natl. Acad. Sci. (USA) 82:3688-3692 (1985); Hwang et al., Proc. Natl. Acad. Sci. (USA) 77:4030-4034 (1980); EP0052322; EP0036676; EP088046; EP0143949; EP0142641; JP 83-118008; U.S. Pat. Nos. 4,485,045; 4,544,545; and EP0102324.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzalkonium chloride. Alternatively, they may be formulated in an ointment such as petrolatum.

It is also envisaged to prepare dry powder formulations of the compounds provided herein, particularly the compounds of formula (I), for pulmonary administration, particularly inhalation. Such dry powders may be prepared by spray drying under conditions which result in a substantially amorphous glassy or a substantially crystalline bioactive powder. Accordingly, dry powders of the compounds of the present invention can be made according to the emulsification/spray drying process disclosed in WO 99/16419 or WO 01/85136. Spray drying of solution formulations of the compounds of the invention can be carried out, e.g., as described generally in the "Spray Drying Handbook", 5th ed., K. Masters, John Wiley & Sons, Inc., NY (1991), in WO 97/41833, or in WO 03/053411.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

The present invention thus relates to the compounds or the pharmaceutical compositions provided herein, wherein the corresponding compound or pharmaceutical composition is to be administered by any one of: an oral route; topical route, including by transdermal, intranasal, ocular, buccal, or sublingual route; parenteral route using injection techniques or infusion techniques, including by subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intrasternal, intraventricular, intraurethral, or intracranial route; pulmonary route, including by inhalation or insufflation therapy; gastrointestinal route; intrauterine route; intraocular route; subcutaneous route; ophthalmic route, including by intravitreal, or intracameral route; rectal route; or vaginal route. Particularly preferred routes of administration are oral administration or parenteral administration.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds according to the invention for oral administration to a human (of approximately 70 kg body weight) may be 0.05 to 8000 mg, preferably 0.1 mg to 4000 mg, of the active ingredient per unit dose. The unit dose may be administered, e.g., 1 to 3 times per day. The unit dose may also be administered 1 to 7 times per week, e.g., with not more than one administration per day. A further exemplary dose of the compounds of formula (I) for oral administration to a human is 50 to 200 mg/kg bodyweight/day, particularly 100 mg/kg/day. It will be appreciated that it may be necessary to make routine variations to the dosage depending on the age and weight of the patient/subject as well as the severity of the condition to be treated. The precise dose and also the route of administration will ultimately be at the discretion of the attendant physician or veterinarian.

The compounds provided herein, particularly the compound of formula (I), or a pharmaceutical composition comprising such a compound can be administered in monotherapy (e.g., without concomitantly administering any further therapeutic agents, or without concomitantly administering any further therapeutic agents against the same disease that is to be treated or prevented with the compound of formula (I)). However, the compound of formula (I) or a pharmaceutical composition comprising the compound of formula (I) can also be administered in combination with one or more further therapeutic agents. If the compound of formula (I) is used in combination with a second therapeutic agent active against the same disease or condition, the dose of each compound may differ from that when the corresponding compound is used alone, in particular, a lower dose of each compound may be used. The combination of the compound of formula (I) with one or more further therapeutic agents (such as, e.g., a BRD4 inhibitor, preferably a direct BRD4 inhibitor) may comprise the simultaneous/concomitant administration of the compound of formula (I) and the further therapeutic agent(s) (either in a single pharmaceutical formulation or in separate pharmaceutical formulations), or the sequential/separate administration of the compound of formula (I) and the further therapeutic agent(s). If administration is sequential, either the compound of formula (I) according to the invention or the one or more further therapeutic agents may be administered first. If administration is simultaneous, the one or more further therapeutic agents may be included in the same pharmaceutical formulation as the compound of formula (I), or they may be administered in one or more different (separate) pharmaceutical formulations.

Preferably, the one or more further therapeutic agents to be administered in combination with a compound of the present invention are anticancer drugs. The anticancer drug(s) to be administered in combination with a compound of formula (I) according to the invention may, e.g., be selected from: a tumor angiogenesis inhibitor (e.g., a protease inhibitor, an epidermal growth factor receptor kinase inhibitor, or a vascular endothelial growth factor receptor kinase inhibitor); a cytotoxic drug (e.g., an antimetabolite, such as purine and pyrimidine analog antimetabolites); an antimitotic agent (e.g., a microtubule stabilizing drug or an antimitotic alkaloid); a platinum coordination complex; an anti-tumor antibiotic; an alkylating agent (e.g., a nitrogen mustard or a nitrosourea); an endocrine agent (e.g., an adrenocorticosteroid, an androgen, an anti-androgen, an estrogen, an anti-estrogen, an aromatase inhibitor, a gonadotropin-releasing hormone agonist, or a somatostatin analog); or a compound that targets an enzyme or receptor that is overexpressed and/or otherwise involved in a specific metabolic pathway that is misregulated in the tumor cell (e.g., ATP and GTP phosphodiesterase inhibitors, histone deacetylase inhibitors, protein kinase inhibitors (such as serine, threonine and tyrosine kinase inhibitors, e.g., Abelson protein tyrosine kinase inhibitors) and the various growth factors, their receptors and corresponding kinase inhibitors (such as epidermal growth factor receptor kinase inhibitors, vascular endothelial growth factor receptor kinase inhibitors, fibroblast growth factor inhibitors, insulin-like growth factor receptor inhibitors and platelet-derived growth factor receptor kinase inhibitors)); methionine, aminopeptidase inhibitors, proteasome inhibitors, cyclooxygenase inhibitors (e.g., cyclooxygenase-1 or cyclooxygenase-2 inhibitors), topoisomerase inhibitors (e.g., topoisomerase I inhibitors or topoisomerase II inhibitors), poly ADP ribose polymerase inhibitors (PARP inhibitors), and epidermal growth factor receptor (EGFR) inhibitors/antagonists.

An alkylating agent which can be used as an anticancer drug in combination with a compound of the present invention may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, ThioTEPA (N,N'N'-triethylenethiophosphoramide), carboquone, or triaziquone), a hydrazine (such as procarbazine), a triazene (such as dacarbazine), or an imidazotetrazine (such as temozolomide).

A platinum coordination complex which can be used as an anticancer drug in combination with a compound of the present invention may be, for example, cisplatin, carboplatin, nedaplatin, oxaliplatin, satraplatin, or triplatin tetranitrate.

A cytotoxic drug which can be used as an anticancer drug in combination with a compound of the present invention may be, for example, an antimetabolite, including folic acid analogue antimetabolites (such as aminopterin, methotrexate, pemetrexed, or raltitrexed), purine analogue antimetabolites (such as cladribine, clofarabine, fludarabine, 6-mercaptopurine (including its prodrug form azathioprine), pentostatin, or 6-thioguanine), and pyrimidine analogue antimetabolites (such as cytarabine, decitabine, 5-fluorouracil (including its prodrug forms capecitabine and tegafur), floxuridine, gemcitabine, enocitabine, or sapacitabine).

An antimitotic agent which can be used as an anticancer drug in combination with a compound of the present invention may be, for example, a taxane (such as docetaxel, larotaxel, ortataxel, paclitaxel/taxol, tesetaxel, or nab-paclitaxel (e.g., Abraxane®)), a Vinca alkaloid (such as vinblastine, vincristine, vinflunine, vindesine, or vinorelbine), an epothilone (such as epothilone A, epothilone B, epothilone C, epothilone D, epothilone E, or epothilone F) or an epothilone B analogue (such as ixabepilone/azaepothilone B).

An anti-tumor antibiotic which can be used as an anticancer drug in combination with a compound of the present invention may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumor antibiotic isolated from Streptomyces (such as actinomycin (including actinomycin D), bleomycin, mitomycin (including mitomycin C), or plicamycin).

A tyrosine kinase inhibitor which can be used as an anticancer drug in combination with a compound of the present invention may be, for example, axitinib, bosutinib, cediranib, dasatinib, erlotinib, gefitinib, imatinib, lapatinib, lestaurtinib, nilotinib, semaxanib, sorafenib, sunitinib, axitinib, nintedanib, ponatinib, or vandetanib.

A topoisomerase inhibitor which can be used as an anticancer drug in combination with a compound of the present invention may be, for example, a topoisomerase I inhibitor (such as irinotecan, topotecan, camptothecin, belotecan, rubitecan, or lamellarin D) or a topoisomerase II inhibitor (such as amsacrine, etoposide, etoposide phosphate, teniposide, or doxorubicin).

A PARP inhibitor which can be used as an anticancer drug in combination with a compound of the present invention may be, for example, BMN-673, olaparib, rucaparib, veliparib, CEP 9722, MK 4827, BGB-290, or 3-aminobenzamide.

An EGFR inhibitor/antagonist which can be used as an anticancer drug in combination with a compound of the present invention may be, for example, gefitinib, erlotinib, lapatinib, afatinib, neratinib, ABT-414, dacomitinib, AV-412, PD 153035, vandetanib, PKI-166, pelitinib, canertinib, icotinib, poziotinib, BMS-690514, CUDC-101, AP26113, XL647, cetuximab, panitumumab, zalutumumab, nimotuzumab, or matuzumab.

Further anticancer drugs may also be used in combination with a compound of the present invention. The anticancer drugs may comprise biological or chemical molecules, like TNF-related apoptosis-inducing ligand (TRAIL), tamoxifen, amsacrine, bexarotene, estramustine, irofulven, trabectedin, cetuximab, panitumumab, tositumomab, alemtuzumab, bevacizumab, edrecolomab, gemtuzumab, alvocidib, seliciclib, aminolevulinic acid, methyl aminolevulinate, efaproxiral, porfimer sodium, talaporfin, temoporfin, verteporfin, alitretinoin, tretinoin, anagrelide, arsenic trioxide, atrasentan, bortezomib, carmofur, celecoxib, demecolcine, elesclomol, elsamitrucin, etoglucid, lonidamine, lucanthone, masoprocol, mitobronitol, mitoguazone, mitotane, oblimersen, omacetaxine, sitimagene, ceradenovec, tegafur, testolactone, tiazofurine, tipifarnib, vorinostat, or iniparib.

Also biological drugs, like antibodies, antibody fragments, antibody constructs (for example, single-chain constructs), and/or modified antibodies (like CDR-grafted antibodies, humanized antibodies, "full humanized" antibodies, etc.) directed against cancer or tumor markers/factors/cytokines involved in proliferative diseases can be employed in cotherapy approaches with the compounds of the invention. Examples of such biological molecules are anti-HER2 antibodies (e.g. trastuzumab, Herceptin®), anti-CD20 antibodies (e.g. Rituximab, Rituxan®, MabThera®, Reditux®), anti-CD19/CD3 constructs (see, e.g., EP1071752) and anti-TNF antibodies (see, e.g., Taylor P C. Antibody therapy for rheumatoid arthritis. Curr Opin Pharmacol. 2003. 3(3):323-328). Further antibodies, antibody fragments, antibody constructs and/or modified antibodies to be used in cotherapy approaches with the compounds of the invention can be found, e.g., in: Taylor P C. Curr Opin Pharmacol. 2003. 3(3):323-328; or Roxana A. Maedica. 2006. 1(1):63-65.

An anticancer drug which can be used in combination with a compound of the present invention may, in particular, be an immunooncology therapeutic (such as an antibody (e.g., a monoclonal antibody or a polyclonal antibody), an antibody fragment, an antibody construct (e.g., a single-chain construct), or a modified antibody (e.g., a CDR-grafted antibody, a humanized antibody, or a "full humanized" antibody) targeting any one of CTLA-4, PD-1/PD-L1, TIM3, LAG3, OX4, CSF1R, IDO, or CD40. Such immunooncology therapeutics include, e.g., an anti-CTLA-4 antibody (particularly an antagonistic or pathway-blocking anti-CTLA-4 antibody; e.g., ipilimumab or tremelimumab), an anti-PD-1 antibody (particularly an antagonistic or pathway-blocking anti-PD-1 antibody; e.g., nivolumab (BMS-936558), pembrolizumab (MK-3475), pidilizumab (CT-011), AMP-224, or APE02058), an anti-PD-L1 antibody (particularly a pathway-blocking anti-PD-L1 antibody; e.g., BMS-936559, MEDI4736, MPDL3280A (RG7446), MDX-1105, or MEDI6469), an anti-TIM3 antibody (particularly a pathway-blocking anti-TIM3 antibody), an anti-LAGS antibody (particularly an antagonistic or pathway-blocking anti-LAG3 antibody; e.g., BMS-986016, IMP701, or IMP731), an anti-OX4 antibody (particularly an agonistic anti-OX4 antibody; e.g., MED10562), an anti-CSF1R antibody (particularly a pathway-blocking anti-CSF1R antibody; e.g., IMC-CS4 or RG7155), an anti-IDO antibody (particularly a pathway-blocking anti-IDO antibody), or an anti-CD40 antibody (particularly an agonistic anti-CD40 antibody; e.g., CP-870,893 or Chi Lob 7/4). Further immunooncology therapeutics are known in the art and are described, e.g., in: Kyi C et al., FEBS Lett, 2014, 588(2):368-76; Intlekofer A M et al., J Leukoc Biol, 2013, 94(1):25-39; Callahan M K et al., J Leukoc Biol, 2013, 94(1):41-53; Ngiow S F et al., Cancer Res, 2011, 71(21):6567-71; and Blattman J N et al., Science, 2004, 305(5681):200-5.

A BRD4 inhibitor (preferably a direct BRD4 inhibitor), such as CeMMEC2, may also be used as a further therapeutic agent in combination with the compound of formula (I).

The combinations referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the compound of the present invention (particularly the compound of formula (I) or a pharmaceutically acceptable salt, solvate or prodrug thereof) or the further therapeutic agent(s) may be administered first. When administration is simultaneous, the combination may be administered either in the same pharmaceutical composition or in different pharmaceutical compositions. When combined in the same formulation, it will be appreciated that the two or more compounds must be stable and compatible with each other and the other components of the formulation. When formulated separately, they may be provided in any convenient formulation.

The compounds provided herein, particularly the compounds of formula (I), can also be administered in combination with physical therapy, such as radiotherapy. Radiotherapy may commence before, after, or simultaneously with administration of the compounds of the invention. For example, radiotherapy may commence 1-10 minutes, 1-10 hours or 24-72 hours after administration of the compounds. Yet, these time frames are not to be construed as limiting. The subject is exposed to radiation, preferably gamma radiation, whereby the radiation may be provided in a single dose or in multiple doses that are administered over several hours, days and/or weeks. Gamma radiation may be delivered according to standard radiotherapeutic protocols using standard dosages and regimens.

The present invention thus relates to a compound of formula (I) or a pharmaceutically acceptable salt, solvate, or prodrug thereof, or a pharmaceutical composition comprising any of the aforementioned entities in combination with a pharmaceutically acceptable excipient, for use in the treatment or prevention of cancer, wherein the compound or the pharmaceutical composition is to be administered in combination with one or more anticancer drugs and/or in combination with radiotherapy.

Yet, the compounds of formula (I) can also be used in monotherapy, particularly in the monotherapeutic treatment or prevention of cancer (i.e., without administering any other anticancer agents until the treatment with the compound(s) of formula (I) is terminated). Accordingly, the invention also relates to a compound of formula (I) or a pharmaceutically acceptable salt, solvate, or prodrug thereof, or a pharmaceutical composition comprising any of the aforementioned entities in combination with a pharmaceutically acceptable excipient, for use in the monotherapeutic treatment or prevention of cancer.

The subject or patient to be treated in accordance with the present invention may be an animal (e.g., a non-human animal), a vertebrate animal, a mammal, a rodent (e.g., a guinea pig, a hamster, a rat, or a mouse), a canine (e.g., a dog), a feline (e.g., a cat), a porcine (e.g., a pig), an equine (e.g., a horse), a primate or a simian (e.g., a monkey or an ape, such as a marmoset, a baboon, a gorilla, a chimpanzee, an orangutan, or a gibbon), or a human. In accordance with the present invention, it is envisaged that animals are to be treated which are economically, agronomically or scientifically important. Scientifically important organisms include, but are not limited to, mice, rats, and rabbits. Lower organisms such as, e.g., fruit flies like *Drosophila melagonaster* and nematodes like *Caenorhabditis elegans* may also be used in scientific approaches. Non-limiting examples of agronomically important animals are sheep, cattle and pigs, while, for example, cats and dogs may be considered as economically important animals. Preferably, the subject/patient is a mammal. More preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutan, a gibbon, a sheep, cattle, or a pig). Most preferably, the subject/patient is a human.

The term "treatment" of a disorder or disease as used herein (e.g., "treatment" of cancer) is well known in the art. "Treatment" of a disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

The "treatment" of a disorder or disease may, for example, lead to a halt in the progression of the disorder or disease (e.g., no deterioration of symptoms) or a delay in the progression of the disorder or disease (in case the halt in progression is of a transient nature only). The "treatment" of a disorder or disease may also lead to a partial response (e.g., amelioration of symptoms) or complete response (e.g., disappearance of symptoms) of the subject/patient suffering from the disorder or disease. Accordingly, the "treatment" of a disorder or disease may also refer to an amelioration of the disorder or disease, which may, e.g., lead to a halt in the progression of the disorder or disease or a delay in the progression of the disorder or disease. Such a partial or complete response may be followed by a relapse. It is to be understood that a subject/patient may experience a broad range of responses to a treatment (such as the exemplary responses as described herein above). The treatment of a disorder or disease may, inter alia, comprise curative treatment (preferably leading to a complete response and eventually to healing of the disorder or disease) and palliative treatment (including symptomatic relief).

The term "prevention" of a disorder or disease as used herein (e.g., "prevention" of cancer) is also well known in the art. For example, a patient/subject suspected of being prone to suffer from a disorder or disease may particularly benefit from a prevention of the disorder or disease. The subject/patient may have a susceptibility or predisposition for a disorder or disease, including but not limited to hereditary predisposition. Such a predisposition can be determined by standard methods or assays, using, e.g., genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of a compound of the present invention before any clinical and/or pathological symptoms are diagnosed or determined or can be diagnosed or determined by the attending physician.

It is to be understood that the present invention specifically relates to each and every combination of features and embodiments described herein, including any combination of general and/or preferred features/embodiments. In particular, the invention specifically relates to each combination of meanings (including general and/or preferred meanings) for the various groups and variables comprised in formula (I).

In this specification, a number of documents including patent applications, scientific literature and manufacturers' manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention is also described by the following illustrative figures. The appended figures show:

FIG. 1: Generation of a reporter cell line for the inhibition of BRD4

(a) Graphic representation of the experimental approach. WT-KBM7 cells were treated with 0.5 µM (S)-JQ1 for 18 hours and then infected with the LZRS-RFP-ires-ZEO retroviral vector. RFP-positive cells were sorted in presence of 0.5 µM (S)-JQ1. (S)-JQ1 was removed from the media and the RFP negative population was sorted into single cell clones. All the clones were treated several times with (S)-JQ1 to check whether the treatment was stably inducing RFP expression. (b) Sorting panels representing the WT-KBM7 population (not infected), the infected and sorted population (red square: RFP-positive and sorted cells), and the double sorted population (black square: RFP negative and double sorted cells). (c) Representative FACS panels of REDS3 cells treated with 0.5 µM (R)-JQ1 or (S)-JQ1 for 18 hours; an equal volume of DMSO was used as control. At least three biological replicates were done for each experimental condition. (d) Quantification of RFP-positive cells by FACS, following downregulation of the indicated bromodomain proteins in REDS3 cells (BRDW1 and BRD1 were used as negative controls); three biological replicates were done for each experimental condition and at least 30,000 cells were analyzed each time (mean±STD). (e) Representative images of REDS3 cells downregulated for BRD3 or BRD4 (hairpin number 2 for both of these bromodomains).

FIG. 2: Transcriptional repression of BRD4 target genes induces upregulation of flanking regions (a) Representative pictures of the FISH assay done in REDS3 cells. RFP probe (purple dots) stains the RFP insertion; Hoechst (blue signal) stains the nucleus. Yellow dashed lines mark nuclear perimeter. Scale bar is 10 µM. (b) Quantification of RFP probe localization with respect to the nuclear membrane. Near and far indicate the distance between the RFP FISH probe and the nuclear membrane (0<near<2 µM; far>2 µM); duplicates were performed and at least 80 cells were counted for each experimental condition (mean±STD). (c) Representation of the RFP locus. RFP (red arrow) is inserted in the sense direction at 12 chromosome (chr12:131,323,912-131,324,450) between STX2 (reverse direction, cyan arrow) and RAN (sense direction, cyan arrow); primers used in d are indicated in the representation (WT genome: green lines; REDS3 genome: purple lines). The region between STX2 and RAN is enhancer-rich (light orange dashed line), while the region downstream of STX2 is heterochromatic (gray dashed loops). In the box: representation of ENCODE/Broad institute chromatin state segmentation and Chip-seq (H3K4 ml, H3K4m3, H3K27ac, H3K27m3 and H3H36m3) data (K-562 cell line). (d) PCR of WT and REDS3 DNA using specific primers for the locus of the RFP insertion; primers amplifying the insulin promoter (Ins_P) have been used as control. (e) Volcano plot representing gene expression changes in KBM7 cells upon treatment with 1 µM (S)-JQ1 for 24 hours, compared to DMSO treatment (RNAseq data analysis; grey dots, not significant (qvalue>0.05)/red dots, significant (qvalue<0.05)). (f) DAVID functional annotation analysis of WT-KBM7 (S)-JQ1-upregulated genes. (g) RT-PCR showing STX2 and RAN fold change upon treatment with (S)-JQ1 1 µM for 24 hours in KBM7 cells. Values are normalized to actin expression and DMSO treated cells. Three biological replicates were done for each condition (mean±STD).

FIG. 3: Screening for functional BRD4 inhibitors (a) Heat map showing the increase of RFP-positive nuclei in REDS3 clone treated with the showed compounds at 1, 5 and 10 µM for 24 hours (triplicates, % of control, DMSO is used as negative control and (S)-JQ1 20 µM as positive control). (b) Scatter plot representing the hit distribution from the last part of the screening (validation part). The variable RED was calculated as the product of the number of red cells multiplied by the median red intensity. Autofluorescent compounds increase RED in WT-KBM7 cells, whereas hit compounds act only in RED3 cells. (c) Percentage of c-MYC expression in WT-KBM7 treated with the selected compounds, assessed by RT-PCR. 1, 10 and 20 µM of each compound were used to treat cells for 24 hours; DMSO was used as negative control and (S)-JQ1 as positive control. Three biological replicates were performed (mean±STD). (d) Chemical structures of (S)-JQ1, CeMMEC1 and CeMMEC2. (e) Quantification of cells in S-phase by staining the nuclei with PI and analyzing DNA content by FACS. THP1 cells were treated with DMSO or the indicated concentrations of (S)-JQ1, CeMMEC1 or CeMMEC2 for 48 hours. Three different biological replicates were performed and 30,000 cells were analysed each time (mean±STD). (f) Quantification of AnnexinV positive cells from immunofluorescence images. Cells were treated with DMSO or the indicated concentrations of (S)-JQ1, CeMMEC1 or CeMMEC2 for 72 hours. At least 3 biological replicates were performed and more than 1,500 cells were quantified for each point (mean±STD).

FIG. 4: Molecular and cellular characterization of CeMMEC1 and CeMMEC2

(a) AlphaLISA assays for the first (black columns, BD1) and the second (grey columns, BD2) bromodomains of BRD4, incubated with CeMMEC1 and CeMMEC2. (S)-JQ1 and RVX-208 were used as positive controls. The assay was done in duplicate (mean±STD); all compounds were used at 10 µM. (b) AlphaLISA dose response (12 dilutions, from 20 to 0.02 µM) for full length BRD4 (GST-tagged) incubated with (S)-JQ1 or CeMMEC2. (c) BromoScan profile for CeMMEC1 (red bubbles) and CeMMEC2 (pink bubbles) (10 uM). Bubbles indicate the percentage of inhibition of the binding of the analyzed bromodomains to an acetylated substrate. (d) Representative Western Blots showing knock down levels of the indicated bromodomain downregulated using two different shRNAs (shRNAC=control_sh; shRNA1=hairpin n.1; shRNA2=hairpin n.2.) (e) RFP-positive REDS3 cells quantification upon downregulation of the indicated bromodomains from live cell imaging pictures. Three replicates were perfromed and more than 1,500 cells were quantified for each point (% of control, positive control is shControl treated with DMSO, positive control is shControl treated with (S)-JQ1; mean±STD). (f) RFP-positive cell fold change quantified from live cell imaging pictures of REDS3 clone treated with the indicated compounds at the displayed concentrations for 24 hours (DMSO normalized; duplicates, at least 1500 cells were quantified in each replicate). (g) BromoKdELECT assay for CeMMEC1 against TAF1 (2). (h) Docking of CeMMEC2 to the first bromodomain of BRD4. (i) Docking of CeMMEC1 to the second bromodomain of TAF1. 3D model (top panel) and 2D ligand interaction diagram (bottom panel). Red dots in the 3D model indicate water molecules.

Figure 5:
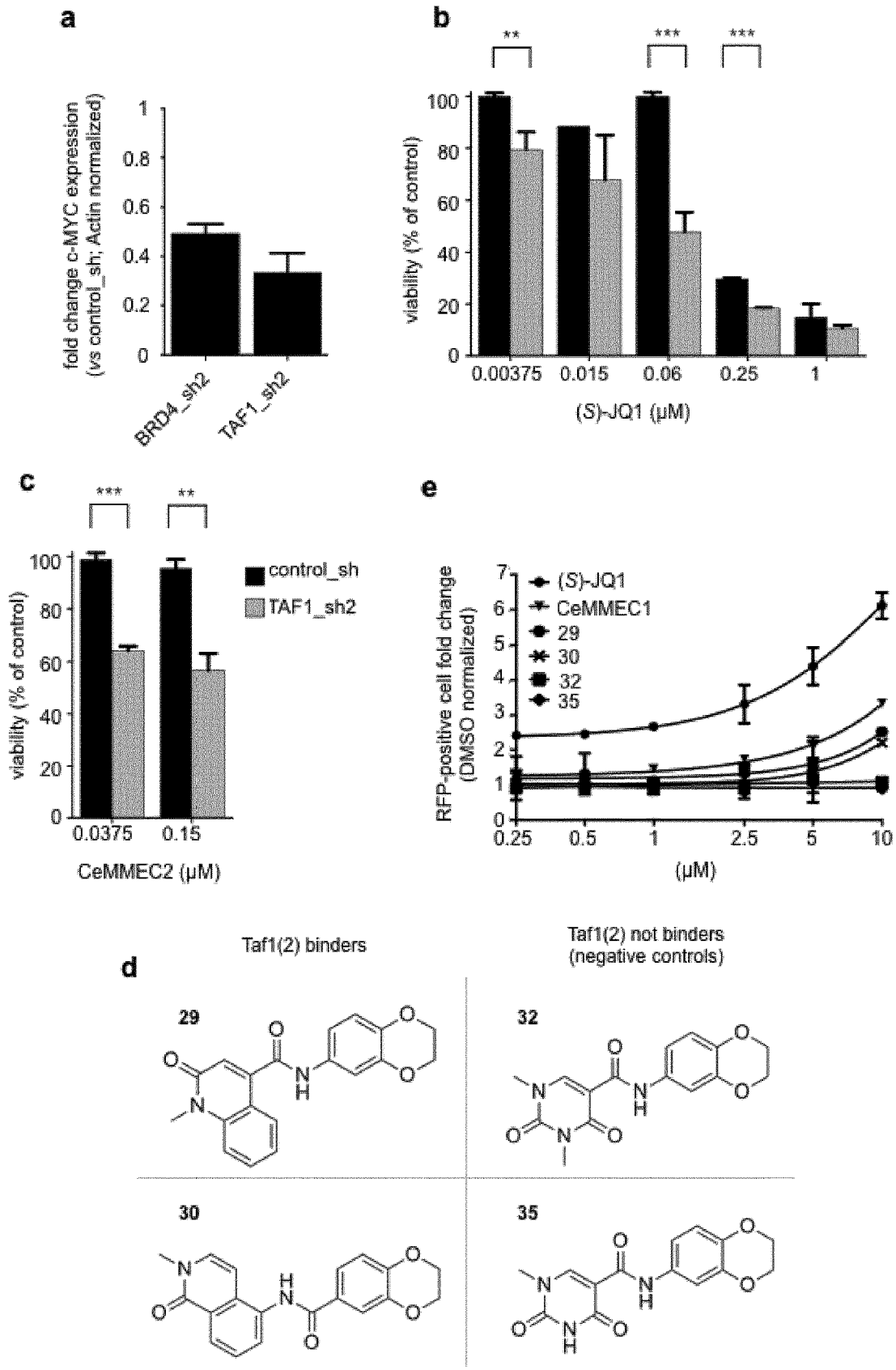
Figure 5:
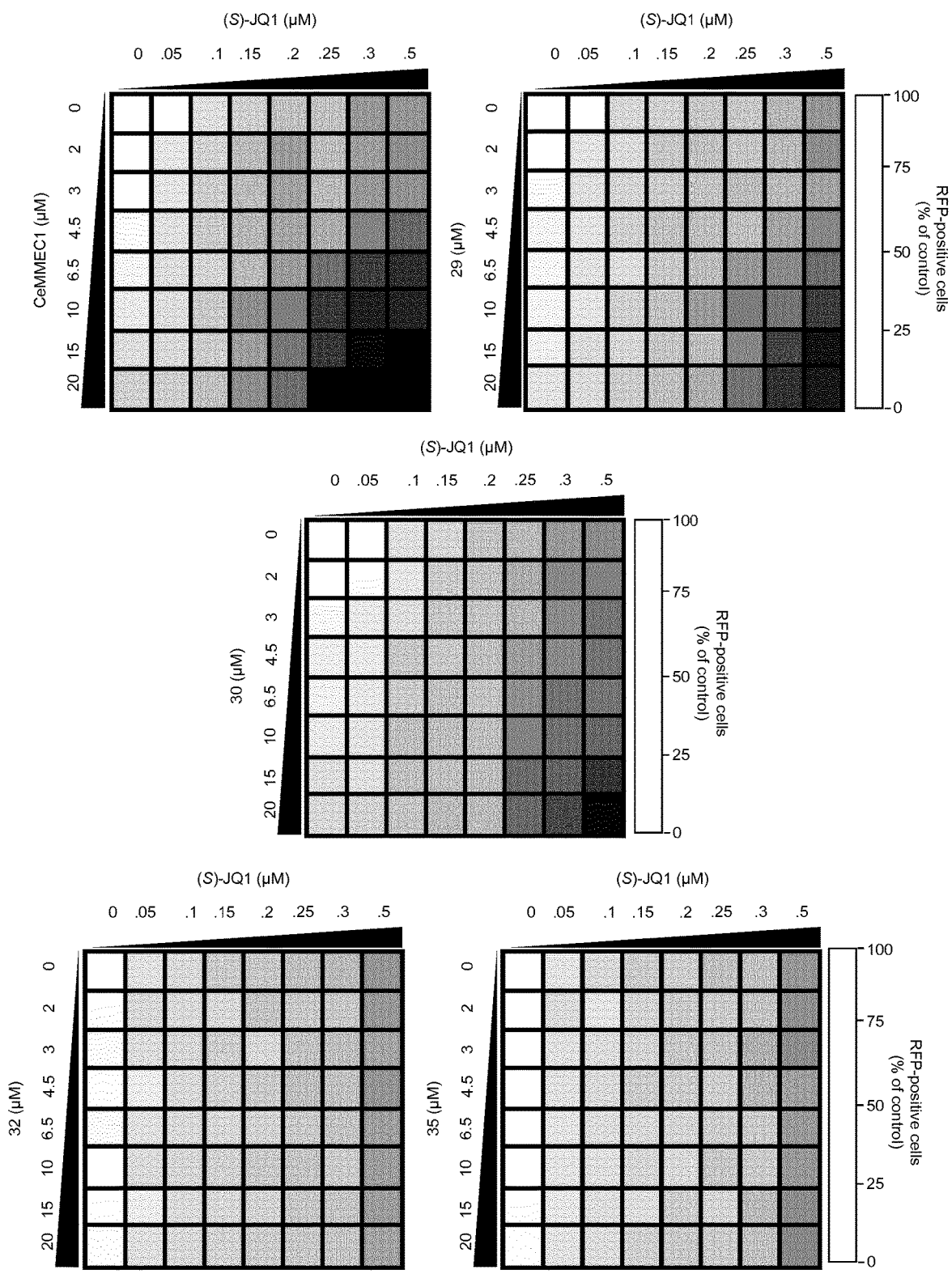
Figure 5:
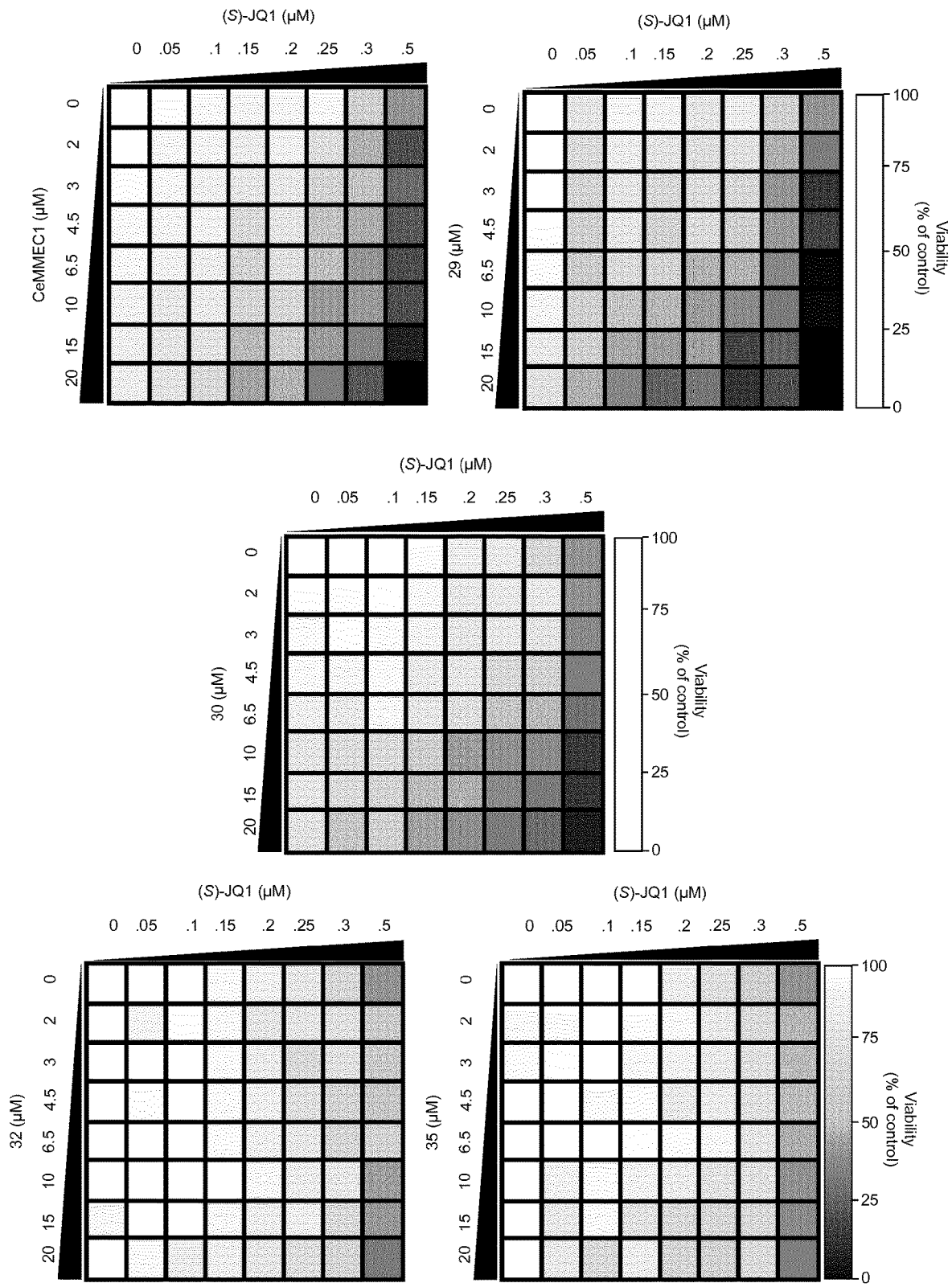

FIG. 5: TAF1 synergizes with BRD4 to mediate transcriptional control (a) Fold change c-MYC expression assessed by RT-PCR in WT-KBM7 with knockdown of TAF1 or BRD4 (compared to control cells); three biological replicates were performed (mean±STD). (b, c) CellTiterGlo assay of control and TAF1 downregulated WT-KBM7 treated with the indicated concentrations of (b) (S)-JQ1 or (c) CeMMEC2 (each point performed at least in triplicate, an equal amount of DMSO was added as control). (d) Chemical structures of the indicated CeMMEC1 analogs. (e) RFP-positive cell fold change quantified from live cell imaging pictures of REDS3 clone treated with the indicated compounds at the displayed concentrations for 24 hours (DMSO normalized; duplicates, at least 1500 cells were quantified in each replicate). (f) Matrix displaying fold change of REDS3 RFP-positive cells treated with the indicated concentrations of (S)-JQ1, CeMMEC1, analog 29, analog 30, analog 32 and analog 35 alone or in combination (each point at least in triplicate). (g) Matrix displaying cell viability reduction of H23 cells treated with the indicated concentrations of (S)-JQ1, CeMMEC1, analog 29, analog 30, analog 32 and analog 35 alone or in combination (each point done at least in duplicate, an equal amount of DMSO was added as control). Statistics (Student's t-test, two tails): * indicates $0.05<\text{pvalue}<0.01$;  indicates $0.01<\text{pvalue}<0.001$; * indicates pvalue<0.001.

FIG. 6: Characterization of RED3 cells (a) Western Blot analysis showing c-MYC downregulation in WT-KBM7 treated with 0.5 µM (S)-JQ1 for 18 hours; an equal volume of DMSO was used as control. (b) S-phase quantification from cell cycle profiles evaluated by PI-staining and DNA content analysis by FACS. WT-KBM7 cells were treated with 0.5 µM of (S)-JQ1 or (R)-JQ1 for 24 hours; an equal amount of DMSO was added as control. Four biological replicates have been done (mean). (c) Examples of live cell imaging pictures of REDS1, REDS2 and REDS3 cells treated with 0.5 µM of (S)-JQ1 or (R)-JQ1; an equal amount of DMSO was added as control. (d) RFP and (e) zeocin expression performed by RT-PCR in REDS3 cells treated with 0.5 µM (S)-JQ1 or (R)-JQ1 for 18 hours; an equal volume of DMSO was used as control. Three biological replicates were performed for each experimental condition (mean±STD). (f) Left panel: cell cycle profiles of REDS3 untreated cells or REDS3 cells treated for 20 hours with thymidine (2 mM), RO3306 (9 µM) or nocodazole (1 µM). Nuclei were stained with PI and DNA content quantified by FACS; representative cell cycle profiles from one of the two experiments done (30,000 cells were FACS analyzed in each experiment). Right panel: examples of live cell imaging pictures of REDS3 cells treated as above and with 0.5 µM of (S)-JQ1; an equal volume of DMSO was used as control. Representative pictures from one of the three replicates done. (g) Quantification of RFP-positive cells by live cell imaging pictures of REDS3 cells treated with PMA (200 nM), PHA (5ug/ml), (S)-JQ1 (1 µM) or a combination of PMA or PHA with (S)-JQ1 for 24 hours. An equal amount of DMSO was added as control; three replicates were done and at least 1,500 cells were quantified. (h) BRD3, BRD4 and RFP expression assessed by RT-PCR in BRD3 or BRD4 downregulated REDS3 cells; three biological replicates were done for each experimental condition (mean±STD).

FIG. 7: Characterization of screening hits (a) Pipeline for the selection of validated hits. Compound library: collection of 89,355 small molecules. DR: Dose Response; TC: Time Course. (b) Representation of the criteria used for the selection of the positive control concentration ((S)-JQ1 0.5 µM) applied in the screening in terms of RFP fluorescence increase (from live cell imaging pictures quantification, duplicates) and (c) its associated Z-Factor. (d) Example of live cell imaging pictures of REDS3 cells treated with 10 µM of (S)-JQ1, CeMMEC1 or CeMMEC2 for 24 hours. An equal volume of DMSO was used as control. (e) Quantification of RFP-positive nuclei of REDS3 cells treated with (S)-JQ1, CeMMEC1 and CeMMEC2 at 0.5, 1, 2.5, 5, 10 and 20 µM from live cell imaging pictures. An equal amount of DMSO was added as control; three replicates were done and at least 1,500 cells were quantified in each experiment (mean±STD). (f) RNA-seq analysis: Venn diagrams indicating the number of up- and down-regulated genes in WT-KBM7 cells treated with (S)-JQ1 1 µM (grey), CeMMEC1 10 µM (red) and CeMMEC2 10 µM (pink) for 24 hours, and the overlapping of these groups. (g) Scatter plot representing the correlation of gene expression variation in cells treated as in D.

FIG. 8: Characterization of the binding of CeMMEC1 and CeMMEC2 to bromodomain proteins (a) Dose response (12 dilutions, from 20 to 0.02 µM) AlphaLISA assay for the first (BD1) and the second (BD2) bromodomain of BRD4 incubated with (S)-JQ1 and CeMMEC2. The assay was done in duplicate (mean±STD); (b) BromoKdELECT assay for CeMMEC1 against TAF1 (2), BRD9, CREBBP and EP300 bromodomains (11 dilutions, from 10 to 0.017 µM). (c) not used (d) KinomeScan profile for CeMMEC1 (10 µM). Bubbles indicate the percentage of inhibition of the binding of the analyzed kinase to an immobilized ligand. (e) BromoELECT assay for CeMMEC1 and analogs A1, A2, 05, 10, 13, 24, 25, 26, 27, 29, 33 and 39 (10 µM) against BRD4 (1), BRD4 (2), BRD9, CREBBP, EP300 and TAF1 (2). (f, g) Docking poses of analog 30 to TAF1 (green) and BRD4 (magenta). (h) Docking of compound 29 to TAF1, no suitable pose could be identified for BRD4. (i) BromoELECT assay for analog 29 (10 µM) against BRD4 (1), BRD9, CREBBP, EP300 and TAF1 (2).

FIG. 9: Interaction of BRD4 and TAF1

(a) Fold change RFP expression assessed by RT-PCR in REDS3 cells with shRNA downregulation of TAF1 or BRD4 (compared to control cells); three biological replicates were done (mean±STD). (b) Flag pull-down using protein extracts from HEK293T overexpressing flag-BRD4 (full length) or flag alone (representative images from one of the three experiments done). (c) CellTiterGlo assay of control and TAF1 downregulated WT-KBM7 treated with the indicated concentrations of CeMMEC1 (each point at least in triplicate, an equal amount of DMSO was added as control). (d) Matrix displaying cell viability reduction of THP1 treated with the indicated concentrations of (S)-JQ1, CeMMEC1, analog 29, analog 30, analog 32 and analog 35 alone or in combination (each point done at least in duplicate, equal amount of DMSO was added as control). (e) Differential Volume values as measure of the synergy between (S)-JQ1 and CeMMEC1 or the indicated analogs from the treatments represented in the matrix in d and FIG. 5g.

FIG. 10: Small molecule screening data

The reference to "supplementary table 1" in this figure refers to FIG. 11.

FIG. 11: Summary of bioactivity data of hit compounds

Redness: RFP-positive cell fold change after 24 hours treatment. All compounds at 10 µM (values are DMSO normalized).

AlphaLISA: POC (percentage of control) of BRD4_BD1 (first bromodomain) binding. All compounds at 10 µM.

"True hit": identification of alphaLISA false positives (quenching compounds) using the true hits kit (PerkinElmer); "Y" means not quenching compounds (true hit=Yes); "N" means quenching compound (true hit=No).

AnnV+: % of AnnexinV positive cells after 48 hours treatment. All compounds at 10 µM (values are DMSO normalised).

Cell cycle: cell cycle phenotype after 72 hours treatment. All compounds at 10 µM.

Myc: % of remaining Myc expression after 24 hours treatment. All compounds at 10 µM (values are DMSO normalised).

ND=not determined.

FIG. 12: Bioactivity data of CeMMEC1 and derivatives thereof

Redness (% induction at 10 µM), BRD4_BD1 (% inhibition at 10 µM), BRD4_BD2 (% inhibition at 10 µM), BRD9 (% inhibition at 10 µM), CREBBP (% inhibition at 10 µM), EP300 (% inhibition at 10 µM), and TAF1_BD2 (% inhibition at 10 µM) are shown for CeMMEC1 and derivatives thereof.

The present invention particularly relates to the following items:

1. A compound of the following formula (I):

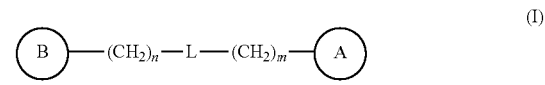

wherein:

ring B is a group having the following structure:

one of the ring atoms $X_2$ and $X_3$ is $N(R^{X1})$, and the other one of said ring atoms $X_2$ and $X_3$ is $C(=O)$;

the ring atom $X_1$ is selected from $N(R^{X1})$, $C(R^{X2})$ and $C(=O)$, and the ring atoms $X_4$ and $X_5$ are each independently selected from $N(R^{X1})$, $C(R^{X3})$ and $C(=O)$; wherein at least one of said ring atoms $X_1$, $X_4$, and $X_5$ is different from $N(R^{X1})$ and $C(=O)$; and further wherein if $X_3$ and $X_5$ are $C(=O)$, $X_4$ is $N(R^{X1})$, and $X_1$ is $C(R^{X2})$, then $X_2$ is $N(H)$;

each ----- is independently a single bond or a double bond, wherein at least one of any two adjacent bonds ----- is a single bond;

each $R^{X1}$ is independently selected from hydrogen, $C_{1-5}$ alkyl, —CO($C_{1-5}$ alkyl), —($C_{0-3}$ alkylene)-aryl, and —($C_{0-3}$ alkylene)-heteroaryl, wherein the aryl comprised in said —($C_{0-3}$ alkylene)-aryl and the heteroaryl comprised in said —($C_{0-3}$ alkylene)-heteroaryl are each optionally substituted with one or more groups $R^{X11}$.

$R^{X2}$ is selected from hydrogen, $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$alkylene)-CO—O—($C_{1-5}$ alkyl), —($C_{0-3}$ alkylene)-O—CO—($C_{1-5}$ alkyl), —($C_{0-3}$alkylene)-CO—NH$_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH($C_{1-5}$ alkyl), —($C_{0-3}$alkylene)-SO$_2$—N($C_{1-5}$alkyl)($C_{1-5}$ alkyl), —($C_{0-3}$ alkylene)-NH—$SO_2$—($C_{1-5}$ alkyl), and —($C_{0-3}$ alkylene)-N($C_{1-5}$ alkyl)-$SO_2$—($C_{1-5}$ alkyl);

the two groups $R^{X3}$ are either mutually linked to form, together with the ring carbon atoms that they are attached to, a 5- or 6-membered cyclyl group which is optionally substituted with one or more groups $R^{X31}$, or the two groups $R^{X3}$ are each independently selected from hydrogen, $C_{1-5}$ alkyl, $C_{2-5}$ alkenyl, $C_{2-5}$ alkynyl, —OH, —O($C_{1-5}$ alkyl), —O($C_{1-5}$ alkylene)-OH, alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —$CF_3$, —CN, —$NO_2$, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), and —N($C_{1-5}$ alkyl)-$SO_2$—($C_{1-5}$ alkyl);

each $R^{X11}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-$CF_3$, —($C_{0-3}$ alkylene)-CN, —($C_{0-3}$ alkylene)-$NO_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), and —($C_{0-3}$ alkylene)-N($C_{1-5}$ alkyl)-$SO_2$—($C_{1-5}$ alkyl);

each $R^{X31}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-$CF_3$, —($C_{0-3}$ alkylene)-CN, —($C_{0-3}$ alkylene)-$NO_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), and —($C_{0-3}$ alkylene)-N($C_{1-5}$ alkyl)-$SO_2$—($C_{1-5}$ alkyl);

ring B is attached to the remainder of the compound of formula (I) via the ring carbon atom that is marked with an asterisk (*) or, if $X_4$ and $X_5$ are each C($R^{X3}$) and the two groups $R^{X3}$ are mutually linked to form, together with the ring carbon atoms that they are attached to, a 5- or 6-membered cyclyl group which is optionally substituted with one or more groups $R^{X31}$, then ring B may also be attached to the remainder of the compound of formula (I) via any ring carbon atom of said 5- or 6-membered cyclyl group;

ring A is aryl or heteroaryl, wherein said aryl and said heteroaryl are each optionally substituted with one or more groups $R^A$;

each $R^A$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-$CF_3$, —($C_{0-3}$ alkylene)-CN, —($C_{0-3}$ alkylene)-$NO_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-cycloalkyl, —($C_{0-3}$ alkylene)-O-cycloalkyl, —($C_{0-3}$ alkylene)-O($C_{1-5}$ alkylene)-cycloalkyl, —($C_{0-3}$ alkylene)-heterocycloalkyl, —($C_{0-3}$ alkylene)-O-heterocycloalkyl, and —($C_{0-3}$ alkylene)-O($C_{1-5}$ alkylene)-heterocycloalkyl;

L is selected from —CO—N($R^{L1}$)—, —N($R^{L1}$)—CO—, —CO—O—, —O—CO—, —C(=N—$R^{L2}$)—N($R^{L1}$)—, —N($R^{L1}$)—C(=N—$R^{L2}$)—, —C(=S)—N($R^{L1}$)—, —N($R^{L1}$)—C(=S)—, —N($R^{L1}$)—CO—N($R^{L1}$)—, —O—CO—N($R^{L1}$)—, —N($R^{L1}$)—CO—O—, —N($R^{L1}$)—C(=N—$R^{L2}$)—N($R^{L1}$)—, —N($R^{L1}$)—C(=N—$R^{L2}$)—O—, —S—C(=N—$R^{L2}$)—N($R^{L1}$)—, —N($R^{L1}$)—C(=N—$R^{L2}$)—S—, —N($R^{L1}$)—C(=S)—N($R^{L1}$)—, —O—C(=S)—N($R^{L1}$)—, —N($R^{L1}$)—C(=S)—O—, —S—CO—N($R^{L1}$)—, and —N($R^{L1}$)—CO—S—;

each $R^{L1}$ is independently selected from hydrogen and $C_{1-5}$ alkyl;

each $R^{L2}$ is independently selected from hydrogen, $C_{1-5}$ alkyl, —CN, and —$NO_2$;

n is 0 or 1; and m is 0 or 1;

or a pharmaceutically acceptable salt, solvate or prodrug thereof for use as a medicament.

2. The compound for use according to item 1, wherein $X_2$ is C(=O), and wherein $X_3$ is N($R^{X1}$).
3. The compound for use according to item 1, wherein $X_2$ is N($R^{X1}$), and wherein $X_3$ is C(=O).
4. The compound for use according to any one of items 1 to 3, wherein $X_1$ is C($R^{X2}$), and wherein $X_4$ and $X_5$ are each C($R^{X3}$).
5. The compound for use according to item 4, wherein the bond ---- between the ring atom $X_1$ and the ring carbon atom which is bound to the moiety —$(CH_2)_n$-L-$(CH_2)_m$— is a double bond, the bond ---- between said ring carbon atom which is bound to the moiety —$(CH_2)_n$-L-$(CH_2)_m$— and the ring atom $X_5$ is a single bond, and the bond ---- between the ring atoms $X_4$ and $X_5$ is a double bond.
6. The compound for use according to any one of items 1 to 5, wherein each $R^{X1}$ is independently selected from hydrogen and $C_{1-5}$ alkyl.
7. The compound for use according to any one of items 1 to 6, wherein each $R^{X1}$ is methyl.
8. The compound for use according to any one of items 1 to 7, wherein $R^{X2}$ is selected from hydrogen, $C_{1-4}$ alkyl, —OH, —O($C_{1-4}$ alkyl), —$NH_2$, —NH($C_{1-4}$ alkyl), —N($C_{1-4}$ alkyl)($C_{1-4}$ alkyl), halogen, —$CF_3$, and —CN.
9. The compound for use according to any one of items 1 to 8, wherein ring B is attached to the remainder of the compound of formula (I) via the ring carbon atom that is marked with an asterisk.
10. The compound for use according to any one of items 1 to 8, wherein $X_4$ and $X_5$ are each C($R^{X3}$) and the two groups $R^{X3}$ are mutually linked to form, together with the ring carbon atoms that they are attached to, a 5- or 6-membered cyclyl group, and wherein ring B is attached to the remainder of the compound of formula (I) via any ring carbon atom of said 5- or 6-membered cyclyl group.
11. The compound for use according to any one of items 1 to 10, wherein the two groups $R^{X3}$ are mutually linked to form, together with the ring carbon atoms that they are attached to, a 5- or 6-membered cycloalkyl group, a 5- or 6-membered cycloalkenyl group, or a phenyl group, wherein said cycloalkyl group, said cycloalkenyl group and said phenyl group are each optionally substituted with one or more groups $R^{X31}$.
12. The compound for use according to any one of items 1 to 11, wherein ring A is selected from 1,4-benzodioxanyl, benzoxanyl, 1,3-benzodioxolanyl, benzoxolanyl, 1,5-benzodioxepanyl, benzodioxepanyl, phenyl, and a 5- or 6-membered monocyclic heteroaryl, wherein said 1,4-benzodioxanyl, said benzoxanyl, said 1,3-benzodioxolanyl, said benzoxolanyl, said 1,5-benzodioxepanyl, said benzodioxepanyl, said phenyl, and said heteroaryl are each optionally substituted with one or more groups $R^A$.
13. The compound for use according to any one of items 1 to 12, wherein ring A is selected from 1,4-benzodioxan-6-yl, 1-benzoxan-6-yl, and 4-methoxyphenyl.
14. The compound for use according to any one of items 1 to 13, wherein L is —CO—N($R^{L1}$)— or —N($R^{L1}$)—CO—.
15. The compound for use according to any one of items 1 to 14, wherein L is —N($R^{L1}$)—CO—, wherein said —N($R^{L1}$)—CO— is bound via its —N($R^{L1}$)— group to the moiety —$(CH_2)_n$—, and via its —CO— group to the moiety —$(CH_2)_m$—.
16. The compound for use according to any one of items 1 to 14, wherein L is —CO—N($R^{L1}$)—, wherein said —CO—N($R^{L1}$)— is bound via its —CO— group to the moiety —$(CH_2)_n$—, and via its —N($R^{L1}$)— group to the moiety —$(CH_2)_m$—.
17. The compound for use according to any one of items 14 to 16, wherein $R^{L1}$ is hydrogen.
18. The compound for use according to any one of items 14 to 17, wherein n is 0.
19. The compound for use according to any one of items 14 to 18, wherein m is 0.
20. The compound for use according to item 1, wherein said compound is a compound of any one of the following formulae:

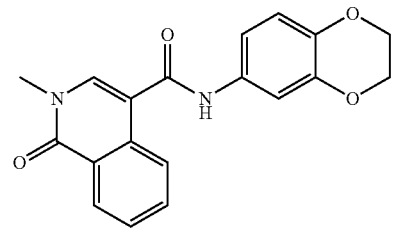

CeMMEC1

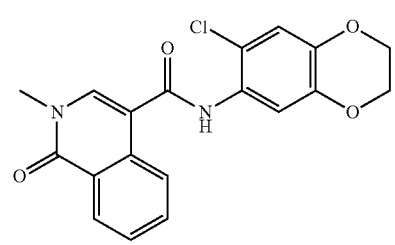

1

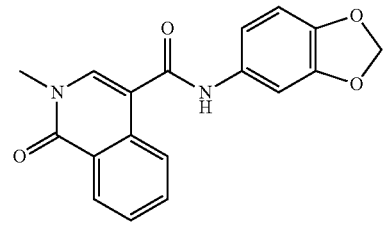

3

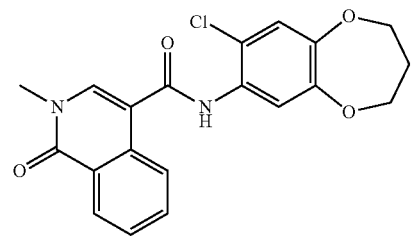

4

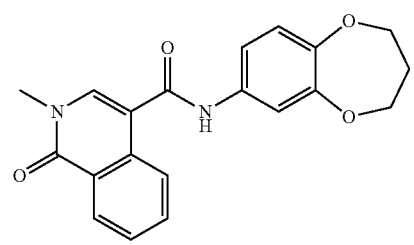

5

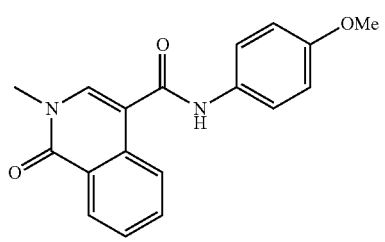
6
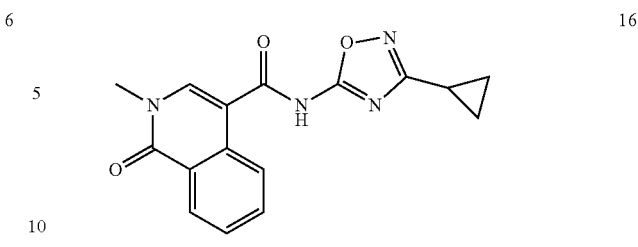
16
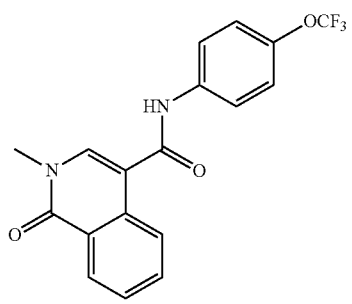
8
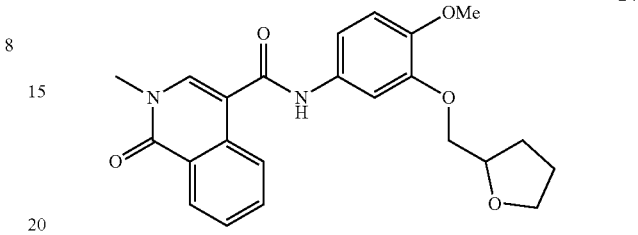
24
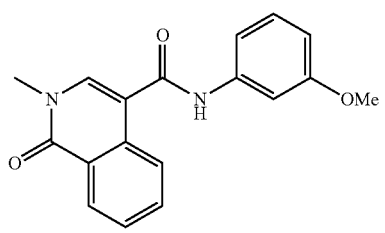
10
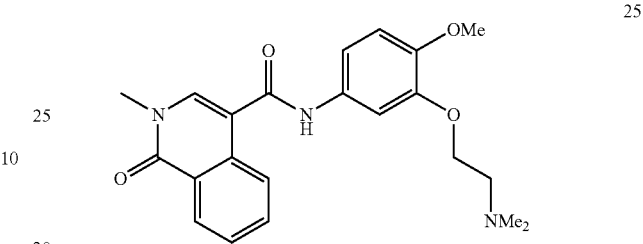
25
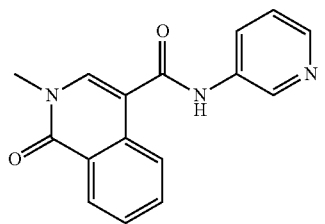
12
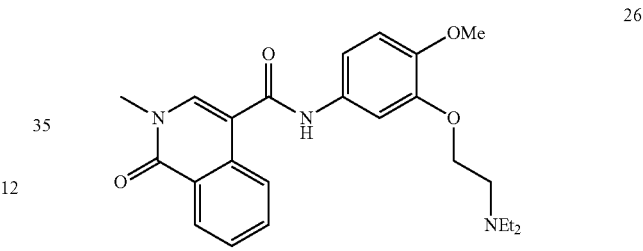
26
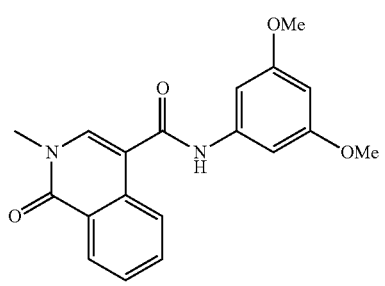
13
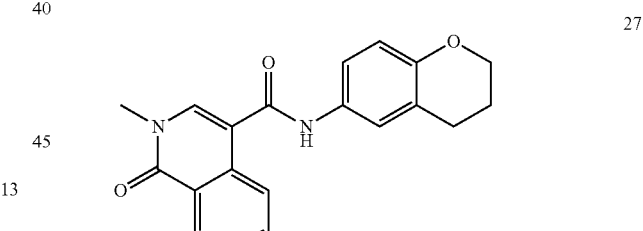
27
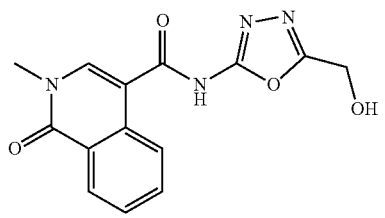
15
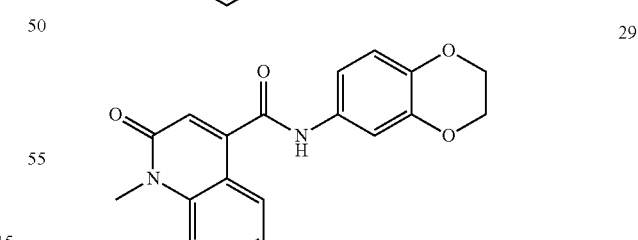
29
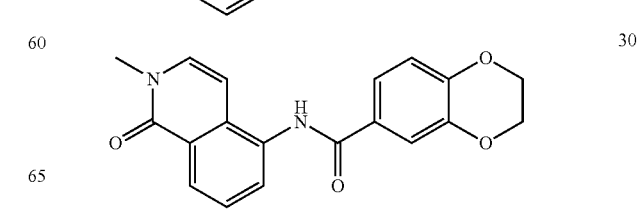
30

33 
36 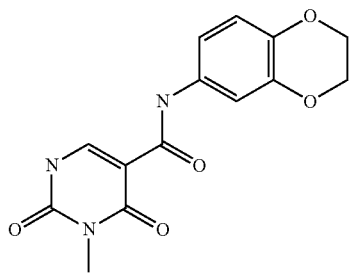
37 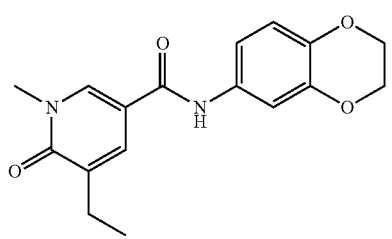
38 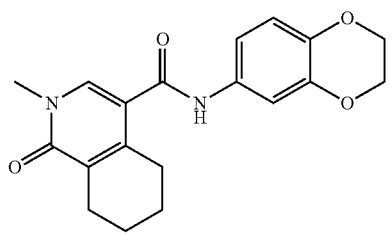
39 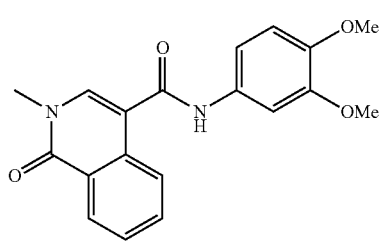
A1 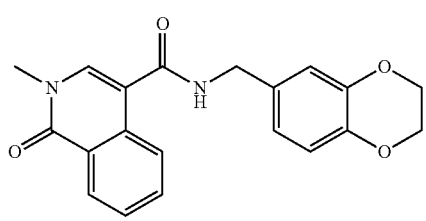
A2 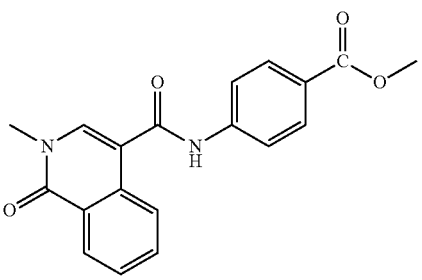
A3 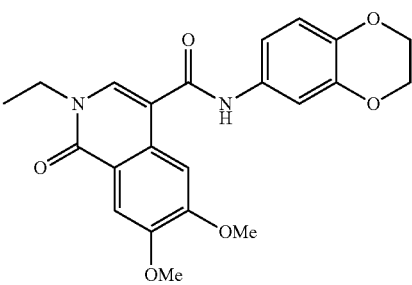
A4 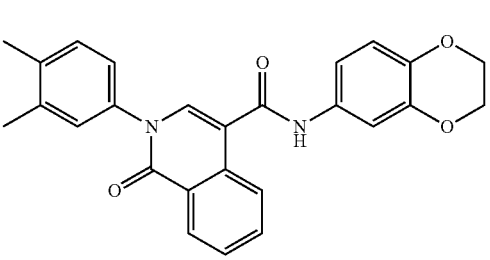
A5 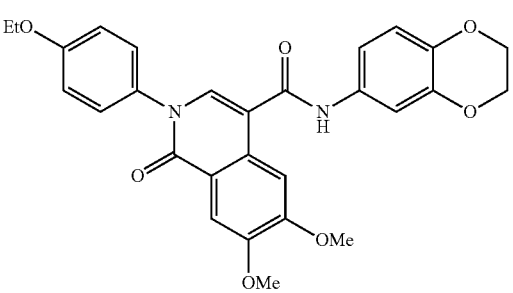
4-1 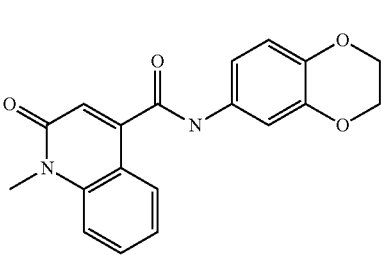
4-2 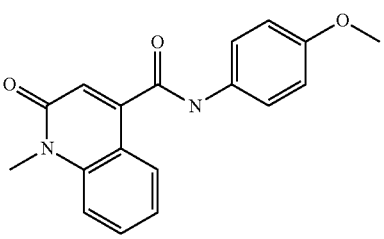

4-3 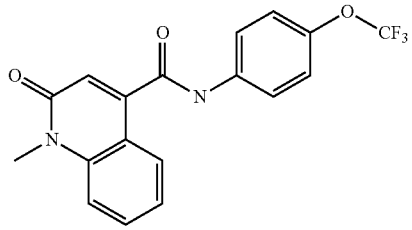
4-4 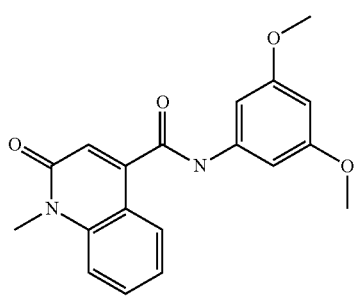
4-10 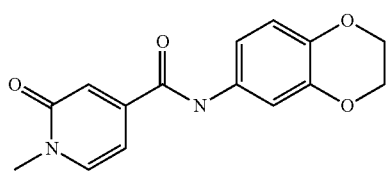
4-13 
4-14 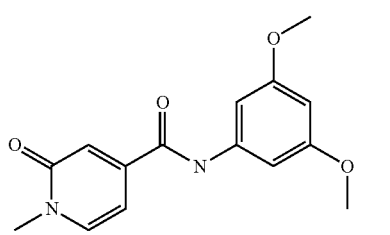
4-16 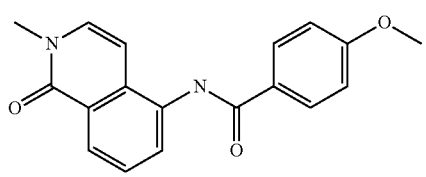
4-17 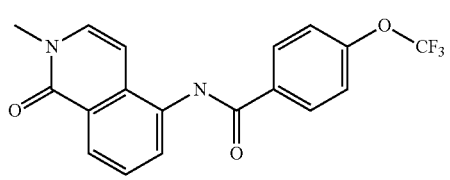
4-24 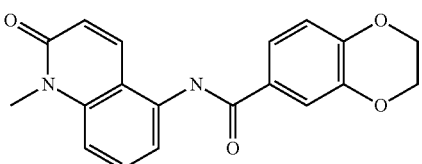
4-25 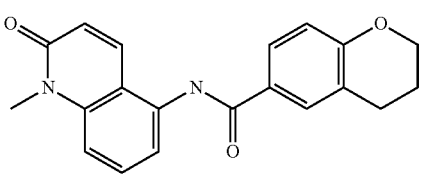
4-26 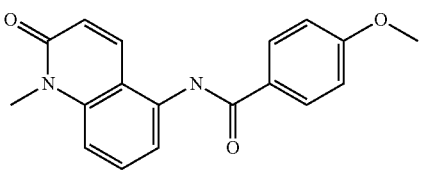
4-28 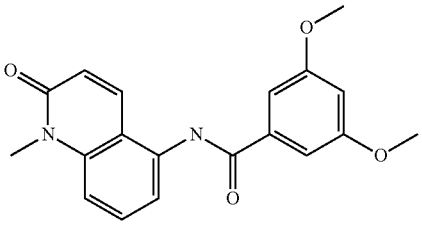
4-29 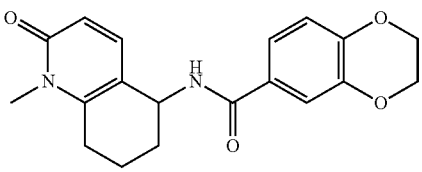
4-31 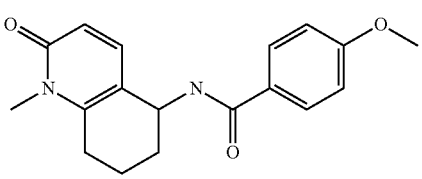
4-32 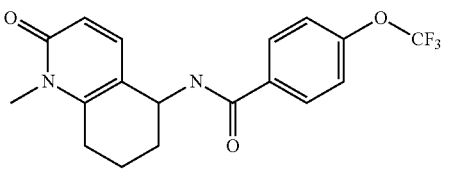
4-33 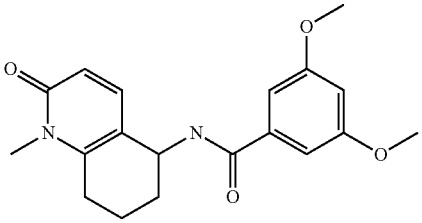
or a pharmaceutically acceptable salt, solvate or prodrug thereof.

21. A pharmaceutical composition comprising a compound as defined in any one of items 1 to 20 and a pharmaceutically acceptable excipient.

22. A compound as defined in any one of items 1 to 20 or the pharmaceutical composition of item 21 for use in the treatment or prevention of cancer.

23. Use of a compound as defined in any one of items 1 to 20 in the preparation of a medicament for the treatment or prevention of cancer.

24. A method of treating or preventing cancer, the method comprising administering a compound as defined in any one of items 1 to 20 or the pharmaceutical composition of item 21 to a subject in need thereof.

25. The compound for use according to item 22 or the pharmaceutical composition for use according to item 22 or the use of item 23 or the method of item 24, wherein said cancer is selected from prostate carcinoma, breast cancer, acute myeloid leukemia, multiple myeloma, glioblastoma, and NUT midline carcinoma.

26. The compound for use according to any one of items 1 to 20, 22 or 25 or the pharmaceutical composition for use according to item 22 or 25 or the use of item 23 or 25 or the method of item 24 or 25, wherein the subject to be treated is a human.

27. The compound for use according to any one of items 1 to 20, 22, 25 or 26 or the pharmaceutical composition for use according to item 22, 25 or 26 or the use of item 23, 25 or 26 or the method of any one of items 24 to 26, wherein the compound of formula (I) is to be administered in combination with a BRD4 inhibitor.

28. The compound for use according to item 27 or the pharmaceutical composition for use according to item 27 or the use of item 27 or the method of item 27, wherein the BRD4 inhibitor is CeMMEC2, (S)-JQ1, I-BET 151, I-BET 762, PF-1, bromosporine, OTX-015, TEN-010, CPI-203, CPI-0610, RVX-208, B12536, TG101348, LY294002, or a pharmaceutically acceptable salt, solvate or prodrug of any one of these agents.

29. The compound for use according to item 27 or the pharmaceutical composition for use according to item 27 or the use of item 27 or the method of item 27, wherein the BRD4 inhibitor is a compound having the following structure:

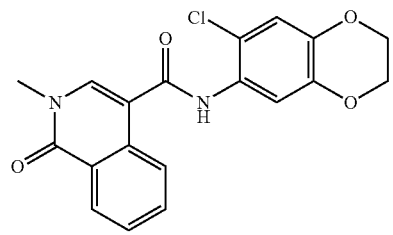

(CeMMEC2)

or a pharmaceutically acceptable salt, solvate or prodrug thereof.

30. In vitro use of a compound as defined in any one of items 1 to 20 as a TAF1 inhibitor.

31. A compound having any one of the following formulae:

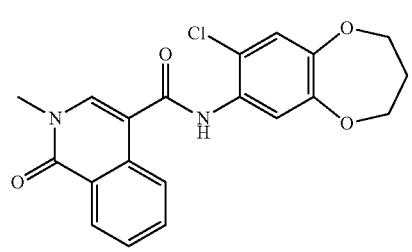

1

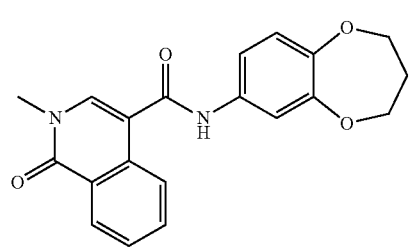

4

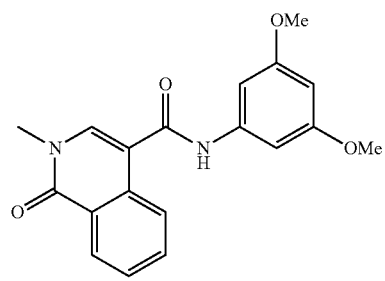

5

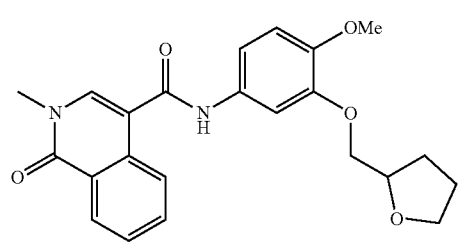

13

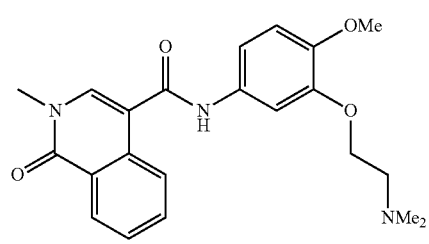

24

25

| | |
|---|---|
| 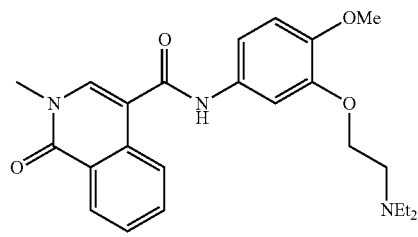 26 | 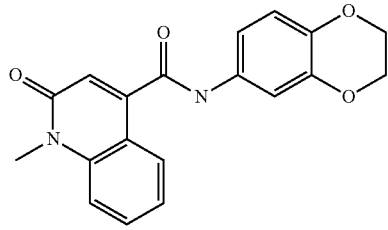 4-1 |
| 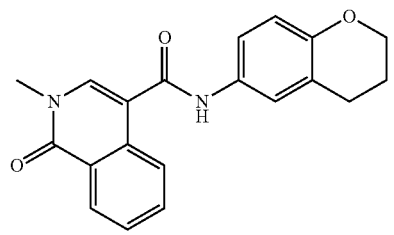 27 |  4-3 |
| 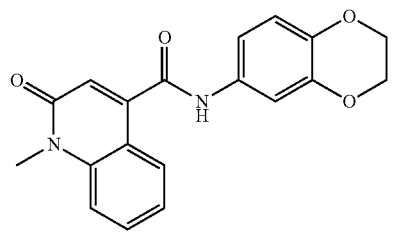 29 | |
| 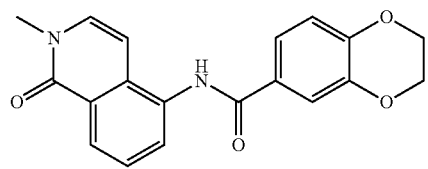 36 | 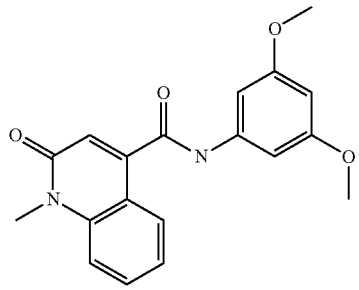 4-4 |
| 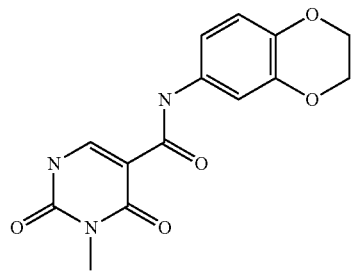 37 | 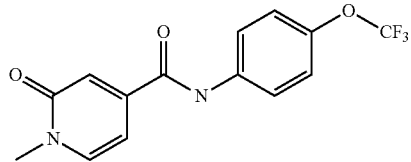 4-13 |
| 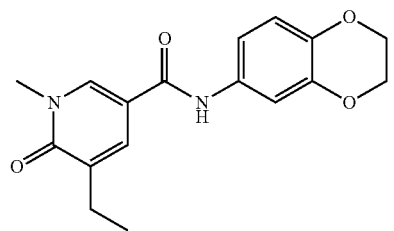 38 | 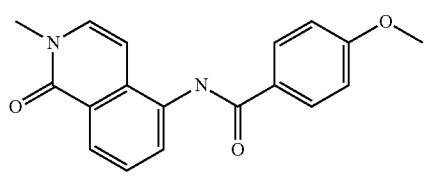 4-16 |
| 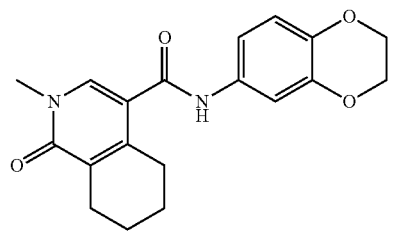 | 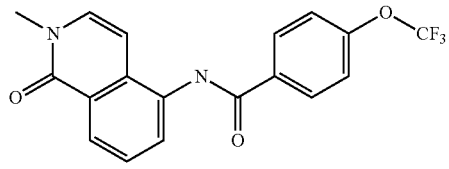 4-17 |
| | 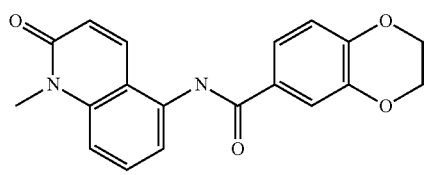 4-24 |

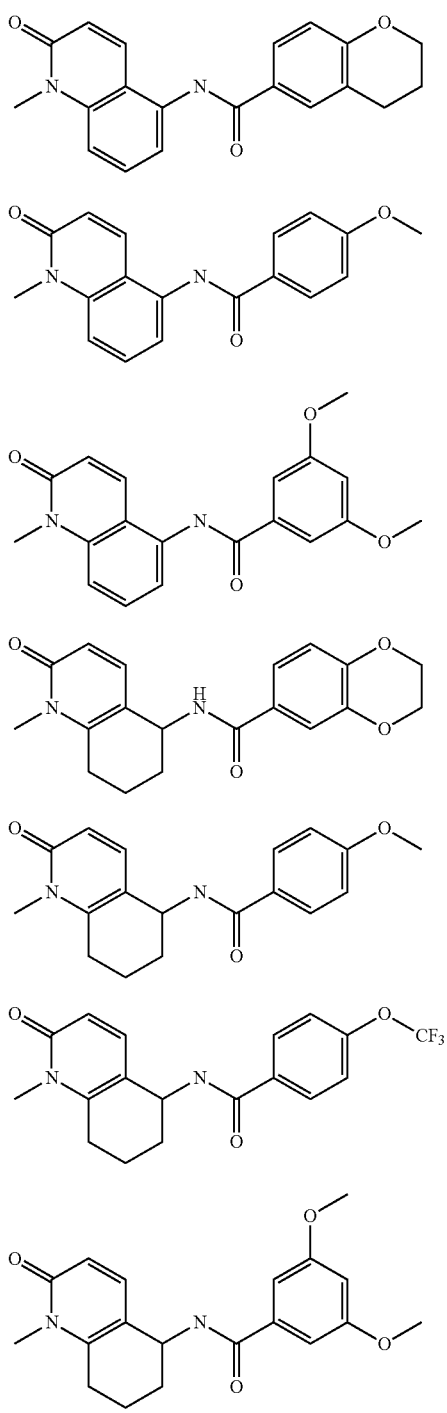

or a pharmaceutically acceptable salt, solvate or prodrug thereof.

32. A TAF1 inhibitor for use in therapy, wherein the TAF1 inhibitor is to be administered in combination with a BRD4 inhibitor.
33. A BRD4 inhibitor for use in therapy, wherein the BRD4 inhibitor is to be administered in combination with a TAF1 inhibitor.
34. A TAF1 inhibitor for use in the treatment or prevention of cancer, wherein the TAF1 inhibitor is to be administered in combination with a BRD4 inhibitor.
35. A BRD4 inhibitor for use in the treatment or prevention of cancer, wherein the BRD4 inhibitor is to be administered in combination with a TAF1 inhibitor.
36. A pharmaceutical composition comprising a TAF1 inhibitor and a BRD4 inhibitor.
37. The pharmaceutical composition of item 36 for use in therapy.
38. The pharmaceutical composition of item 36 for use in the treatment or prevention of cancer.
39. Use of a TAF1 inhibitor and a BRD4 inhibitor in the preparation of a medicament for the treatment or prevention of cancer.
40. A method of treating or preventing cancer, the method comprising administering a TAF1 inhibitor in combination with a BRD4 inhibitor to a subject in need thereof.
41. The TAF1 inhibitor for use according to item 32 or 34 or the BRD4 inhibitor for use according to item 33 or 35 or the pharmaceutical composition of item 36 or the pharmaceutical composition for use according to item 37 or 38 or the use of item 39 or the method of item 40, wherein the TAF1 inhibitor is a compound as defined in any one of items 1 to 20.
42. The TAF1 inhibitor for use according to item 32, 34 or 41 or the BRD4 inhibitor for use according to item 33, 35 or 41 or the pharmaceutical composition of item 36 or 41 or the pharmaceutical composition for use according to item 37, 38 or 41 or the use of item 39 or 41 or the method of item 40 or 41, wherein the BRD4 inhibitor is CeMMEC2, (S)-JQ1, I-BET 151, I-BET 762, PF-1, bromosporine, OTX-015, TEN-010, CPI-203, CPI-0610, RVX-208, 812536, TG101348, LY294002, or a pharmaceutically acceptable salt, solvate or prodrug of any one of these agents.
43. The TAF1 inhibitor for use according to item 34, 41 or 42 or the BRD4 inhibitor for use according to item 35, 41 or 42 or the pharmaceutical composition for use according to item 38, 41 or 42 or the use of item 39, 41 or 42 or the method of any one of items 40 to 42, wherein said cancer is selected from prostate carcinoma, breast cancer, acute myeloid leukemia, multiple myeloma, glioblastoma, and NUT midline carcinoma.

The invention will now be described by reference to the following examples which are merely illustrative and are not to be construed as a limitation of the scope of the present invention.

EXAMPLES

Example 1

Introduction

The compelling efficacy of compounds designed to target the two bromodomains of BRD4 in cancer models, such as the pan-BET inhibitors JQ1 (Filippakopoulos et al., 2010) and I-BET-15 (Seal et al., 2012), has prompted the development of drug candidates for these protein interaction modules that are now undergoing clinical trials (Filippakopoulos et al., 2014). Despite the large number of competing clinical programs, the mechanistic and chemical diversity of currently available BRD4 inhibitors is limited (Filippakopoulos et al., Cell, 2012; Filippakopoulos et al., 2014). Furthermore, there is a lack of detailed understanding of the factors affecting BRD4 function.

The inventors set out to design a strategy allowing the unbiased scouting of high diversity chemical space for modulators of a BRD4-dependent inactive chromatin state. In the background of the human haploid cell line KBM7

(Andersson et al., 1995), allowing unambiguous monoallelic genetic configurations, the RFP (Red Fluorescent Protein) gene was integrated in heterochromatic loci which are specifically activated by BRD4 inhibition. A high-diverse compound library of 89,355 small molecules was then chosen and compounds were selected for their ability to reactivate RFP expression. The efficient identification of many BRD4 inhibitors, including all the BET inhibitors in this library, validated the experimental strategy. Importantly, the setup allowed the identification of small molecules that efficiently induced RFP expression but failed to bind BRD4, indicating a novel mechanism of action. As detailed further below, the inventors were able to show that one such compound, CeMMEC1, functioned by binding the second bromodomain of the transcription initiation factor TAF1. Investigation of the properties of this new compound and its derivatives enabled the inventors to demonstrate a strong synergy between the targeting of TAF1 and BRD4, which resulted in efficient killing of BRD4-dependent cancer cells.

Materials and Methods

Cell Culture and Transfection

The human chronic myelogenous leukemia cell line KBM7 was cultured in Iscove's Modified Dulbecco's Medium (IMDM, Gibco), supplemented with 10% Fetal Bovine Serum (FBS; Gibco) and 100 units/ml streptomycin and penicillin (both from Gibco). The human embryonic kidney cell line HEK293T was cultured in Dulbecco's Modified Eagles Medium (DMEM, Gibco) supplemented with 10% FBS and 100 units/ml streptomycin and penicillin. The peripheral blood human acute monocytic leukemia cell line THP1 and the adenocarcinoma (non small lung cancer) cell lines H23 were cultured in RPMI-1640 (Roswell Park Memorial Institute, Gibco) supplemented with 10% FBS and 100 units/ml streptomycin and penicillin. All the mentioned cell lines were incubated in 5% $CO_2$ atmosphere at 37° C.

HEK293T cells were transfected with Lipofectamine 2000 (Invitrogen) according to the manufacturer's instructions.

Used plasmids were:

LZRS-RFP-ires-ZEO.

pFlag-CMV2-Brd4 (Addgene plasmid #22304).

Live Cell Imaging and Picture Quantification

Cells were seeded on clear flat bottom 96-well or 384-well plates (Corning) and treated with the indicated compounds for the specified conditions. Live cell imaging pictures were taken with the Operetta High Content Screening System (PerkinElmer), 20× objective and non-confocal mode.

RFP quantification was done using the Harmony software (PerkinElmer) for nuclei detection and analysis, adapted for the nucleus diameter range of the specific cell line used (e.g. KBM7 nucleus diameter 13 μM). Only RFP-positive nuclei were detected and counted.

Apoptotic cells were detected using the Annexin V-FITC Apoptosis detection kit (Abcam) according to the manufacturer's instruction. Apoptosis quantification was performed with the Harmony software (PerkinElmer) for nuclei and cytoplasm detection and analysis, adapted for the nucleus diameter range and cell shape of the specific cell line used.

Western Blot

Proteins were separated on polyacrylamide gels with SDS running buffer (50 mM Tris, 380 mM Glycine, 7 mM SDS) and transferred to nitrocellulose blotting membranes. All membranes were blocked with blocking buffer (5% (m/v) milk powder (BioRad) in TBST (Tris-Buffered Saline with Tween: 50 mM Tris (tris (hydroxymethyl)aminomethane), 150 mM NaCl, 0.05% (v/v) Tween 20, adjusted to pH 7.6)). Proteins were probed with antibodies against BRD4 (ab128874, 1:1000, Abcam), Actin (ab16039, 1:1000, Abcam), c-MYC (ab32072, 1:1000, Abcam), Flag (F1804, 1:1000, Sigma), BRD9 (ab49313, 1:1000, Abcam) and Taf1 (sc-735, 1:1000, Santa Cruz), detected by HRP (horseradish peroxidase) conjugated donkey anti-rabbit IgG antibody (ab16284, 1:5000, Abcam) or donkey anti-mouse IgG antibody (Pierce) and visualized with the Pierce ECL Western Blotting substrate (Amersham), according to the provided protocol.

RNA Extraction PCR and QPCR

RNA extraction was performed with TRIzol Reagent (Life Technologies) according to the manufacturer's protocol and Reverse Transcription (RT) was performed using the High Capacity cDNA Reverse Transcription Kit (Applied Biosystems) following the standard protocol.

Standard PCR was performed using Pfu DNA Polymerase (Fermenta) according to the standard conditions.

Standard PCR primers used:

```
WT-KBM7 genome
(Sigma; forward 5'-CAGTTCCGCTACACGTGCTG, reverse 5'-CGTGGACCCTTAAAGAGAAGGT)

REDS3 genome
(Sigma; forward 5'-CAGTTCCGCTACACGTGCTG, reverse 5'-GCGCATGAACTCCTTGATGAC)

Insulin_promoter
(Sigma; forward 5'-CTCTCCTTGAGATGTTAATGTGGCT, reverse 5'-CACACGGAAGATGAGGTCCGAGTGG)
```

QPCR was performed using the Power SYBR Green Master mix (Invitrogen) as described in the manufacturer's protocol.

QPCR primers used:

```
BRD4
(Sigma; forward 5'-CAGGAGGGTTGTACTTATAGCA, reverse 5'-CTACTGTGACATCATCAAGCAC).

c-MYC
(Sigma; forward 5'-GAAGGTGATCCAGACTCTGACCT, reverse 5'-CTTCTCTCCGTCCTCGGATTCT).

Actin
(Sigma; forward 5'-ATGATGATATCGCCGCGCTC, reverse 5'-CCACCATCACGCCCTGG).

BRD3
(Sigma; forward 5'-AAGAAGAAGGACAAGGAGAAGG, reverse 5'-CTTCTTGGCAGGAGCCTTCT).

TAF1
(Sigma; forward 5'-TGCCCAGGAGATTGTGAACG, reverse 5'-GGCTTAGCCTGAGGCGTG).

CREBP
(Sigma; forward 5'-AGCAGCAGCTGGTTCTACTG, reverse 5'-CACAATGGGCAACTTGGCAG).
```

```
EP300
(Sigma; forward 5'-GCAGTGTGCCAAACCAGATG, reverse 5'-CATAGCCCATAGGCGGGTTG).

STX2
(Sigma; forward 5'-GGCAAGAAGGAAATTGATGTTCA, reverse 5'-AGACGTTCGGTTGTGCTTCT).

RAN
(Sigma; forward 5'-GAGAAGAACCACCTTGGGTGT, reverse 5'-TCCACCGAATTTCTCCTGGC).

RFP
(Sigma; forward 5'-GGGAGCGCGTGATGAACTTC, reverse 5'-GGAAGTTCACGCCGATGAAC).
```

Real-time amplification results were normalized to the endogenous housekeeping genes Actin or GAPDH. The relative quantities were calculated using the comparative CT (Cycle Threshold) Method ($\Delta\Delta$CT Method).

Cell Cycle Assay and Cell Sorting

For cell cycle analysis, cells were fixed with 70% ethanol for 24 hours, washed with PBS/0.1%-Tween and incubated with RNase for 20 minutes. Nuclei were stained with 5 µg/ml PI (propidium iodide, Sigma) for 10 minutes prior to FACS analysis (BD FACSCalibur Flow Cytometer).

RFP-positive/negative cell sorting was performed using the FACSAria (BD Biosciences) sorter. Gates for positive or negative RFP populations were done using the appropriate RFP-positive or negative controls. RFP-positive cells (1%, very positive population) were sorted in presence of (S)-JQ1 0.5 µM 48 hours after infection. The negative population was sorted in absence of (S)-JQ1 72 hours after the first sorting (0.7%, negative, double-sorted single clones). RFP negative double-sorted clones were grown and treated with (S)-JQ1 0.5 µM several times, in order to verify their ability to express RFP only upon treatment.

FISH Assay

The RFP specific probe (RFPprobe) was PCR performed using RFP specific primers (Sigma; forward 5'-CGGT-TAAAGGTGCCGTCTCG, reverse 5'-AGGCTTCCCAG-GTCACGATG) and labeled using dig-dUTP (DIG Nick Translation Mix, Roche).

Briefly, before hybridization, slides were fixed with 3% paraformaldehyde (Merck) in PBS for 10 min, permeabilized with 0.5% Triton (Sigma) in PBS for 5 min and then immediately passed through an ethanol series (70%, 85% and 100%). The denaturation was performed in 50% formamide (Sigma) in 2×SSC buffer (Saline Sodium Citrate buffer: 0.3 M NaCl, 30 mM sodium citrate) simultaneously on nuclei and probes for 30 min at 80° C. Hybridization was done overnight in a dark humidity chamber at 37° C. The slides were washed three times in 50% formamide/2×SSC buffer and another three times with 50% 2×SSC buffer (both at room temperature), incubated with Anti-Digoxigenin-Fluorescein (Fab fragments, Roche) for 1 hour at room temperature and detected with AlexaFluor488 IgG Fraction Monoclonal Mouse Anti-Fluorescein (Jackson Laboratory). Finally, nuclei were counterstained with 4',6-diamidino-2-phebyl-indole (DAPI, Sigma). Images were taken using a Leica DMI6000b inverted confocal system and a 63× 1.30 ACS Apo lens, and edited using Leica LAS AF software (Leica Microsystems) and Fiji (ImageJ).

Protein Expression of GST-Tagged BRD4

GST-BRD4 was extracted and purified from BL21 (DE3) E. coli cells (New England BioLabs) and heat shock transformed with p5068 pGEX-6P-1 (full length BRD4 with GST-tag; Addgene). Transformed cells were inoculated into a LB agar plate with ampicillin 100 mg/ml. One colony was selected and grown in LB broth (ampicillin 100 mg/ml) in a shaker (250 g) at 37° C. until an OD (optical density) value of 0.8 at 600 nm was reached. Isopropyl-3-D-thiogalactopyranoside (IPTG; Sigma) was added to a final concentration of 0.3 mM, cultures were further grown for 3 hours at 37° C. Cells were harvested by centrifugation (6000 g for 15 min at 4° C.) and resuspended in cold lysis buffer (20 mM Tris-HCl pH 7.5, 0.5 M NaCl, 5 mM EDTA, 1% Igepal) containing 2.5 mg/ml Lysozyme (Fluke), 0.1 mg/ml DNase I (Roche), 5 mM β-mercaptoethanol and an appropriate amount of protease inhibitor cocktail (Roche). Cells were disrupted by gentle sonication (2 cycles, 10 s) on ice and centrifuged (9000 g for 20 min at 4° C.). BRD4 proteins carrying the GST-tag were purified under native conditions using Glutathione Sepharose 4B beads (GE Healthcare). The GST-tagged proteins were eluted with elution buffer (10 mM Glutathione, 50 mM Tris, pH 8.0, plus appropriate amount of protease inhibitor cocktail). The purity of the protein preparations was assessed by SDS-PAGE in 10% polyacrylamide gel, under reducing conditions.

AlphaLISA Assay

The Amplified Luminescent Proximity Homogenous Assay (AlphaLISA©) is the homogenous and chemiluminescence-based method, used to explore the direct interaction of the identified small molecules with BRD4 and therefore, measure the $IC_{50}$ values of the direct BRD4 inhibitors.

Briefly, in this assay, the biotinylated histone peptide substrate is captured by streptavidin-coupled donor beads. The GST-tagged bromodomain is recognized and bound by an anti-GST antibody conjugated with an acceptor bead. In absence of an inhibitor, the bromodomain binds to histone peptide substrate. The excitation (680 nm wavelength) of a donor bead provokes the release of a singlet oxygen molecule ($^1O_2$) that triggers a cascade of energy transfer in the acceptor bead, resulting in a sharp peak of light emission at 615 nm. The event of a signal (alpha count) can only take place when the interaction partners are in proximity (<200 nm). The presence of a compound that blocks the histone-docking site (inhibitor) results in the dropping of emission.

The AlphaLISA was performed for both bromodomains of BRD4 using the BRD4 (BD1) Inhibitor Screening Kit (BPS Bioscience) and BRD4 (BD2) Inhibitor Screening Kit (BPS Bioscience) following the manufacturer's protocol. For the GST full length BRD4 purified from BL21 cells, a mixture of acetylated substrates from the BD1 and BD2 Inhibitor Screening Kit reported above was used.

Compounds were tested at a final assay concentration of 10 µM in duplicates. To determine IC50 values, two-fold serial dilutions (12 points; 50 µM to 0.02 µM) of test inhibitors were prepared. Reaction was initiated by adding one of the two bromodomains (BD1 or BD2) or the GST full length BRD4. After 30 minutes, GSH (Glutathione) Acceptor beads (PerkinElmer) were added and after another incubation time of 30 minutes, Streptavidin-conjugated donor beads (PerkinElmer) were added. Alpha counts were read by EnVision 2104 Multilabel Reader (PerkinElmer).

Compound Screening

REDS3 cells were treated with the compound library (89,355 diverse compounds). The increase of RFP fluorescence, detected with the Operetta High Content Screening System (PerkinElmer), 20× objective and non-confocal mode, was used as read-out.

Briefly, the screening was divided in three parts called respectively 1) primary screening, 2) follow up and 3) validation. During the primary screening REDS3 cells were treated with 10 µM of every compound, and live cell imaging pictures were taken in order to assess their ability to induce RFP expression 24 hours later. From this primary screening 1,286 small molecules were selected as hits and re-screened in the follow up part, in which REDS3 and WT-KBM7 were treated in 3-point dose response in order to exclude autofluorescent or toxic compounds. 80 small molecules were selected as hits and used to treat WT-KBM7 and REDS3 in 8-point dose (2 fold dilution, starting from 100 µM) response and 3-point time course (24/48/72 hours) in order to carefully select the best true hits (time- and dose-dependent RFP expression/no autofluorescence). UPLC-MS analysis was done to confirm purity and the correct mass of the small molecules selected; finally, 22 small molecules were chosen as screening hits.

Compound Synthesis

Compounds CeMMEC1 and CeMMEC2 were purchased from AKos GmbH (Steinen, Germany). Compound A1 was purchased from InterBioScreen Ltd. (Chernogolovka, Russia). Compounds A2, A3, A4 and A5 were purchased from ChemDiv (San Diego, USA). Synthesis of all other analogs was carried out by Enamine Ltd. (Kiev, Ukraine) following the scheme below:

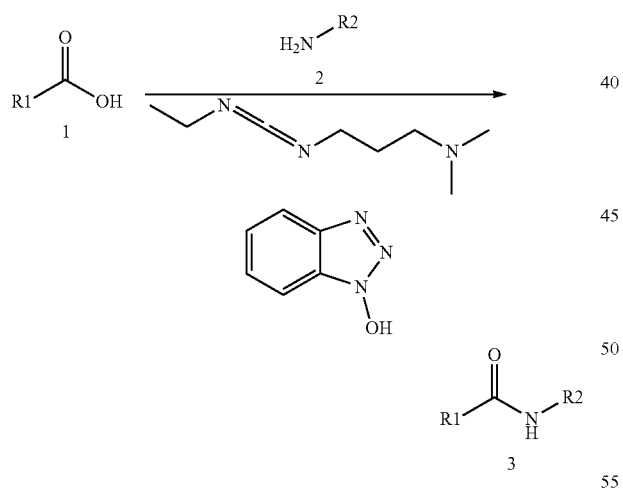

A mixture of acid 1 (1.1 mmol), amine 2 (1.0 mmol), EDC (1.1 mmol), and HOBt (1.6 mmol) in DMF (1 ml) was stirred at room temperature for 24 hours. Chloroform (6 ml) and water (8 ml) was added, organic layer was separated, washed with water (8 ml) twice, dried over $Na_2SO_4$ and evaporated. The crude residue was purified by reversed phase (C-18) chromatography with gradient elution (methanol-water) to yield pure 3.

All compounds were quality controlled by LC-MS, requiring a minimum purity of 90%.

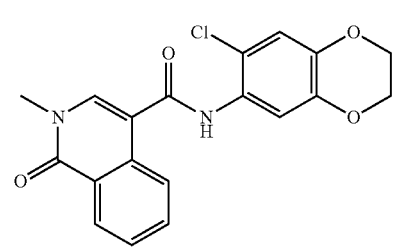

Compound 1

MS (m/z): [M+H]+ calcd. for $C_{19}H_{15}ClN_2O_4$ 371.0804, found 371.1.

Yield: 3%

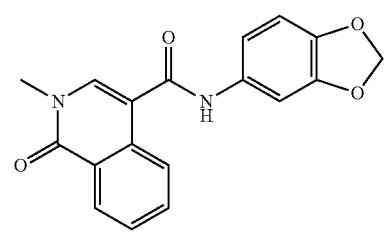

Compound 3

$^1$H NMR (400 MHz, DMSO_d6) δ ppm 2.50 (br s, 12H) 3.39 (br s, 5H) 3.59 (s, 3H) 3.66 (s, 1H) 6.01 (s, 2H) 6.91 (br d, J=8.39 Hz, 1H) 7.13 (br d, J=8.39 Hz, 1H) 7.43 (s, 1H) 7.57 (br t, J=7.46 Hz, 1H) 7.76 (br t, J=7.46 Hz, 1H) 8.06 (s, 1H) 8.15 (br d, J=7.93 Hz, 1H) 8.29 (br d, J=7.93 Hz, 1H) 10.26 (br s, 1H); MS (m/z): [M+H]+ calcd. for $C_{18}H_{14}N_2O_4$ 323.1026, found 323.2.

Yield: 10%

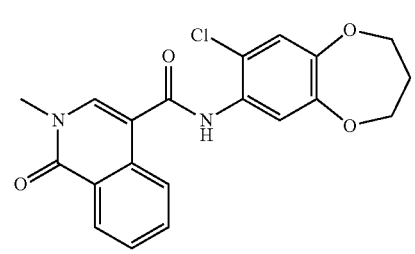

Compound 4

MS (m/z): [M+H]+ calcd. for $C_{20}H_{17}ClN_2O_4$ 385.094961, found 385.0.

Yield: 3%

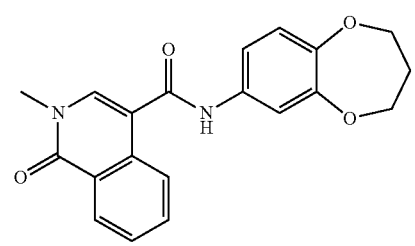

Compound 5

$^1$H NMR (400 MHz, DMSO_d6) δ ppm 2.10 (br s, 2H) 2.50 (br s, 24H) 3.33 (s, 9H) 3.59 (s, 3H) 4.10 (dt, J=17.60, 4.72 Hz, 4H) 6.93-7.00 (m, 1H) 7.23-7.30 (m, 1H) 7.44 (br s, 1H) 7.52-7.61 (m, 1H) 7.76 (br t, J=7.46 Hz, 1H) 8.05 (s, 1H) 8.13 (br d, J=7.93 Hz, 1H) 8.29 (br d, J=7.93 Hz, 1H) 10.25 (s, 1H); MS (m/z): [M+H]+ calcd. for $C_{20}H_{18}N_2O_4$ 351.1339, found 351.2.

Yield: 39%

Compound 6

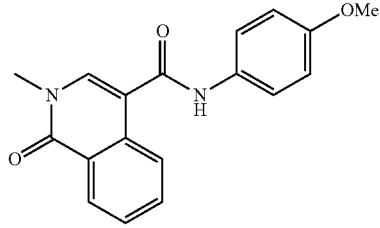

$^1$H NMR (400 MHz, DMSO_d6) δ ppm 2.50 (br s, 13H) 3.33 (br s, 7H) 3.59 (s, 3H) 3.75 (s, 3H) 6.94 (br d, J=8.39 Hz, 2H) 7.57 (br t, J=7.46 Hz, 1H) 7.64 (br d, J=8.39 Hz, 2H) 7.76 (br t, J=7.69 Hz, 1H) 8.06 (s, 1H) 8.16 (br d, J=7.93 Hz, 1H) 8.29 (br d, J=7.93 Hz, 1H) 10.21 (s, 1H); MS (m/z): [M+H]+ calcd. for $C_{18}H_{16}N_2O_3$ 309.1234, found 309.2.

Yield: 20%

Compound 8

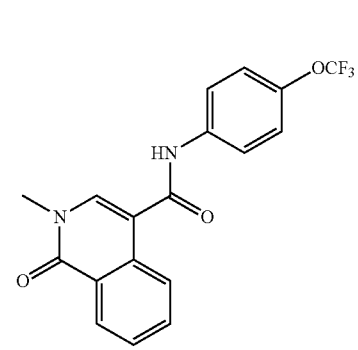

$^1$H NMR (400 MHz, DMSO_d6+CCl$_4$) δ ppm 2.49 (br s, 4H) 3.01 (s, 6H) 3.62 (s, 3H) 7.21 (br d, J=8.53 Hz, 2H) 7.50 (br t, J=7.28 Hz, 1H) 7.69 (br t, J=7.03 Hz, 1H) 7.85 (br d, J=9.03 Hz, 2H) 7.98 (s, 1H) 8.17-8.36 (m, 2H) 10.28 (s, 1H); MS (m/z): [M+H]+ calcd. for $C_{18}H_{13}F_3N_2O_3$ 363.0951, found 363.2.

Yield: 8%

Compound 10

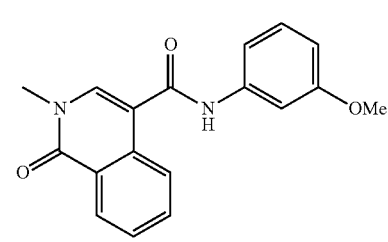

$^1$H NMR (500 MHz, DMSO-d$_6$) δ ppm 2.53-2.55 (m, 1H) 3.28-3.34 (m, 2H) 3.60 (s, 3H) 3.76 (s, 3H) 6.69 (br d, J=6.86 Hz, 1H) 7.23-7.34 (m, 2H) 7.43 (br s, 1H) 7.57 (br t, J=7.55 Hz, 1H) 7.77 (br t, J=7.55 Hz, 1H) 8.08 (s, 1H) 8.16 (br d, J=8.23 Hz, 1H) 8.30 (br d, J=8.23 Hz, 1H) 10.31 (br s, 1H); MS (m/z): [M+H]+ calcd. for $C_{18}H_{16}N_2O_3$ 309.1234, found 309.2.

Yield: 29%

Compound 12

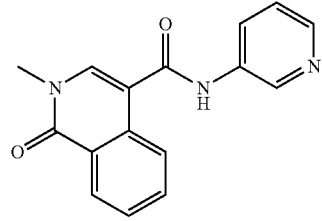

$^1$H NMR (400 MHz, DMSO_d6+CCl$_4$) δ ppm 1.21 (s, 1H) 2.46 (br s, 3H) 2.99 (s, 5H) 3.59 (s, 3H) 7.16-7.35 (m, 1H) 7.47 (br t, J=7.53 Hz, 1H) 7.66 (br t, J=7.65 Hz, 1H) 8.01 (s, 1H) 8.15-8.30 (m, 4H) 8.76 (br s, 1H) 10.27 (br s, 1H); MS (m/z): [M+H]+ calcd. for $C_{16}H_{13}N_3O_2$ 280.1081, found 280.2.

Yield: 4%

Compound 13

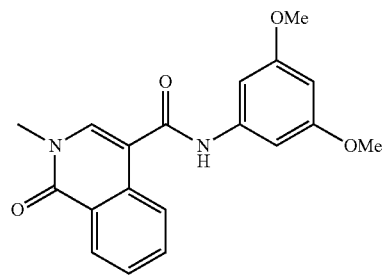

$^1$H NMR (400 MHz, DMSO_d6+CCl$_4$) δ ppm 1.25 (br s, 1H) 1.32 (br d, J=8.86 Hz, 1H) 2.41-2.58 (m, 4H) 3.03 (br s, 7H) 3.63 (s, 3H) 3.78 (s, 6H) 6.17 (br s, 1H) 7.00 (br d, J=1.87 Hz, 2H) 7.51 (br t, J=7.46 Hz, 1H) 7.70 (br t, J=7.23 Hz, 1H) 7.97 (s, 1H) 8.20-8.37 (m, 2H) 10.02 (s, 1H); MS (m/z): [M+H]+ calcd. for $C_{19}H_{18}N_2O_4$ 339.1339, found 339.2.

Yield: 37%

Compound 15

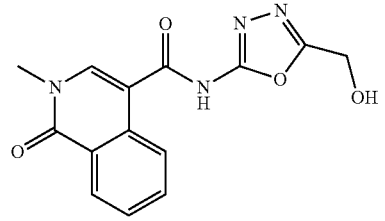

$^1$H NMR (500 MHz, DMSO-d$_6$) δ ppm 2.34-2.66 (m, 5H) 3.30-3.34 (m, 1H) 3.59 (s, 3H) 5.36 (s, 2H) 7.20 (br s, 1H) 7.57 (br t, J=7.41 Hz, 1H) 7.81 (br t, J=7.68 Hz, 1H) 8.27 (br d, J=7.68 Hz, 1H) 8.47 (s, 1H) 8.69 (br d, J=8.51 Hz, 1H);

MS (m/z): [M+H]+ calcd. for $C_{14}H_{12}N_4O_4$ 301.0931, found 301.2.

Yield: 10%

Compound 16

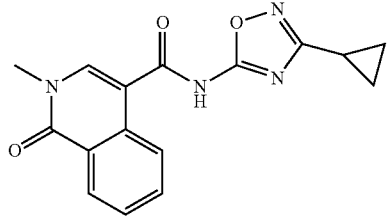

$^1$H NMR (500 MHz, DMSO-$d_6$) δ ppm 0.84-0.93 (m, 2H) 1.06 (br dd, J=8.23, 2.47 Hz, 2H) 2.08 (br s, 1H) 2.48-2.52 (m, 8H) 3.33 (s, 4H) 3.57 (s, 3H) 7.54-7.63 (m, 1H) 7.79 (br t, J=7.55 Hz, 1H) 8.25-8.35 (m, 3H) 12.21-12.37 (m, 1H); MS (m/z): [M+H]+ calcd. for $C_{16}H_{14}N_4O_3$ 311.1139, found 311.0.

Yield: 8%

Compound 24

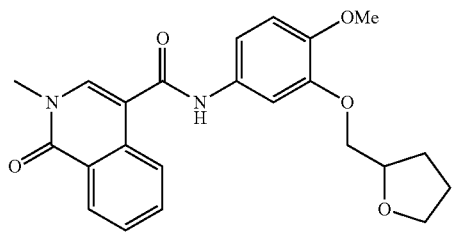

$^1$H NMR (400 MHz, CDCl$_3$) δ ppm 1.23 (br s, 1H) 1.67-2.15 (m, 4H) 3.29 (br s, 3H) 3.82 (br s, 4H) 3.90 (br d, J=6.78 Hz, 1H) 3.96-4.04 (m, 2H) 4.32 (br s, 1H) 6.84 (br d, J=8.03 Hz, 1H) 7.16 (br d, J=8.03 Hz, 1H) 7.35 (br s, 1H) 7.40-7.48 (m, 1H) 7.51 (br s, 1H) 7.62 (br t, J=6.50 Hz, 1H) 8.02 (br d, J=7.78 Hz, 1H) 8.30 (br d, J=7.28 Hz, 1H) 8.78 (br s, 1H); MS (m/z): [M+H]+ calcd. for $C_{23}H_{24}N_2O_6$ 409.1758, found 409.2.

Yield: 5%

Compound 25

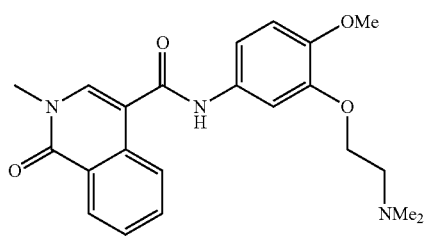

$^1$H NMR (400 MHz, DMSO_d6+CCl$_4$) δ ppm 1.25 (br s, 1H) 2.30 (s, 6H) 2.51 (br s, 3H) 2.71 (br t, J=6.10 Hz, 2H) 3.02 (br s, 3H) 3.63 (s, 3H) 3.80 (s, 3H) 4.05 (br t, J=6.24 Hz, 2H) 6.84 (br d, J=8.86 Hz, 1H) 7.21 (br d, J=8.71 Hz, 1H) 7.42-7.55 (m, 2H) 7.69 (br t, J=7.95 Hz, 1H) 7.95 (s, 1H) 8.29 (br dd, J=12.59, 8.39 Hz, 2H) 9.93 (br s, 1H); MS (m/z): [M+H]+ calcd. for $C_{22}H_{25}N_3O_4$ 396.1918, found 396.2.

Yield: 16%

Compound 26

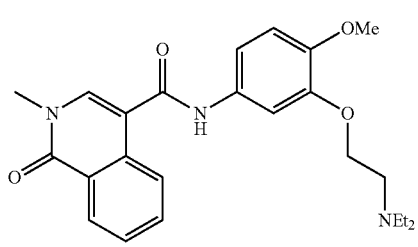

$^1$H NMR (400 MHz, DMSO_d6+CCl$_4$) δ ppm 1.05 (br t, J=7.00 Hz, 6H) 2.61 (q, J=7.00 Hz, 3H) 2.55-2.69 (m, 1H) 2.85 (br t, J=6.30 Hz, 2H) 3.02 (br s, 5H) 3.63 (s, 3H) 3.79 (s, 3H) 4.00 (br t, J=6.53 Hz, 2H) 6.83 (br d, J=8.86 Hz, 1H) 7.20 (br d, J=8.86 Hz, 1H) 7.42-7.59 (m, 2H) 7.69 (br t, J=7.46 Hz, 1H) 7.94 (s, 1H) 8.29 (br dd, J=12.36, 8.63 Hz, 2H) 9.92 (s, 1H); MS (m/z): [M+H]+ calcd. for $C_{24}H_{29}N_3O_4$ 424.2231, found 424.2.

Yield: 5%

Compound 27

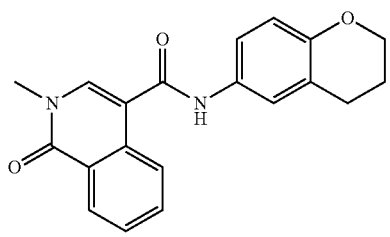

$^1$H NMR (400 MHz, Solvent) δ ppm 1.92 (br t, J=6.06 Hz, 2H) 2.50 (br s, 11H) 2.75 (br t, J=6.06 Hz, 2H) 3.33 (br s, 6H) 3.59 (s, 3H) 4.06-4.16 (m, 2H) 6.72 (br d, J=8.86 Hz, 1H) 7.35 (br d, J=8.86 Hz, 1H) 7.48 (br s, 1H) 7.56 (br t, J=7.46 Hz, 1H) 7.76 (br t, J=7.46 Hz, 1H) 8.03 (s, 1H) 8.15 (br d, J=7.93 Hz, 1H) 8.29 (br d, J=7.93 Hz, 1H) 10.11 (s, 1H); MS (m/z): [M+H]+ calcd. for $C_{20}H_{18}N_2O_3$ 335.1390, found 335.1.

Yield: 16%

Compound 29

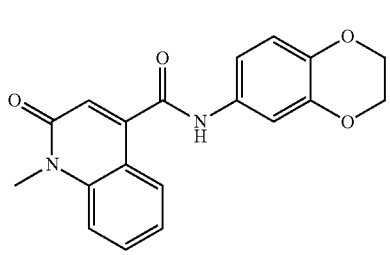

$^1$H NMR (400 MHz, DMSO_d6+CCl$_4$) δ ppm 2.41-2.61 (m, 2H) 3.04 (br s, 2H) 3.70 (s, 3H) 4.25 (br d, J=3.26 Hz, 4H) 6.64-6.84 (m, 2H) 7.16 (br d, J=8.39 Hz, 1H) 7.26 (br t, J=7.23 Hz, 1H) 7.37 (br s, 1H) 7.52 (br d, J=8.39 Hz, 1H) 7.57-7.75 (m, 1H) 7.90 (br d, J=7.46 Hz, 1H) 10.38 (br s, 1H) 12.76-12.79 (m, 1H); MS (m/z): [M+H]+ calcd. for C$_{19}$H$_{16}$N$_2$O$_4$ 337.1183, found 337.2.

Yield: 95%

Compound 30

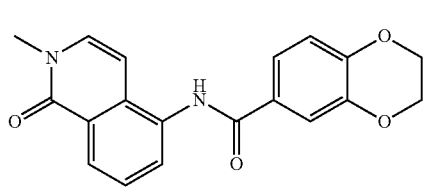

$^1$H NMR (400 MHz, DMSO_d6+CCl$_4$) δ ppm 2.41-2.58 (m, 2H) 2.96-3.05 (m, 3H) 3.08 (br s, 1H) 3.55 (s, 3H) 4.27 (br s, 1H) 4.33 (br d, J=2.33 Hz, 4H) 6.54 (br d, J=7.93 Hz, 1H) 6.91 (d, J=8.39 Hz, 1H) 7.32 (br d, J=7.46 Hz, 1H) 7.47 (br t, J=7.93 Hz, 1H) 7.52-7.63 (m, 2H) 7.70 (br d, J=7.46 Hz, 1H) 8.09-8.26 (m, 1H) 9.96 (s, 1H); MS (m/z): [M+H]+ calcd. for C$_{19}$H$_{16}$N$_2$O$_4$ 337.1183, found 337.2.

Yield: 87%

Compound 32

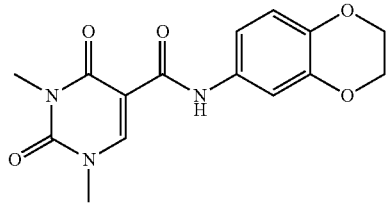

(reference)

MS (m/z): [M+H]+ calcd. for C$_{15}$H$_{15}$N$_3$O$_5$ 318.108447, found 318.2.

Yield: 90%

Compound 33

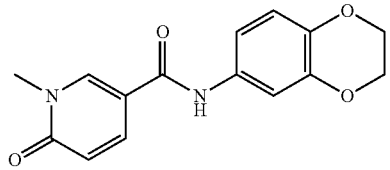

$^1$H NMR (400 MHz, DMSO_d6+CCl$_4$) δ ppm 2.51 (br s, 1H) 3.04 (s, 2H) 3.54 (s, 3H) 4.23 (br d, J=4.20 Hz, 4H) 6.38 (br d, J=9.79 Hz, 1H) 6.72 (br d, J=8.86 Hz, 1H) 7.07 (br dd, J=8.86, 2.33 Hz, 1H) 7.26 (br d, J=2.33 Hz, 1H) 7.95 (br dd, J=9.33, 2.33 Hz, 1H) 8.45 (br d, J=2.33 Hz, 1H) 9.58 (s, 1H);

MS (m/z): [M+H]+ calcd. for C$_{15}$H$_{14}$N$_2$O$_4$ 287.1026, found 287.1.

Yield: 22%

Compound 35

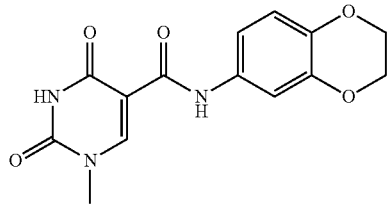

(reference)

MS (m/z): [M+H]+ calcd. for C$_{14}$H$_{13}$N$_3$O$_5$ 304.092797, found 304.0.

Yield: 88%

Compound 36

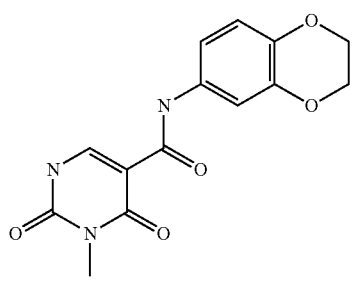

$^1$H NMR (400 MHz, DMSO_d6+CCl$_4$) δ ppm 2.51 (br s, 2H) 3.02 (br s, 3H) 3.28 (s, 3H) 4.23 (br d, J=4.20 Hz, 4H) 6.73 (br d, J=8.39 Hz, 1H) 6.92 (br dd, J=8.86, 2.33 Hz, 1H) 7.30 (br d, J=2.33 Hz, 1H) 8.26 (s, 1H) 10.75 (s, 1H); MS (m/z): [M+H]+ calcd. for C$_{14}$H$_{13}$N$_3$O$_5$ 304.0928, found 304.0.

Yield: 21%

Compound 37

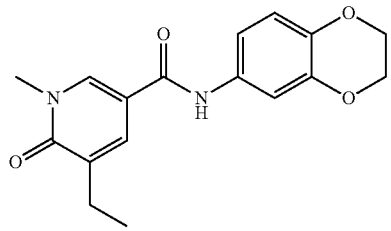

$^1$H NMR (400 MHz, DMSO_d6+CCl$_4$) δ ppm 1.20 (br t, J=7.46 Hz, 3H) 2.42-2.59 (m, 4H) 2.79 (s, 1H) 2.95 (s, 1H) 3.03 (br s, 3H) 3.50 (s, 1H) 3.55 (s, 2H) 4.24 (br d, J=4.66 Hz, 4H) 6.72 (br d, J=8.86 Hz, 1H) 7.07 (br dd, J=8.86, 2.33 Hz, 1H) 7.26 (br d, J=2.33 Hz, 1H) 7.77 (br s, 1H) 7.91 (s, 1H) 8.32 (br d, J=2.33 Hz, 1H) 9.54 (s, 1H); MS (m/z):[M+H]+ calcd. for $C_{17}H_{18}N_2O_4$ 315.1339, found 315.1.

Yield: 87%

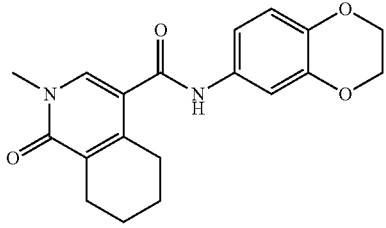

Compound 38

1H NMR (400 MHz, DMSO_d6+CCl$_4$) δ ppm 1.71 (br s, 4H) 2.43 (br s, 2H) 2.47-2.56 (m, 2H) 2.72 (br s, 2H) 3.03 (s, 2H) 3.47 (s, 3H) 4.23 (br d, J=4.20 Hz, 4H) 6.70 (br d, J=8.39 Hz, 1H) 7.05 (br d, J=8.86 Hz, 1H) 7.26 (s, 1H) 7.77 (s, 1H) 9.71 (s, 1H); MS (m/z): [M+H]+ calcd. for $C_{19}H_{20}N_2O_4$ 341.1496, found 341.1.

Yield: 91%

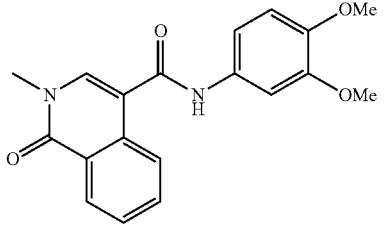

Compound 39

$^1$H NMR (400 MHz, Solvent) δ ppm 1.25 (br s, 4H) 2.51 (br s, 16H) 3.01 (br s, 27H) 3.63 (s, 3H) 3.81 (br d, J=13.99 Hz, 6H) 6.83 (br d, J=7.93 Hz, 1H) 7.19 (br s, 1H) 7.44-7.55 (m, 2H) 7.69 (t, J=7.50 Hz, 1H) 7.95 (s, 1H) 8.22-8.34 (m, 2H) 9.95 (br s, 1H); MS (m/z): [M+H]+ calcd. for $C_{19}H_{18}N_2O_4$ 339.1339, found 339.2.

Yield: 81%

RNA-Sequencing

The amount of total RNA was quantified using Qubit 2.0 Fluorometric Quantitation system (Life Technologies) and the RNA integrity number (RIN) was determined using Experion Automated Electrophoresis System (Bio-Rad). RNA-seq libraries were prepared with TruSeq Stranded mRNA LT sample preparation kit (Illumina) using Sciclone and Zephyr liquid handling robotics (PerkinElmer). Library amount was quantified using Qubit 2.0 Fluorometric Quantitation system (Life Technologies) and the size distribution was assessed using Experion Automated Electrophoresis System (Bio-Rad). For sequencing libraries were pooled and sequenced on Illumina HiSeq 2000 using 50 bp single-read. Reads were aligned with tophat (v2.0.4) with the —no-novel-juncs —no-novel-indels options (Kim et al., 2013). Gene expression was calculated as Reads Per Kb per Millions of reads (RPKMs) using RPKM_count.py from RSeQC package (Wang L. et al., 2012) and the NCBI RNA reference sequences collection (RefSeq) downloaded from UCSC (Kent et al., 2002). The enrichment calculation was done by Gene Set Enrichment Analysis (Subramanian et al., 2005; Mootha et al., 2003).

TAF1 Binding Assay

TAF1 binding assays were conducted using the EPIgeneous™ Binding Domain kit B (Cisbio Bioassays) according to manufacturer's instructions. Binding was determined by the displacement of an acetylated biotin-peptide from a GST tagged TAF1 protein using HTRF with a Eu3+ conjugated GST antibody donor and streptavidin conjugated acceptor. Compounds were dispensed into assay plates, ProxiPlate-384 Plus (Perkin Elmer) using an Echo 525 Liquid Handler (Labcyte). Binding assays were conducted in a final volume of 20 μl with 5 nM TAF1-GST, 50 nM peptide (SGRGK (ac)GGK (ac)GLGK (ac)GGAK (ac)RHRK (biotin)-acid), 6.25 nM Streptavidin-XL665, 1:200 Anti-GST-Eu3+ cryptate and 0.1% DMSO. Assay reagents were dispensed into plates using a Multidrop combi (Thermo Scientific) and incubated at room temperature for 3 hours. Fluorescence was measured using a PHERAstar microplate reader (BMG) using the HTRF module with dual emission protocol (A=ex. 320 nm em. 665 nm, B=ex. 320 nm em. 620 nm). Raw data were processed to give an HTRF ratio (channel A/B*10000), which was used to generate IC50 curves.

Protein Expression and Purification of TAF1 Second Bromodomain

TAF1 second bromodomain (Uniprot P21675, residues 1501-1634) was cloned into a pET28 derived expression vector, pNIC28-Bsa4 using ligation independent cloning. Colonies transformed in competent *E. coli* BL21 (DE3)-R3-pRARE2 cells (phage-resistant derivative of BL21 (DE3) strain), with a pRARE plasmid encoding rare codon tRNAs were grown overnight at 37° C. in 10 ml of Terrific broth medium (Sigma) with 50 μg/ml kanamycin and 34 μg/ml chloramphenicol. Cells were grown at 37° C. in TB from overnight cultures until A600 reached between 0.8-1.1, then the media was cooled and 0.2 mM Isopropyl-β-D-thiogalactopyranoside (IPTG) was added to induce the protein expression at 18° C. for 16 hours. The bacteria were harvested by centrifugation (JLA 8,100 rotor Beckman Coulter Avanti J-20 XP centrifuge) and were frozen at −20° C. Cell expressing 6×His tagged TAF1 second bromodomain were re-suspended in lysis buffer (20 mM Hepes pH 7.5, 500 mM NaCl, 10 mM Imidazole, 5% glycerol and 0.2 mM TCEP (Tris (2-carboxyethyl)phosphine hydrochloride) in the presence of protease inhibitors cocktail (1 μl/ml) and lysed using an EmulsiFlex-C5 high pressure homogenizer (Avestin-Mannheim, Germany) at 4° C. The lysate was cleared by centrifugation (14,000×g for 1 hour at 4° C.). After centrifugation, the supernatant was loaded onto the nickel column and eluted in an imidazole linear gradient. The eluted protein was collected and treated overnight with TEV protease at 4° C. to remove the N terminal tag. Digested protein was loaded onto a nickel column again to remove the non-cleaved protein and the hexa-histidine TEV used. The flow through containing the untagged protein was collected and further purified through a size exclusion chromatography in 20 mM Hepes pH 7.5, 500 mM NaCl, 5% glycerol and 0.2 mM TCEP (HiLoad 16/60 Superdex 75 GE Healthcare Life Sciences). Similarly, GST-tagged TAF1 second bromodomain was purified using a 5 ml Glutathione Sepharose Fast Flow column with elution buffer of 50 mM Tris pH8, 10 mM reduced glutathione. Gel filtration (HiLoad 16/60 Superdex 200) chromatography was performed as the final purification step. The correct mass and purity for both constructs were confirmed by an Agilent 1100 Series LC/MSD TOF (Agilent Technologies Inc. Palo Alto, Calif.).

Isothermal Titration calorimetry

Calorimetric experiments were performed on a VP-ITC micro-calorimeter (MicroCal™, LLC Northampton, Mass.). TAF1 (2) was buffer exchanged by dialysis into buffer 20 mM Hepes pH 7.5, 150 mM NaCl, and 0.5 mM TCEP. All measurements were carried out at 293.15 K while stirring at 286 rpm. The micro syringe was loaded with a protein solution of 295 µM, the compound solution was prepared at 25 µM and 2 ml for the cell. All injections were performed using an initial injection of 2 µl followed by 34 injections of 8 µl with a duration of 16 seconds per injection and a spacing of 240 seconds between injection. The data were analysed with the MicroCal ORIGIN software package employing a single binding site model. The first data point was excluded from the analysis. Thermodynamic parameters were calculated ($\Delta G = \Delta H - T \Delta S = -RT \ln K_B$ where $\Delta G$, $\Delta H$ and $\Delta S$ are the changes in free energy, enthalpy and entropy of binding, respectively).

Molecular Modeling

The crystal structures of the second bromodomain of TAF1, of ATAD2 and of BRD4 were downloaded from the RCSB protein data bank (pdb:4qst, pdb:3uv4 and pdb:3mxf). The structures were corrected, protonated and energy minimized using the LigX workflow of the molecular modeling software MOE (Molecular Operating Environment (MOE), 2014; Chemical Computing Group Inc., 1010 Sherbooke St. West, Suite #910, Montreal, QC, Canada, H3A 2R7). The hit compounds were prepared with the washing tool in MOE.

For binding pose prediction, the template-based docking protocol of MOE was used. CeMMEC1 was docked into the crystal structure of the second bromodomain of TAF1 (pdb:3uv4) (Filippakopoulos et al., *Cell,* 2012) using the atom positions of 1-methylquinolin 2-one bound to the bromodomain of ATAD2 (pdb:4qst) (Chaikuad et al., 2014) as template for pose prediction (Picaud et al., 2015). Similarly, CeMMEC2 was docked into a crystal structure of JQ1 bound to BRD4 (pdb:3mxf) (Filippakopoulos et al., 2010), with the triazole ring serving as pose prediction template.

Results

A Cellular Reporter for Detection of Functional BRD4 Inhibition

The inventors aimed to generate a cellular reporter system that rapidly responds to epigenetic changes with a gain of signal and is optimally suited to both chemical and genetic screens. Therefore, they developed a strategy of targeting a reporter construct to heterochromatic loci in KBM7 cells, a chronic myeloid leukaemia cell line with a near-haploid karyotype (Andersson et al., 1995) (see FIG. 1a). To identify such BRD4-repressed loci in an unbiased way, KBM7 cells were pre-incubated with the potent and selective BET bromodomain inhibitor (S)-JQ1 at a concentration that was sufficient to provoke chromatin reorganization, c-MYC repression (see FIG. 6a) and partial cell cycle arrest, while not causing apoptosis (see FIG. 6b). (S)-JQ1-treated cells were then infected with a retrovirus for the expression of RFP and a strategy of double FACS sorting was applied to obtain a population of cells that express RFP in the presence of (S)-JQ1 and repress the transgene after withdrawal of the compound (see FIGS. 1a and 1b).

Three clones were isolated as Reporters for Epigenetic Drug Screening (REDS1, REDS2 and REDS3), which expressed RFP in response to (S)-JQ1 (see FIG. 6c). Because of its strong and uniform RFP intensity, clone REDS3 was selected for further validation and experiments. The treatment of REDS3 cells with (S)-JQ1 induced a clear and robust increase of RFP expression detected by flow cytometry (see FIG. 1c), live cell imaging (see FIG. 6c) and real time PCR (RT-PCR) (see FIG. 6d). In addition to RFP, the zeocin resistance gene present on the retroviral vector was also upregulated (RT-PCR data, FIG. 6e). Moreover, RFP expression was not caused by the partial cell cycle arrest induced by (S)-JQ1, as the synchronization of REDS3 in different phases of the cell cycle did not increase the number of RFP-positive cells (see FIG. 6f). Recently, the activation of the LTR (Long Terminal Repeat) of HIV-1 (Human Immunodeficiency Virus-1) has been reported to be stimulated by (S)-JQ1, and the inhibition of BRD4 potentiates the action of known transcriptional HIV-1 reactivating compounds, such as PMA (phorbol myristate acetate) or PHA (phytohemagglutinin) (Zhu et al., 2012; Banerjee et al., 2012). To rule this out as a possible mechanism of RFP expression, REDS3 cells were treated with PMA, PHA or a combination of each of them with (S)-JQ1. No increase of RFP-positive nuclei was observed with these compounds (see FIG. 6g). Therefore, RFP expression was likely due to the effect of (S)-JQ1 on the locus of insertion rather than the inserted LTR.

(S)-JQ1, like almost all BRD4 inhibitors, targets the entire BET bromodomain family (BRD2, BRD3, BRD4, BRDT) with comparable potency in addition to very weak interaction with a few other human bromodomains (Filippakopoulos et al., 2010). To clarify which BET target is responsible for RFP repression and rule out off-target effects, all the (S)-JQ1 targets were knocked down individually in the REDS3 clone and RFP-positive cells were quantified by flow cytometry. Only the downregulation of BRD4 resulted in an increase of RFP-positive nuclei (see FIG. 1d). This effect was also visible by live cell imaging (see FIG. 1e) and accompanied by increased levels of RFP mRNA, not observed for instance following BRD3 downregulation (see FIG. 6h). Thus, it has been possible to create an experimental system allowing for a focused phenotypic screen for perturbations, be they genetic, pharmacological or metabolic, resulting in release from the BRD4-driven heterochromatin state.

BRD4 Inhibition Upregulates Genes Flanking Super-Enhancer Regions

To further validate the REDS3 clone, FISH (fluorescence in situ hybridization) was performed and the presence of a single RFP insertion per cell was confirmed (see FIG. 2a). The RFP probe was preferentially located in proximity to the nuclear membrane (see FIG. 2b), indicating RFP heterochromatin localization (Schermelleh et al., 2008; Towbin et al., 2012). A sequencing approach was used to map the RFP locus to region 12q24.33, located less than 3 Mb from the telomere of chromosome 12 (see FIG. 2c). The sequencing data were confirmed by PCR using specific pairs of genomic primers for wild-type (WT) and REDS3 KBM7 cells (see FIG. 2d). Less than 5 kb upstream of the RFP insertion is the STX2 gene, which is lowly expressed in KBM7 (RNA-seq (RNA sequencing) data; RPKM<1) and flanked by heterochromatin regions (*Nature* 2012, 489, 57-74). In contrast, the gene RAN, located 35 kb downstream of the RFP locus, is robustly expressed in KBM7 and has previously been described as a BRD4 target gene (Nagarajan et al., 2014). Interestingly, the region between STX2 and RAN is enriched in repeated enhancer sequences (ENCODE), endorsing the hypothesis of a super-enhancer (Pott et al., 2015; Whyte et al., 2013) controlling the expression of RAN. Even though BRD4 has been considered a transcriptional activator, REDS cells respond to BRD4 inhibition with activation of RFP. It was therefore asked whether BRD4 inhibitors directly upregulated other genes. According to RNA-seq of KBM7 cells treated for 24 hours with 1 µM (S)-JQ1, 133 genes were significantly upregulated more than two-fold (see FIG. 2e). Other cell lines (MOLM-13, KASUMI-1, MV4-11, MOLT-3, MEG-01, K-562) responded similarly, and e.g. in MOLM- 13 cells 172 genes were upregulated after only 2 hours with (S)-JQ1. Remarkably, functional annotation (Huang et al., Nat. Protoc., 2009, 4, 44-57; Huang et al., Nucleic Acids Res., 2009, 37, 1-13) of the (S)-JQ1 upregulated gene set revealed a strong cell line-independent enrichment of genes involved in chromatin remodelling (see FIG. 2f), particularly histone genes, corroborating the hypothesis of a global chromatin reorganization following BRD4 inhibition.

The expression of the genes proximal to the RFP insertion site was then checked in WT-KBM7 cells treated with (S)-JQ1, in order to see if a chromatin remodelling process was occurring at this locus when inhibiting BRD4. In line with the inventors' hypothesis, RAN expression decreased while STX2 mRNA levels increased upon (S)-JQ1 treatment (see FIG. 2g), indicating that BRD4 inhibition not only results in the reduced expression of RAN, but also raises the transcription of STX2.

Screening for Functional BRD4 Inhibitors

Although BRD4 is well studied, currently available inhibitors are of limited structural and mechanistic diversity (Filippakopoulos et al., 2014; Filippakopoulos et al., Bioorganic Med. Chem., 2012), and druggable targets upstream or downstream of BRD4 have remained elusive. The inventors aimed to screen for small molecules able to functionally inhibit BRD4. In order to confirm the specificity of the reporter detecting BRD4 inhibition, and not any other epigenetic pertubations, REDS3 was treated with several chromatin-targeted molecules. Within this small panel of compounds, only BET inhibitors were able to activate RFP expression (see FIG. 3a). With the high specificity of this reporter cell line confirmed, a large live cell imaging screen was performed, testing 89,355 small molecules (see FIGS. 7a and 10) for their ability to induce the expression of RFP in REDS3 cells after 24 hours. 0.5 µM (S)-JQ1 was used as positive control, as this was the lowest concentration causing full activation of RFP signal (see FIG. 7b) and an excellent Z'-factor (Running et al., 1999) (see FIGS. 7c and 10). Following hit validation and elimination of autofluorescent compounds, 22 compounds were confirmed as screening hits (see FIGS. 3b and 11). Remarkably, all BRD4 inhibitors contained in the compound library ((S)-JQ1 (Filippakopoulos et al., 2010), PFI1 (Fish et al., 2012), I-BET151 (Seal et al., 2012), I-BET-762 (Mirguet et al., 2013), Bromosporine, OXT015, RVX208 (McLure et al., 2013), BI-2536 (Ciceri et al., 2014) and TG-101348 (Ciceri et al., 2014)) were part of this group, underscoring the validity of the setup. 13 compounds were new, among which the inventors suspected new BRD4-inhibition scaffolds or even agents with new mechanism of action. RT-PCR for c-MYC revealed that two out of those small molecules were capable of reducing the expression of this oncogene in a dose-dependent manner to a level comparable to (S)-JQ1 treatment (see FIGS. 3c and 11). These two compounds were structurally distinct from (S)-JQ1 and all the other BRD4 inhibitors. The inventors named them CeMM Epigenetic Compounds CeMMEC1 and CeMMEC2 (see FIG. 3d). REDS3 cells treated with CeMMEC1 and CeMMEC2 expressed RFP detected by live cell imaging in a dose-dependent manner (see FIGS. 7d and 7e). Transcriptome-wide effects of CeMMEC1 and CeMMEC2 were measured and compared to (S)-JQ1. While the number of transcripts regulated by CeMMEC1 and CeMMEC2 is lower than for (S)-JQ1, there is a significant overlap of the altered gene sets (see FIG. 7f) and a good correlation between the regulated genes (see FIG. 7g). Overall these data indicate that these two compounds belong to new chemical structural classes of functional BRD4 inhibitors. BRD4 inhibitors are mainly developed for applications in oncology, where they reduce the proliferation of certain cancer cells. Therefore, the inventors treated THP1 cells, a human acute monocytic leukemia cell line sensitive to the inhibition of BRD4, with (S)-JQ1, CeMMEC1 and CeMMEC2 and analyzed cell cycle profiles and induction of apoptosis after 48 and 72 hours respectively. The cell cycle assay showed a clear and dose-dependent decrease of the number of cells in S-phase, indicative of G1-phase cell cycle arrest with all three compounds (see FIG. 3e). Moreover, all compounds induced apoptosis, as judged by AnnexinV staining (see FIG. 3f). In terms of potency, (S)-JQ1 showed the strongest effects, followed by CeMMEC2 and CeMMEC1.

Molecular Characterization of Functional BRD4 Inhibitors

To investigate whether CeMMEC1 and CeMMEC2 inhibit BRD4 through direct physical engagement, their ability to compete for binding of the BRD4 bromodomains to an acetylated histone peptide was tested in an Amplified Luminescent Proximity Homogenous Assay (AlphaLISA) immunoassay (Bielefeld-Sevigny, 2009). CeMMEC1 was neither able to bind the first nor the second bromodomain of BRD4, as no decrease of fluorescence was observed when this compound was added to the assays (see FIG. 4a). In contrast, CeMMEC2 bound both bromodomains of BRD4, comparably to (S)-JQ1 (see FIG. 4a), when used at 10 µM. Dose response AlphaLISA assays performed with full length BRD4 (GST-BRD4) showed that CeMMEC2 has an IC50 of 0.9 µM compared to 0.2 µM of (S)-JQ1 (see FIG. 4b). Similar results were obtained when the individual bromodomains of BRD4 were tested separately (see FIG. 8a).

To comprehensively analyze the binding capability of CeMMEC1 and CeMMEC2 to representative bromodomain proteins, BromoScan profiles were obtained (see FIG. 4c). Similarly to other BRD4 inhibitors, CeMMEC2 not only bound BRD4 but also all other proteins of the BET family. In contrast, CeMMEC1 only bound BRD4 very weakly, in line with the AlphaLISA data. Surprisingly, this compound showed high affinity for the bromodomains of CREBBP, EP300, BRD9, and the second bromodomain of TAF1 (TAF1 (2)), also confirmed by the sub-micromolar binding constants (see FIG. 8b). Recently CREBBP and EP300 have been described as BRD4 cofactors in regulation of transcriptional control (Roe et al., 2015), while the interplay between BRD4 and BRD9 or TAF1 has not been reported yet. Since these four bromodomain containing proteins are direct targets of CeMMEC1, it was asked whether the loss of one of them could mimic BRD4 inhibition and increase RFP expression in REDS3 cells. CREBBP, EP300, BRD9 and TAF1 were knocked down in REDS3 cells, using two independent shRNA hairpins for each gene. Western Blot was performed to confirm the level of downregulation by each hairpin (see FIG. 4d). The number of RFP-positive nuclei after knockdown was quantified by live cell imaging. A significant increase of RFP-positive nuclei was observed when downregulating TAF1, whereas no increase of RFP-positive nuclei was detected with BRD9, CREBBP or EP300 downregulation (see FIG. 4e). Moreover, as chemical probes for CREBBP and EP300 have already been reported (Hay et al., 2014; Hammitzsch et al., 2015; Picaud et al., 2015), the inventors tested them in dose response to see if a further decrease of the activity of these bromodomains could raise the number of RFP-positive cells (see FIG. 4f). No RFP expression was detected using I-CBP112, the most selective CREBBP/EP300 inhibitor. CBP30 is known to bind BRD4 at high concentrations. Accordingly, doses able to inhibit CREBBP and EP300 (Hammitzsch et al., 2015) did not show any effect, while treatment with 10 µM CBP30 resulted in a 1.5 fold increase of RFP-positive cells compared to DMSO treated cells, likely due to BRD4 inhibition.

Several BRD4 inhibitors, including bromosporine and a 3,5-dimethylisoxazole derivative (McKeown et al., 2014), are known to bind TAF1, but currently, there is no specific inhibitor available for this bromodomain containing protein. Given that CeMMEC1 showed high affinity for TAF1 (2), the inventors decided to further characterize this interaction. Using the BromoKdELECT assay, it was confirmed that CeMMEC1 binds to TAF1 (2), with a Kd of 1.4 µM (see FIG. 4g). Similarly, fluorescence resonance energy transfer (FRET) analysis demonstrated that CeMMEC1 displaced a tetra-acetylated H4 peptide with good efficacy from its TAF1 binding site (data not shown). It has been shown that some kinase inhibitors can behave as bromodomain inhibitors (Ciceri et al., 2014). In order to assess the specificity of CeMMEC1, the inventors tested binding of the compound to the active sites of 97 representative kinases profile. None of these kinases were inhibited by more than 60% at a concentration of 10 µM CeMMEC1, indicating bromodomain-specificity of the compound (see FIG. 8d).

Molecular docking was then used to generate hypotheses on the binding mode of CeMMEC1 and CeMMEC2. CeMMEC2 is a triazolopyridazine and is predicted to bind to BRD4 similarly to other related triazolophthalazines (Fedorov et al., 2014) (see FIG. 4h). The triazole nitrogen is predicted to form a hydrogen bond to a conserved asparagine deep in the peptide binding pocket of BRD4, thereby acting as an acetyllysine mimetic. CeMMEC1 is an N-methylisoquinolinone derivative. Based on the binding of N-methylquinolinone to the bromodomain of ATAD2 (Chaikuad et al., 2014), CeMMEC1 can be modeled into the TAF1 pocket (see FIG. 4i). Its lactam carbonyl is predicted to form a hydrogen bond with N1604 and with Y1561 through a conserved water molecule. In order to test this binding mode, the inventors generated a panel of 29 CeMMEC1 analogs (see FIG. 12). These compounds were tested for their capability to activate RFP in REDS3 cells, and for binding to the bromodomains of BRD4 (1), BRD4 (2), BRD9, CREBBP, EP300 and TAF1 (2) (see FIG. 8e). Overall, the data are consistent with the molecular model of CeMMEC1 binding, as substitutions on the dihydrobenzodioxin moiety are generally tolerated, and most of the isoquinolinones retain some binding to CREBBP and TAF1. Excitingly, two of the analogs tested, compounds 29 and 30, lost all affinity to CREBBP while retaining TAF1 activity. In contrast, compounds 32 and 35 can serve as negative controls, as they bound neither of the tested bromodomain proteins nor did they induce RFP expression in REDS3 cells. Both TAF1 specific compounds are structural isomers of the predicted active-site binding isoquinolinone. In compound 29, the isoquinolinone is changed to a quinolinone, whereas in compound 30 the attachment point and orientation of the central amide are altered. The inventors therefore modelled the binding of the specific compounds to TAF1 (2) and BRD4 (1). Compound 30 was docked into both proteins, but the dihydrobenzodioxin occupies drastically different spaces in the binding pockets caused by the different interactions with W1547 in TAF1 and L92 in BRD4 (see FIG. 8f). The different binding mode in TAF1 enables the ligand to form a hydrogen bond with N1554 (see FIG. 8g), likely explaining the specificity. For compound 29, no convincing docking pose was obtained for BRD4 due to clashes with residues L92 and W81 (see FIG. 8h).

Finally, as the CeMMEC1-analog 29 appeared to be a selective TAF1 inhibitor, the inventors tested for its ability to inhibit binding of BRD4 (1), BRD9, CREBBP, EP300 and TAF1 (2) bromodomains at 10 µM to acetylated substrate (see FIG. 8i). Also among this larger panel, compound 29 showed high selectivity for the TAF1 (2) bromodomain.

TAF1 Synergizes with BRD4 to Mediate Transcriptional Control

The results provided herein showed that the inhibition of TAF1 phenocopies BRD4 inhibition, indicating a possible functional link between the two bromodomain proteins. Indeed, downregulation of TAF1 in REDS3 cells increased RFP expression (see FIG. 9a) and decreased c-MYC expression (see FIG. 5a) to levels comparable induced by BRD4 downregulation. The inventors tested whether these two bromodomain proteins were able to interact directly. 293T cells were transfected with BRD4-FLAG and FLAG pull down performed 48 hours later showed that TAF1 co-immunoprecipitated with FLAG-BRD4 (see FIG. 9b), indicating a direct interplay of these two bromodomain containing proteins in controlling gene expression.

As the results provided herein revealed the role of TAF1 in ensuring BRD4 functionality, the inventors asked whether downregulation of TAF1 could sensitize cells to the inhibition of BRD4. KBM7 cells treated with shRNAs targeting TAF1 or control hairpins were incubated with different concentrations of (S)-JQ1 and cell viability was measured after 96 hours. Downregulation of TAF1 decreased cell viability when (S)-JQ1 was used at concentrations not able to affect control cells, and further impaired cell number at higher concentrations (see FIG. 5b). Similarly, the synergism of the new direct BRD4 inhibitor, CeMMEC2, with TAF1 downregulation was observed (see FIG. 5c). Furthermore, the additional inhibition of TAF1 by CeMMEC1 impaired cell viability in TAF1 downregulated cells (see FIG. 9c), indicating that a strong reduction of TAF1 activity alone can be toxic in these cells.

To further provide evidence for a functional relationship between these two bromodomain containing proteins, the inventors simultaneously inhibited TAF1 and BRD4, with CeMMEC1 or the analogs 29 or 30 (see FIG. 5d), which showed comparable induction of RFP expression in REDS3 cells (see FIG. 5e), and (S)-JQ1 respectively. The combination of these compounds in REDS3 cells further boosted RFP expression beyond the increase in single treatments, indicating cooperation between TAF1 and BRD4 on the remodeling of the RFP locus. The same effect was not achieved when using the TAF1-inactive analogs 32 and 35 (see FIG. 5f).

As KBM7 cells are not particularly sensitive to BRD4 inhibitors, the inventors wanted to test whether the synergy between BRD4 inhibitors and TAF1 inhibitors was conserved in BRD4-dependent cancers. Therefore, it was tested whether the combined inhibition of TAF1 and BRD4 could arrest the proliferation of THP1 and H23 cells, a lung adenocarcinoma cell line also sensitive to the inhibition of BRD4. It was observed that the combination of (S)-JQ1 and CeMMEC1 was more efficiently impairing cell viability than the individual treatments (see FIGS. 5g and 9d). The Bliss independence test (Bliss, 1939) confirmed the synergism between these two treatments and showed that the combination between JQ1S and the analog 29, the most specific in binding TAF1 (2), was the most effective (see FIG. 9e).

Discussion

Chromatin reporter cell lines have been proposed as models to identify modulators of position effect variegation and chromatin-targeting small molecules (Johnson et al., 2008; Best et al., 2011; Wang et al., 2013; Tchasovnikarova et al., 2015). In contrast to previous approaches, the inventors developed a strategy to map chromatin reactivation focused on a specific regulator, BRD4. They selected clones that integrated reporters in fully repressed genomic regions and specifically activated the expression of RFP following BRD4 inhibition. The haploid nature of the reporter cell line makes it easily amenable to genetic screens, and its application for the identification of genes in BRD4 functional pathways will provide further insights into BRD4 biology.

With this reporter cell line validated, the inventors first took a chemical genomics approach and identified compounds that functionally antagonize BRD4. In addition to all known BET inhibitors contained in their library, the inventors identified 13 small molecules that have not been linked to BRD4 biology previously. One of these molecules is panobinostat, a clinically approved histone deacetylase (HDAC) inhibitor. Out of more than 40 HDAC-targeting compounds tested, Panobinostat is the sole compound inducing RFP expression in REDS3 cells, indicating a panobinostat-specific activity. These findings encourage future efforts to fully characterize Panobinostat and all other validated hit compounds regarding their molecular mechanism and protein targets.

The inventors focused their efforts on two compounds that phenocopy BRD4 inhibitors not only by their ability to activate RFP reporter expression but also by repressing c-MYC. One of the hit structures, CeMMEC2, turned out to be a novel direct BRD4 inhibitor. Interestingly, several reports exist in the patent literature describing compounds related to CeMMEC2 to inhibit BRD4 (WO 2014/191894; WO 2014/076146; US 2014/0135336; WO 2014/191896; US 2014/0349990; WO 2012/174487). Moreover, the screen provided herein has also yielded compounds that do not strongly bind BRD4 but still activate the reporter cell line. For one of these compounds, CeMMEC1, the inventors have identified TAF1 as the relevant target in their system. TAF1 is the largest component of the TAF subunits contained in the TFIID core, which is part of the pre-initiation complex (PIC) and serves to recognize the TATA box and correctly place RNAPol II for transcription initiation (Lee et al., 2005; Kloet et al., 2012; Kandiah et al., 2014). Thereby, TAF1 plays a fundamental role in the assembly of the transcription machinery. Similar to BRD4, TAF1 is essential for the viability of many different cell lines (Wang et al., 2015; Blomen et al., 2015), and the two proteins interact not only in the regulation of transcription but also physically in co-immunoprecipitation experiments. The inventors have shown that TAF1 knockdown increases sensitivity to BRD4 inhibition, and BRD4 inhibitors synergize with TAF1 inhibitors, such as CeMMEC1, to impair viability of BRD4-dependent cell lines.

The specific functions of the bromodomains of TAF1 have remained elusive; the results provided herein indicate that the second bromodomain of TAF1 is a relevant target in BRD4 driven cancers. CeMMEC1 proves druggability of this domain and allows further development of isoquinolinones as bromodomain inhibitors (Arrowsmith et al., 2015; Workman et al., 2010; Frye, 2010). More selective analogs such as quinolinone 29 open up the avenue to specifically target TAF1 in cancer.

In summary, the results provided herein successfully validate the application of haploid epigenetic reporters to identify functional pathways and novel chemical structures regulating chromatin organization and transcriptional control.

The results provided herein furthermore demonstrate that the compounds of formula (I), including the exemplary compounds of formula (I) shown in FIG. 12, are potent inhibitors of TAF1 and can thus be used for the therapy of diseases/disorders associated with TAF1, particularly for the treatment or prevention of cancer.

Example 2

The following further compounds of formula (I) according to the invention were synthesized by Enamine Ltd. (Kiev, Ukraine) following the scheme below:

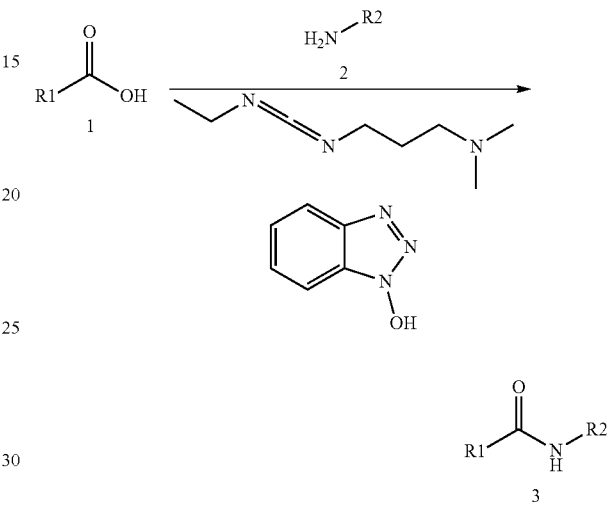

A mixture of acid 1 (1.1 mmol), amine 2 (1.0 mmol), EDC (1.1 mmol), and HOBt (1.6 mmol) in DMF (1 ml) was stirred at room temperature for 24 hours. Chloroform (6 ml) and water (8 ml) was added, organic layer was separated, washed with water (8 ml) twice, dried over $Na_2SO_4$ and evaporated. The crude residue was purified by reversed phase (C-18) chromatography with gradient elution (methanol-water) to yield pure 3.

All compounds were quality controlled by LC-MS, requiring a minimum purity of 90%.

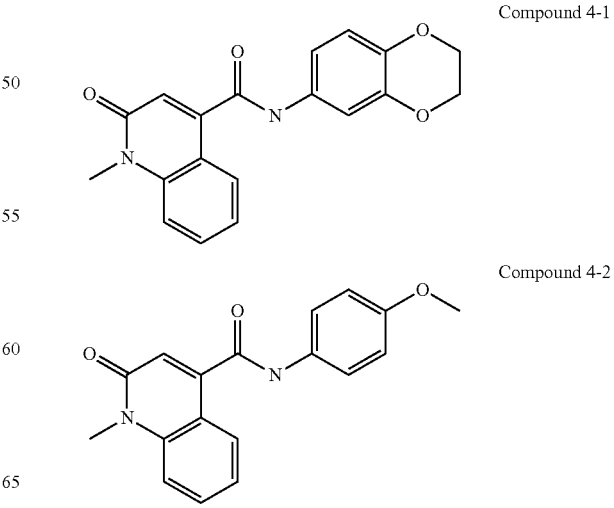

Compound 4-1

Compound 4-2

Compound 4-3
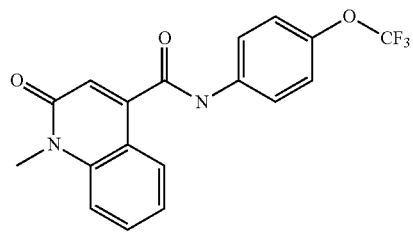
Compound 4-4
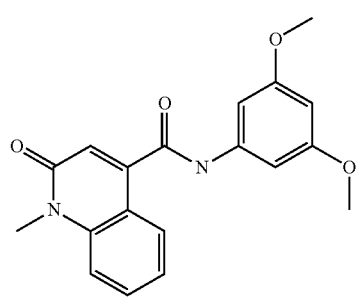
Compound 4-10
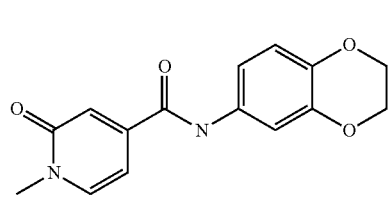
Compound 4-13
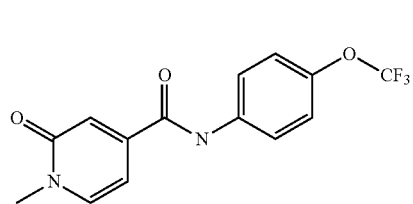
Compound 4-14
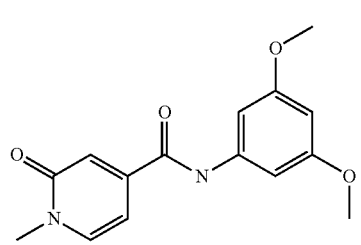
Compound 4-16
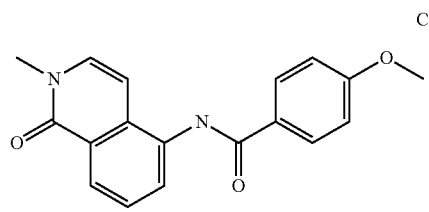
Compound 4-17
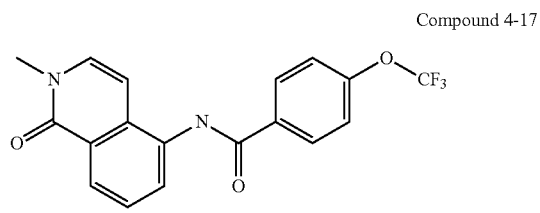
Compound 4-24
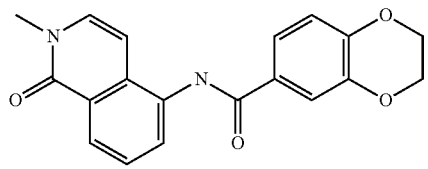
Compound 4-25
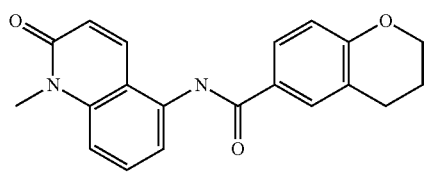
Compound 4-26
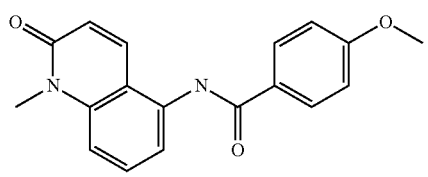
Compound 4-28
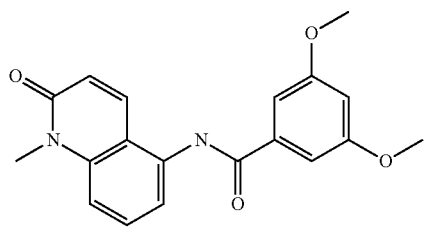
Compound 4-29
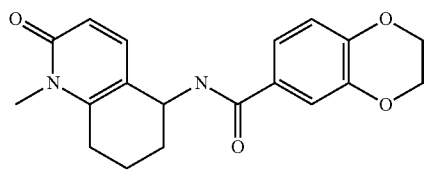
Compound 4-31
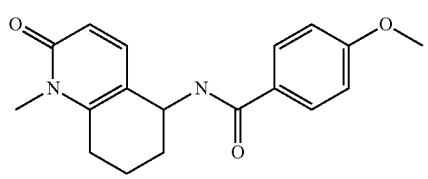
Compound 4-32
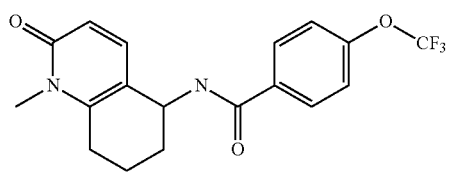

-continued

Compound 4-33

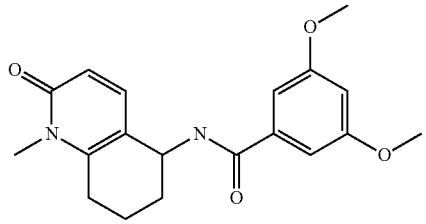

The binding of these compounds to TAF1 was tested by DiscoverX Corporation (Fremont, Calif., USA) in a primary screen using the BROMOscan assay, which is a ligand binding site-directed competition assay that allows to quantitatively measure interactions between test compounds and bromodomains (see Fabian et al., 2005 for an explanation of the principle of this assay), according to the following protocol:

Bromodomain assays: T7 phage strains displaying bromodomains were grown in parallel in 24-well blocks in an E. coli host derived from the BL21 strain. E. coli were grown to log-phase and infected with T7 phage from a frozen stock (multiplicity of infection=0.4) and incubated with shaking at 32° C. until lysis (90-150 minutes). The lysates were centrifuged (5,000×g) and filtered (0.2 µm) to remove cell debris. Streptavidin-coated magnetic beads were treated with biotinylated small molecule or acetylated peptide ligands for 30 minutes at room temperature to generate affinity resins for bromodomain assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining bromodomains, liganded affinity beads, and test compounds in 1x binding buffer (16% SeaBlock, 0.32x PBS, 0.02% BSA, 0.04% Tween 20, 0.004% sodium azide, 7.9 mM DTT). Test compounds were prepared as 1000× stocks in 100% DMSO and subsequently diluted 1:25 in monoethylene glycol (MEG). The compounds were then diluted directly into the assays such that the final concentrations of DMSO and MEG were 0.1% and 2.4%, respectively. All reactions were performed in polypropylene 384-well plates in a final volume of 0.02 ml. The assay plates were incubated at room temperature with shaking for 1 hour and the affinity beads were washed with wash buffer (1× PBS, 0.05% Tween 20). The beads were then re-suspended in elution buffer (1× PBS, 0.05% Tween 20, 2 µM non-biotinylated affinity ligand) and incubated at room temperature with shaking for 30 minutes. The bromodomain concentration in the eluates was measured by qPCR.

The compounds were tested at a concentration of 1 µM, and the % inhibition was determined as follows:

% inhibition=

$$100 - \left(\frac{\text{test compound signal} - \text{positive control signal}}{\text{negative control signal} - \text{positive control signal}}\right) \times 100$$

negative control=DMSO (0% inhibition)
positive control=30 µM BI2536 (100% inhibition)

The % inhibition data for TAF1(BD2) thus obtained are summarized in the table further below.

In addition, the inhibitor binding constants (Kd values) of the compounds 29, 30, 4-1 and 4-26 for TAF1(BD2) were subsequently determined by DiscoverX Corporation (Fremont, Calif., USA) using the BROMOscan assay according to the following protocol:

Bromodomain assays: T7 phage strains displaying bromodomains were grown in parallel in 24-well blocks in an E. coli host derived from the BL21 strain. E. coli were grown to log-phase and infected with T7 phage from a frozen stock (multiplicity of infection=0.4) and incubated with shaking at 32° C. until lysis (90-150 minutes). The lysates were centrifuged (5,000×g) and filtered (0.2 µm) to remove cell debris. Streptavidin-coated magnetic beads were treated with biotinylated small molecule or acetylated peptide ligands for 30 minutes at room temperature to generate affinity resins for bromodomain assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining bromodomains, liganded affinity beads, and test compounds in 1x binding buffer (17% SeaBlock, 0.33× PBS, 0.04% Tween 20, 0.02% BSA, 0.004% sodium azide, 7.4 mM DTT). Test compounds were prepared as 1000× stocks in 100% DMSO. Kds were determined using an 11-point 3-fold compound dilution series with one DMSO control point. All compounds for Kd measurements are distributed by acoustic transfer (non-contact dispensing) in 100% DMSO. The compounds were then diluted directly into the assays such that the final concentration of DMSO was 0.09%. All reactions performed in polypropylene 384-well plates. Each was a final volume of 0.02 ml. The assay plates were incubated at room temperature with shaking for 1 hour and the affinity beads were washed with wash buffer (1× PBS, 0.05% Tween 20). The beads were then re-suspended in elution buffer (1× PBS, 0.05% Tween 20, 2 µM non-biotinylated affinity ligand) and incubated at room temperature with shaking for 30 minutes. The bromodomain concentration in the eluates was measured by qPCR.

Compound handling: An 11-point 3-fold serial dilution of each test compound was prepared in 100% DMSO at 1000× final test concentration. All compounds for Kd measurements are distributed by acoustic transfer (non-contact dispensing) in 100% DMSO. The compounds were then diluted directly into the assays such that the final concentration of DMSO was 0.09%. Most Kds were determined using a compound top concentration=10,000 nM. If the initial Kd determined was <0.169 nM (the lowest concentration tested), the measurement was repeated with a serial dilution starting at a lower top concentration.

Binding constants (Kds) were calculated with a standard dose-response curve using the Hill equation:

$$\text{Response} = \text{Background} + \frac{\text{Signal} - \text{Background}}{1 + (Kd^{Hill\ Slope}/Dose^{Hill\ Slope})}$$

The Hill Slope was set to −1. Curves were fitted using a non-linear least square fit with the Levenberg-Marquardt algorithm.

The results thus obtained are reported in the following table as IC$_{50}$ values [µM] for TAF1(BD2).

| Compound | TAF1_BD2 (% inhibition at 1 µM) | TAF1_BD2 (IC50 µM) |
|---|---|---|
| 29 | | 3.100 |
| 30 | | 4.000 |
| 4-1 | 89 | 0.250 |
| 4-2 | 9 | |
| 4-3 | 20 | |
| 4-4 | 48 | |
| 4-10 | 3 | |
| 4-13 | 3 | |
| 4-14 | 20 | |
| 4-16 | 34 | |
| 4-17 | 11 | |
| 4-24 | 58 | |
| 4-25 | 4 | |
| 4-26 | 82 | 0.056 |
| 4-28 | 50 | |
| 4-29 | 32 | |
| 4-31 | 34 | |
| 4-32 | 10 | |
| 4-33 | 11 | |

These results further confirm that the compounds of formula (I) according to the present invention are effective in inhibiting TAF1 and can thus be used for the therapy of diseases/disorders associated with TAF1, particularly for the treatment or prevention of cancer.

REFERENCES

Andersson, B. et al. KBM-7, a human myeloid leukemia cell line with double Philadelphia chromosomes lacking normal c-ABL and BCR transcripts. *Leukemia* 9, 2100-8 (1995).

Arrowsmith, C. H. et al. The promise and peril of chemical probes. *Nat. Chem. Biol.* 11, (2015).

Banerjee, C. et al. BET bromodomain inhibition as a novel strategy for reactivation of HIV-1. *J. Leukoc. Biol.* 92, 1147-1154 (2012).

Best, A. M., Chang, J., Dull, A. B., Beutler, J. A. & Martinez, E. D. Identification of Four Potential Epigenetic Modulators from the NCI Structural Diversity Library Using a Cell-Based Assay. *J. Biomed. Biotechnol.* 2011, 868095 (2011).

Bielefeld-Sevigny, M. AlphaLISA immunoassay platform-the 'no-wash' high-throughput alternative to ELISA. *Assay Drug Dev. Technol.* 7, 90-92 (2009).

Bliss, C. I. The toxicity of poisons applied jointly. *Ann. Appl. Biol.* 26, 585-615 (1939).

Blomen, V. A. et al. Gene essentiality and synthetic lethality in haploid human cells Vincent. *Science* 350, (2015).

Chaikuad, A., Petros, A. M., Fedorov, O., Xu, J. & Knapp, S. Structure-based approaches towards identification of fragments for the low-druggability ATAD2 bromodomain. *Medchemcomm* 5, 1843-1848 (2014).

Ciceri, P. et al. Dual kinase-bromodomain inhibitors for rationally designed polypharmacology. *Nat. Chem. Biol.* 10, 305-312 (2014).

Devaiah, B. N. & Singer, D. S. Two faces of brd4: mitotic bookmark and transcriptional lynchpin. *Transcription* 4, 13-17 (2013).

Dey, A., Chitsaz, F., Abbasi, A., Misteli, T. & Ozato, K. The double bromodomain protein Brd4 binds to acetylated chromatin during interphase and mitosis. *Proc. Natl. Acad. Sci. U.S.A* 100, 8758-63 (2003).

The ENCODE Project Consortium. An Integrated Encyclopedia of DNA Elements in the Human Genome. *Nature* 489, 57-74 (2012).

Fabian, M. A. et al. A small molecule-kinase interaction map for clinical kinase inhibitors. *Nat. Biotechnol.* 23, 329-336 (2005).

Fedorov, O. et al. [1,2,4]Triazolo[4,3-a]phthalazines: Inhibitors of Diverse Bromodomains. *J. Med. Chem.* 57, 462-476 (2014).

Filippakopoulos, P. et al. Selective inhibition of BET bromodomains. *Nature* 468, 1067-1073 (2010).

Filippakopoulos, P. et al. Histone recognition and large-scale structural analysis of the human bromodomain family. *Cell* 149, 214-231 (2012).

Filippakopoulos, P. et al. Benzodiazepines and benzotriazepines as protein interaction inhibitors targeting bromodomains of the BET family. *Bioorganic Med. Chem.* 20, 1878-1886 (2012).

Filippakopoulos, P. & Knapp, S. Targeting bromodomains: epigenetic readers of lysine acetylation. *Nat. Rev. Drug Discov.* 13, 337-56 (2014).

Fish, P. V. et al. Identification of a chemical probe for bromo and extra C-terminal bromodomain inhibition through optimization of a fragment-derived hit. *J. Med. Chem.* 55, 9831-9837 (2012).

Floyd, S. R. et al. The bromodomain protein Brd4 insulates chromatin from DNA damage signalling. *Nature* 498, 246-50 (2013).

Frye, S. V. The art of the chemical probe. *Nat Chem Biol* 6, 159-161 (2010).

Hammitzsch, A. et al. CBP30, a selective CBP/p300 bromodomain inhibitor, suppresses human Th17 responses. *Proc. Natl. Acad. Sci.* 112, (2015).

Hay, D. a. et al. Discovery and optimization of small-molecule ligands for the CBP/p300 bromodomains. *J. Am. Chem. Soc.* 136, 9308-9319 (2014).

Huang, D. W., Sherman, B. T. & Lempicki, R. a. Systematic and integrative analysis of large gene lists using DAVID bioinformatics resources. *Nat. Protoc.* 4, 44-57 (2009).

Huang, D. W., Sherman, B. T. & Lempicki, R. a. Bioinformatics enrichment tools: Paths toward the comprehensive functional analysis of large gene lists. *Nucleic Acids Res.* 37, 1-13 (2009).

Johnson, R. L., Huang, W., Jadhav, A., Austin, C. P. & Martinez, E. D. A Quantitative High-Throughput Screen Identifies Potential Epigenetic Modulators of Gene Expression. *Anal. Biochem.* 375, 237-248 (2008).

Kandiah, E., Trowitzsch, S., Gupta, K., Haffke, M. & Berger, I. More pieces to the puzzle: Recent structural insights into class II transcription initiation. *Curr. Opin. Struct. Biol.* 24, 91-97 (2014).

Kent, W. J. et al. The Human Genome Browser at UCSC. *Genome Res.* 12, 996-1006 (2002).

Kim, D. et al. TopHat2: accurate alignment of transcriptomes in the presence of insertions, deletions and gene fusions. *Genome Biol.* 14, R36 (2013).

Kloet, S. L., Whiting, J. L., Gafken, P., Ranish, J. & Wang, E. H. Phosphorylation-Dependent Regulation of Cyclin D1 and Cyclin A Gene Transcription by TFIID Subunits TAF1 and TAF7. *Mol. Cell. Biol.* 32, 3358-3369 (2012).

Lee, D. et al. Functional Characterization of Core Promoter Elements: the Downstream Core Element Is Recognized by TAF1. *Mol. Cell. Biol.* 25, 9674-9686 (2005).

McKeown, M. R. et al. Biased multicomponent reactions to develop novel bromodomain inhibitors. *J. Med. Chem.* 57, 9019-27 (2014).

McLure, K. G. et al. RVX-208, an inducer of ApoA-I in humans, is a BET bromodomain antagonist. *PLoS One* 8, (2013).

Mirguet, O. et al. Discovery of epigenetic regulator i-bet762: Lead optimization to afford a clinical candidate inhibitor of the bet bromodomains. *J. Med. Chem.* 56, 7501-7515 (2013).

Mootha, V. K. et al. Integrated analysis of protein composition, tissue diversity, and gene regulation in mouse mitochondria. *Cell* 115, 629-640 (2003).

Nagarajan, S. et al. Bromodomain Protein BRD4 Is Required for Estrogen Receptor-Dependent Enhancer Activation and Gene Transcription. *Cell Rep.* 8, 460-469 (2014).

Picaud, S. et al. Generation of a selective small molecule inhibitor of the CBP/p300 bromodomain for leukemia therapy. *Cancer Res.* 75, 5106-5120 (2015).

Pott, S. & Lieb, J. D. What are super-enhancers ? *Nat. Publ. Gr.* 47, 8-12 (2015).

Roe, J.-S., Mercan, F., Rivera, K., Pappin, D. J. & Vakoc, C. R. BET Bromodomain Inhibition Suppresses the Function of Hematopoietic Transcription Factors in Acute Myeloid Leukemia. *Mol. Cell* 58, 1028-1039 (2015).

Running, D. M., Ligon, J. B. & Miskioglu, I. A Simple Statistical Parameter for Use in Evaluation and Validation of High Throughput Screening Assays. *J. Biomol. Screen.* 4, 928-940 (1999).

Schermelleh, L. et al. Subdiffraction multicolor imaging of the nuclear periphery with 3D structured illumination microscopy. *Science* 320, 1332-1336 (2008).

Seal, J. et al. Identification of a novel series of BET family bromodomain inhibitors: Binding mode and profile of I-BET151 (GSK1210151A). *Bioorganic Med. Chem. Lett.* 22, 2968-2972 (2012).

Subramanian, A. et al. Gene set enrichment analysis: a knowledge-based approach for interpreting genome-wide expression profiles. *Proc. Natl. Acad. Sci. U.S.A* 102, 15545-50 (2005).

Tchasovnikarova, I. A. et al. Epigenetic silencing by the HUSH complex mediates position-effect variegation in human cells. *Science* 348, 1481-1485 (2015).

Towbin, B. D. et al. Step-wise methylation of histone H3K9 positions heterochromatin at the nuclear periphery. *Cell* 150, 934-947 (2012).

Wang, R., Li, Q., Helfer, C. M., Jiao, J. & You, J. Bromodomain protein Brd4 associated with acetylated chromatin is important for maintenance of higher-order chromatin structure. *J. Biol. Chem.* 287, 10738-10752 (2012).

Wang, L., Wang, S. & Li, W. RSeQC: Quality control of RNA-seq experiments. *Bioinformatics* 28, 2184-2185 (2012).

Wang, L. et al. A small molecule modulates Jumonji histone demethylase activity and selectively inhibits cancer growth. *Nat. Commun.* 4, 2035 (2013).

Wang, T. et al. Identification and characterization of essential genes in the human genome. *Science* 350, 1096-1101 (2015).

Whyte, W. a et al. Master Transcription Factors and Mediator Establish Super-Enhancers at Key Cell Identity Genes. *Cell* 153, 307-319 (2013).

Workman, P. & Collins, I. Probing the Probes: Fitness Factors For Small Molecule Tools. *Chem. Biol.* 17, 561-577 (2010).

Wu, S. Y. & Chiang, C. M. The double bromodomain-containing chromatin adaptor Brd4 and transcriptional regulation. *J. Biol. Chem.* 282, 13141-13145 (2007).

Wu, T., Pinto, H. B., Kamikawa, Y. F. & Donohoe, M. E. The BET Family Member BRD4 Interacts with OCT4 and Regulates Pluripotency Gene Expression. *Stem Cell Reports* 4, 390-403 (2015).

Wyce, A. et al. BET Inhibition Silences Expression of MYCN and BCL2 and Induces Cytotoxicity in Neuroblastoma Tumor Models. *PLoS One* 8, 1-15 (2013).

Yang, Z., He, N. & Zhou, Q. Brd4 recruits P-TEFb to chromosomes at late mitosis to promote G1 gene expression and cell cycle progression. *Mol. Cell. Biol.* 28, 967-976 (2008).

Zhu, J. et al. Reactivation of Latent HIV-1 by Inhibition of BRD4. *Cell Rep.* 29, 997-1003 (2012).

Zuber, J., Shi, J., Wang, E. & Rappaport, A. RNAi screen identifies Brd4 as a therapeutic target in acute myeloid leukaemia. *Nature* 478, 524-528 (2011).

---

The invention claimed is:
1. A pharmaceutical composition comprising a compound of the following formula (I):

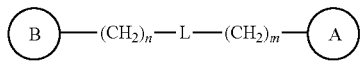

wherein:
ring B is a group having the following structure:

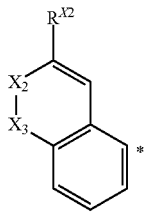

wherein ring B is attached to the remainder of the compound of formula (I) via the ring carbon atom marked with an asterisk (*),
and wherein the phenyl group comprised in ring B is optionally substituted with one or more groups $R^{X31}$;
one of the ring atoms $X_2$ and $X_3$ is $N(R^{X1})$, and the other one of said ring atoms $X_2$ and $X_3$ is $C(=O)$;
$R^{X1}$ is selected from the group consisting of hydrogen, $C_{1-5}$ alkyl, $-CO(C_{1-5}$ alkyl), $-(C_{0-3}$ alkylene)-aryl, and heteroaryl, wherein the aryl comprised in said $-(C_{0-3}$ alkylene)-aryl and said heteroaryl are each optionally substituted with one or more groups $R^{X11}$;
$R^{X2}$ is selected from the group consisting of hydrogen, $C_{1-5}$ alkyl, $C_{2-5}$ alkenyl, $C_{2-5}$ alkynyl, $-(C_{0-3}$ alkylene)-OH, $-(C_{0-3}$ alkylene)-O($C_{1-5}$ alkyl), $-(C_{0-3}$ alkylene)-O($C_{1-5}$ alkylene)-OH, $-(C_{0-3}$ alkylene)-O($C_{1-5}$ alkylene)-O($C_{1-5}$ alkyl), $-(C_{0-3}$ alkylene)-SH, $-(C_{0-3}$ alkylene)-S($C_{1-5}$ alkyl), $-(C_{0-3}$ alkylene)-$NH_2$, $-(C_{0-3}$ alkylene)-NH($C_{1-5}$ alkyl), $-(C_{0-3}$ alkylene)-N($C_{1-5}$ alkyl)($C_{1-5}$ alkyl), $-(C_{0-3}$ alkylene)-halogen, $-(C_{0-3}$ alkylene)-($C_{1-5}$ haloalkyl), $-(C_{0-3}$ alkylene)-O—($C_{1-5}$ haloalkyl), $-(C_{0-3}$ alkylene)-$CF_3$, $-(C_{0-3}$ alkylene)-CN, $-(C_{0-3}$ alkylene)-$NO_2$, $-(C_{0-3}$ alkylene)-CHO, $-(C_{0-3}$ alkylene)-CO—($C_{1-5}$ alkyl), $-(C_{0-3}$ alkylene)-COOH, $-(C_{0-3}$ alkylene)-CO—O—($C_{1-5}$ alkyl), $-(C_{0-3}$ alkylene)-O—CO—($C_{1-5}$ alkyl), $-(C_{0-3}$ alkylene)-CO—$NH_2$, $-(C_{0-3}$ alkylene)-CO—NH($C_{1-5}$ alkyl), $-(C_{0-3}$ alkylene)-CO—N($C_{1-5}$ alkyl)($C_{1-5}$ alkyl), $-(C_{0-3}$ alkylene)-NH—CO—($C_{1-5}$ alkyl), $-(C_{0-3}$ alkylene)-N($C_{1-5}$ alkyl)-CO—($C_{1-5}$ alkyl), $-(C_{0-3}$ alkylene)-$SO_2$—$NH_2$, $-(C_{0-3}$ alkylene)-$SO_2$—NH($C_{1-5}$ alkyl), $-(C_{0-3}$ alkylene)-$SO_2$—N($C_{1-5}$ alkyl)($C_{1-5}$ alkyl), $-(C_{0-3}$ alkylene)-NH—$SO_2$—($C_{1-5}$ alkyl), and $-(C_{0-3}$ alkylene)-N($C_{1-5}$ alkyl)-$SO_2$—($C_{1-5}$ alkyl);
each $R^{X11}$ is independently selected from the group consisting of $C_{1-5}$ alkyl, $C_{2-5}$ alkenyl, $C_{2-5}$ alkynyl, $-(C_{0-3}$ alkylene)-OH, $-(C_{0-3}$ alkylene)-O($C_{1-5}$ alkyl), $-(C_{0-3}$ alkylene)-O($C_{1-5}$ alkylene)-OH, $-(C_{0-3}$ alkylene)-O($C_{1-5}$ alkylene)-O($C_{1-5}$ alkyl), $-(C_{0-3}$ alkylene)-SH, $-(C_{0-3}$ alkylene)-S($C_{1-5}$ alkyl), $-(C_{0-3}$ alkylene)-$NH_2$, $-(C_{0-3}$ alkylene)-NH($C_{1-5}$ alkyl), $-(C_{0-3}$ alkylene)-N($C_{1-5}$ alkyl)($C_{1-5}$ alkyl), $-(C_{0-3}$ alkylene)-halogen, $-(C_{0-3}$ alkylene)-($C_{1-5}$ haloalkyl), $-(C_{0-3}$ alkylene)-O—($C_{1-5}$ haloalkyl), $-(C_{0-3}$ alkylene)-$CF_3$, $-(C_{0-3}$ alkylene)-CN, $-(C_{0-3}$ alkylene)-$NO_2$, $-(C_{0-3}$ alkylene)-CHO, $-(C_{0-3}$ alkylene)-CO—($C_{1-5}$ alkyl), $-(C_{0-3}$ alkylene)-COOH, $-(C_{0-3}$ alkylene)-CO—O—($C_{1-5}$ alkyl), $-(C_{0-3}$ alkylene)-O—CO—($C_{1-5}$ alkyl), $-(C_{0-3}$ alkylene)-CO—$NH_2$, $-(C_{0-3}$ alkylene)-CO—NH($C_{1-5}$ alkyl), $-(C_{0-3}$ alkylene)-CO—N($C_{1-5}$ alkyl)($C_{1-5}$ alkyl), $-(C_{0-3}$ alkylene)-NH—CO—($C_{1-5}$ alkyl), $-(C_{0-3}$ alkylene)-N($C_{1-5}$ alkyl)-CO—($C_{1-5}$ alkyl), $-(C_{0-3}$ alkylene)-$SO_2$—$NH_2$, $-(C_{0-3}$ alkylene)-$SO_2$—NH($C_{1-5}$ alkyl), $-(C_{0-3}$ alkylene)-$SO_2$—N($C_{1-5}$ alkyl)($C_{1-5}$ alkyl), $-(C_{0-3}$ alkylene)-NH—$SO_2$—($C_{1-5}$ alkyl), and $-(C_{0-3}$ alkylene)-N($C_{1-5}$ alkyl)-$SO_2$—($C_{1-5}$ alkyl);
each $R^{X31}$ is independently selected from the group consisting of $C_{1-5}$ alkyl, $C_{2-5}$ alkenyl, $C_{2-5}$ alkynyl, $-(C_{0-3}$ alkylene)-OH, $-(C_{0-3}$ alkylene)-O($C_{1-5}$ alkyl)-OH, $-(C_{0-3}$ alkylene)-O($C_{1-5}$ alkylene)-O($C_{1-5}$ alkyl), $-(C_{0-3}$ alkylene)-SH, $-(C_{0-3}$ alkylene)-S($C_{1-5}$ alkyl), $-(C_{0-3}$ alkylene)-$NH_2$, $-(C_{0-3}$ alkylene)-NH($C_{1-5}$ alkyl), $-(C_{0-3}$ alkylene)-N($C_{1-5}$ alkyl)($C_{1-5}$ alkyl), $-(C_{0-3}$ alkylene)-halogen, $-(C_{0-3}$ alkylene)-($C_{1-5}$ haloalkyl), $-(C_{0-3}$ alkylene)-$CF_3$, $-(C_{0-3}$ alkylene)-CN, $-(C_{0-3}$ alkylene)-$NO_2$, $-(C_{0-3}$ alkylene)-CHO, $-(C_{0-3}$ alkylene)-CO—($C_{1-5}$ alkyl), $-(C_{0-3}$ alkylene)-COOH, $-(C_{0-3}$ alkylene)-CO—O—($C_{1-5}$ alkyl), $-(C_{0-3}$ alkylene)-O—CO—($C_{1-5}$ alkyl), $-(C_{0-3}$ alkylene)-CO—$NH_2$, $-(C_{0-3}$ alkylene)-CO—NH($C_{1-5}$ alkyl), $-(C_{0-3}$ alkylene)-CO—N($C_{1-5}$ alkyl)($C_{1-5}$ alkyl), $-(C_{0-3}$ alkylene)-NH—CO—($C_{1-5}$ alkyl), $-(C_{0-3}$ alkylene)-N($C_{1-5}$ alkyl)-CO—($C_{1-5}$ alkyl), $-(C_{0-3}$ alkylene)-$SO_2$—$NH_2$, $-(C_{0-3}$ alkylene)-$SO_2$—NH($C_{1-5}$ alkyl), $-(C_{0-3}$ alkylene)-$SO_2$—N($C_{1-5}$ alkyl)($C_{1-5}$ alkyl), $-(C_{0-3}$ alkylene)-NH—$SO_2$—($C_{1-5}$ alkyl), and $-(C_{0-3}$ alkylene)-N($C_{1-5}$ alkyl)-$SO_2$—($C_{1-5}$ alkyl); and
ring A is selected from the group consisting of phenyl, 1,4-benzodioxan-6-yl, 1-benzoxan-6-yl, 1,3-benzodioxolan-5-yl, 1-benzoxolan-5-yl, and 1,5-benzodioxepan-7-yl, wherein said phenyl, said 1,4-benzodioxan-6-yl, said 1-benzoxan-6-yl, said 1,3-benzodioxolan-5-yl, said 1-benzoxolan-5-yl, and said 1,5-benzodioxepan-7-yl are each optionally substituted with one or more groups $R^A$;
each $R^A$ is independently selected from the group consisting of $C_{1-5}$ alkyl, $C_{2-5}$ alkenyl, $C_{2-5}$ alkynyl, $-(C_{0-3}$ alkylene)-OH, $-(C_{0-3}$ alkylene)-O($C_{1-5}$ alkyl), $-(C_{0-3}$ alkylene)-O($C_{1-5}$ alkylene)-OH, $-(C_{0-3}$ alkylene)-O($C_{1-5}$ alkylene)-O($C_{1-5}$ alkyl), $-(C_{0-3}$ alkylene)-SH, $-(C_{0-3}$ alkylene)-S($C_{1-5}$ alkyl), $-(C_{0-3}$ alkylene)-$NH_2$, $-(C_{0-3}$ alkylene)-NH($C_{1-5}$ alkyl), $-(C_{0-3}$ alkylene)-N($C_{1-5}$ alkyl)($C_{1-5}$ alkyl), $-(C_{0-3}$ alkylene)-halogen, $-(C_{0-3}$ alkylene)-($C_{1-5}$ haloalkyl), $-(C_{0-3}$ alkylene)-O—($C_{1-5}$ haloalkyl), $-(C_{0-3}$ alkylene)-$CF_3$, $-(C_{0-3}$ alkylene)-CN, $-(C_{0-3}$ alkylene)-$NO_2$, $-(C_{0-3}$ alkylene)-CHO, $-(C_{0-3}$ alkylene)-CO—($C_{1-5}$ alkyl), $-(C_{0-3}$ alkylene)-COOH, $-(C_{0-3}$ alkylene)-CO—O—($C_{1-5}$ alkyl), $-(C_{0-3}$ alkylene)-O—CO—($C_{1-5}$ alkyl), $-(C_{0-3}$ alkylene)-CO—$NH_2$, $-(C_{0-3}$ alkylene)-CO—NH($C_{1-5}$ alkyl), $-(C_{0-3}$ alkylene)-CO—N($C_{1-5}$ alkyl)($C_{1-5}$ alkyl), $-(C_{0-3}$ alkylene)-NH—CO—($C_{1-5}$ alkyl), $-(C_{0-3}$ alkylene)-N($C_{1-5}$ alkyl)-CO—($C_{1-5}$ alkyl), $-(C_{0-3}$ alkylene)-$SO_2$—$NH_2$, $-(C_{0-3}$ alkylene)-$SO_2$—NH($C_{1-5}$ alkyl), $-(C_{0-3}$ alkylene)-$SO_2$—N($C_{1-5}$ alkyl)($C_{1-5}$ alkyl), $-(C_{0-3}$ alkylene)-NH—$SO_2$—($C_{1-5}$ alkyl), $-(C_{0-3}$ alkylene)-N($C_{1-5}$ alkyl)-$SO_2$—($C_{1-5}$ alkyl), $-(C_{0-3}$ alkylene)-cycloalkyl, $-(C_{0-3}$ alkylene)-

O-cycloalkyl, —(C$_{0-3}$ alkylene)-O(C$_{1-5}$ alkylene)-cycloalkyl, —(C$_{0-3}$ alkylene)-heterocycloalkyl, —(C$_{0-3}$ alkylene)-O-heterocycloalkyl, and —(C$_{0-3}$ alkylene)-O(C$_{1-5}$ alkylene)-heterocycloalkyl;

L is —N(R$^{L1}$)—CO—;

R$^{L1}$ is hydrogen or C$_{1-5}$ alkyl;

n is 0 or 1; and m is 0 or 1;

or a pharmaceutically acceptable salt or solvate thereof;

and a pharmaceutically acceptable excipient.

2. The pharmaceutical composition of claim 1, wherein X$_2$ is C(=O), and X$_3$ is N(R$^{X1}$).

3. The pharmaceutical composition of claim 1, wherein ring A is phenyl, wherein said phenyl is optionally substituted with one or more groups R$^A$.

4. The pharmaceutical composition of claim 1, wherein said compound is a compound of any one of the following formulae:

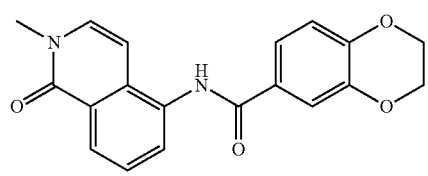
30

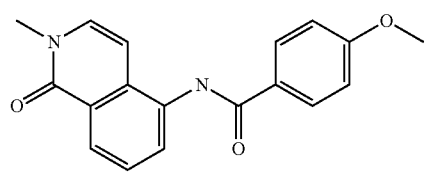
4-16

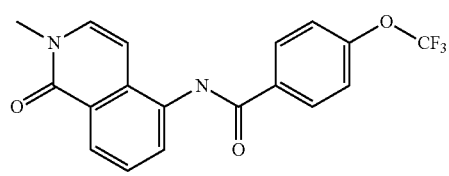
4-17

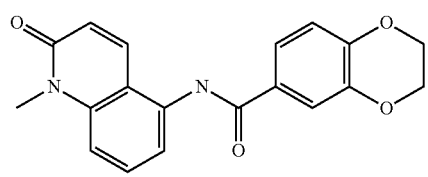
4-24

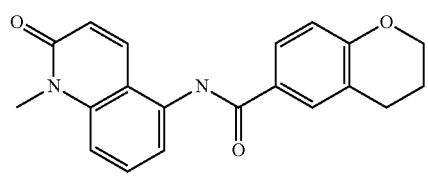
4-25

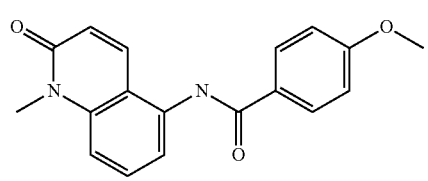
4-26

-continued

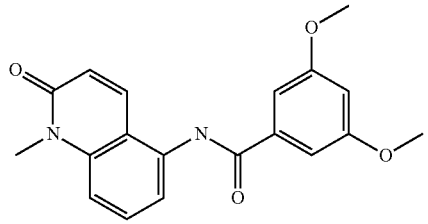
4-28 or a pharmaceutically acceptable salt or solvate thereof.

5. A compound having any one of the following formulae:

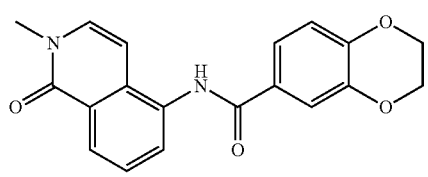
30

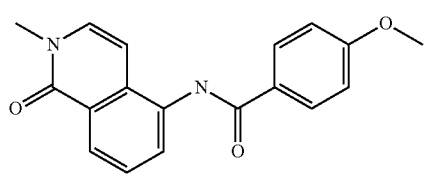
4-16

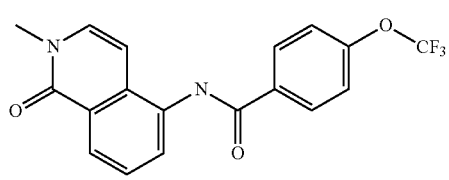
4-17

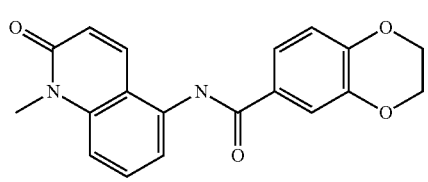
4-24

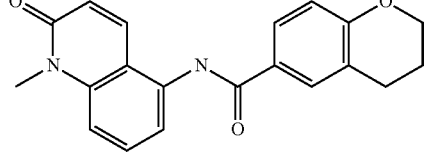
4-25

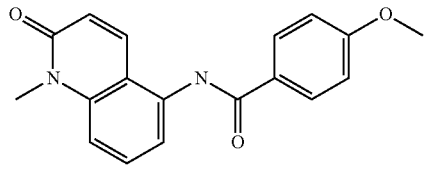
4-26

-continued 4-28

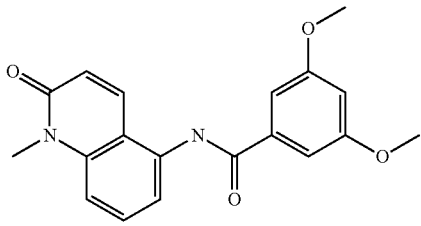

or a pharmaceutically acceptable salt or solvate thereof.

6. A method of treating cancer, the method comprising administering a compound of the following formula (I) or a pharmaceutically acceptable salt or solvate thereof to a subject in need thereof:

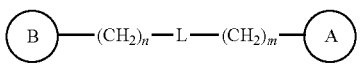
(I)

wherein:

ring B is a group having the following structure:

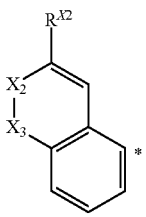

wherein ring B is attached to the remainder of the compound of formula (I) via the ring carbon atom marked with an asterisk (*), and wherein the phenyl group comprised in ring B is optionally substituted with one or more groups $R^{X31}$;

one of the ring atoms $X_2$ and $X_3$ is $N(R^{X1})$, and the other one of said ring atoms $X_2$ and $X_3$ is $C(=O)$;

$R^{X1}$ is selected from the group consisting of hydrogen, $C_{1-5}$ alkyl, —CO($C_{1-5}$ alkyl), —($C_{0-3}$ alkylene)-aryl, and heteroaryl, wherein the aryl comprised in said —($C_{0-3}$ alkylene)-aryl and said heteroaryl are each optionally substituted with one or more groups $R^{X11}$;

$R^{X2}$ is selected from the group consisting of hydrogen, $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O ($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-$CF_3$, —($C_{0-3}$ alkylene)-CN, —($C_{0-3}$ alkylene)-$NO_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{15}$ alkyl)($C_{1-5}$ alkyl), —($C_{0-3}$ alkylene)-NH-$SO_2$—($C_{1-5}$ alkyl), and —($C_{0-3}$ alkylene)-N($C_{1-5}$ alkyl)-$SO_2$—($C_{1-5}$ alkyl);

each $R^{X11}$ is independently selected from the group consisting of $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O ($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-$CF_3$, —($C_{0-3}$ alkylene)-CN, —($C_{0-3}$ alkylene)-$NO_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), and —($C_{0-3}$ alkylene)-N($C_{1-5}$ alkyl)-$SO_2$—($C_{1-5}$ alkyl);

each $R^{X31}$ is independently selected from the group consisting of $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O ($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-$CF_3$, —($C_{0-3}$ alkylene)-CN, —($C_{0-3}$ alkylene)-$NO_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), and —($C_{0-3}$ alkylene)-N($C_{1-5}$ alkyl)-$SO_2$—($C_{1-5}$ alkyl);

ring A is selected from the group consisting of phenyl, 1,4-benzodioxan-6-yl, 1-benzoxan-6-yl, 1,3-benzodioxolan-5-yl, 1-benzoxolan-5-yl, and 1,5-benzodioxepan-7-yl, wherein said phenyl, said 1,4-benzodioxan-6-yl, said 1-benzoxan-6-yl, said 1,3-benzodioxolan-5-yl, said 1-benzoxolan-5-yl, and said 1,5-benzodioxepan-7-yl are each optionally substituted with one or more groups $R^A$;

each $R^A$ is independently selected from the group consisting of $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O ($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-$CF_3$, —(C$_{0-3}$ alkylene)-CN, —(C$_{0-3}$ alkylene)-NO$_2$, —(C$_{0-3}$ alkylene)-CHO, —(C$_{0-3}$ alkylene)-CO—(C$_{1-5}$ alkyl), —(C$_{0-3}$ alkylene)-COOH, —(C$_{0-3}$ alkylene)-CO—O—(C$_{1-5}$ alkyl), —(C$_{0-3}$ alkylene)-O—CO—(C$_{1-5}$ alkyl), —(C$_{0-3}$ alkylene)-CO—NH$_2$, —(C$_{0-3}$ alkylene)-CO—NH(C$_{1-5}$ alkyl), —(C$_{0-3}$ alkylene)-CO—N(C$_{1-5}$ alkyl)(C$_{1-5}$ alkyl), —(C$_{0-3}$ alkylene)-NH—CO—(C$_{1-5}$ alkyl), —(C$_{0-3}$ alkylene)-N(C$_{1-5}$ alkyl)-CO—(C$_{1-5}$ alkyl), —(C$_{0-3}$ alkylene)-SO$_2$—NH$_2$, —(C$_{0-3}$ alkylene)-SO$_2$—NH(C$_{1-5}$ alkyl), —(CO-3 alkylene)-SO$_2$—N(C$_{1-5}$ alkyl)(C$_{1-5}$ alkyl), —(C$_{0-3}$ alkylene)-NH—SO$_2$—(C$_{1-5}$ alkyl), —(C$_{0-3}$ alkylene)-N(C$_{1-5}$ alkyl)-SO$_2$—(C$_{1-5}$ alkyl), —(CO-3 alkylene)-cycloalkyl, —(C$_{0-3}$ alkylene)-O-cycloalkyl, —(C$_{0-3}$ alkylene)-O(C$_{1-5}$ alkylene)-cycloalkyl, —(C$_{0-3}$ alkylene)-heterocycloalkyl, —(C$_{0-3}$ alkylene)-O-heterocycloalkyl, and —(C$_{0-3}$ alkylene)-O(C$_{1-5}$ alkylene)-heterocycloalkyl;

L is —N(R$^{L1}$)—CO—;
R$^{L1}$ is hydrogen or C$_{1-5}$ alkyl;
n is 0 or 1; and
m is 0 or 1.

7. The method of claim 6, wherein X$_2$ is C(=O), and X$_3$ is N(R$^{X1}$).

8. The method of claim 6, wherein ring A is phenyl, wherein said phenyl is optionally substituted with one or more groups R$^4$.

9. The method of claim 6, wherein the moiety —(CH$_2$)$_n$-L-(CH$_2$)$_m$— is —(CH$_2$)$_n$—N(R$^{L1}$)—CO—(CH$_2$)$_m$—, n is 0, and m is 0.

10. The method of claim 6, wherein said compound is a compound of any one of the following formulae:

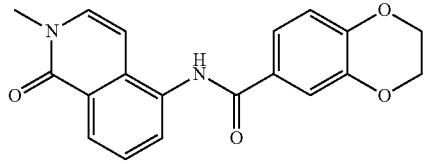
30

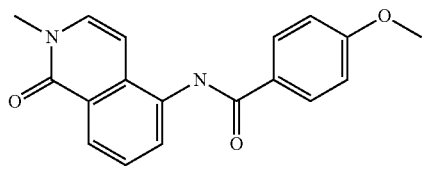
4-16

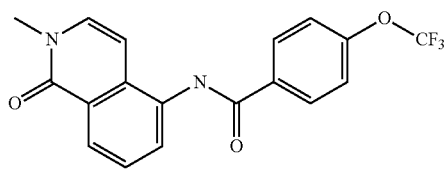
4-17

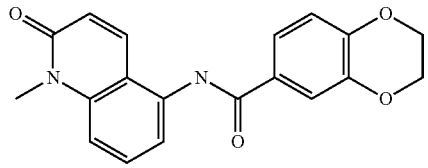
4-24

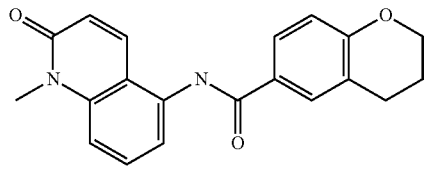
4-25

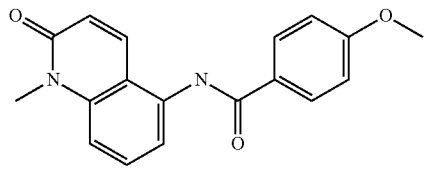
4-26

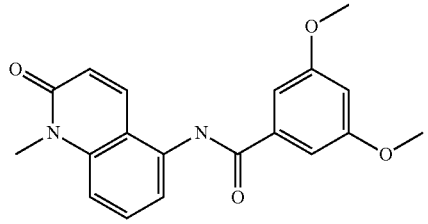
4-28 or a pharmaceutically acceptable salt or solvate thereof.

11. The method of claim 6, wherein said cancer is selected from the group consisting of prostate carcinoma, breast cancer, acute myeloid leukemia, multiple myeloma, glioblastoma, and NUT midline carcinoma.

12. The method of claim 6, wherein the method comprises administering said compound in combination with a BRD4 inhibitor.

13. The method of claim 12, wherein said BRD4 inhibitor is selected from CeMMEC2, (S)-JQ1, I-BET 151, I-BET 762, PF-1, bromosporine, OTX-015, TEN-010, CPI-203, CPI-0610, RVX-208, BI2536, TG101348, LY294002, or a pharmaceutically acceptable salt or solvate of any one of these agents.

14. The method of claim 6, wherein the subject is a human.

* * * * *